(12) United States Patent
Iba et al.

(10) Patent No.: US 10,844,376 B2
(45) Date of Patent: Nov. 24, 2020

(54) STRUCTURALLY-ENHANCED MIRNA INHIBITOR S-TUD

(71) Applicants: The University of Tokyo, Tokyo (JP); GeneDesign, Inc., Osaka (JP)

(72) Inventors: Hideo Iba, Tokyo (JP); Takeshi Haraguchi, Tokyo (JP); Hirokazu Nankai, Osaka (JP); Hideaki Sato, Osaka (JP)

(73) Assignees: University of Tokyo, Tokyo (JP); GeneDesign, Inc., Osaka (JP)

( * ) Notice: Subject to any disclaimer, the term of this patent is extended or adjusted under 35 U.S.C. 154(b) by 54 days.

(21) Appl. No.: 15/761,018

(22) PCT Filed: Sep. 16, 2016

(86) PCT No.: PCT/JP2016/004252
§ 371 (c)(1),
(2) Date: Mar. 16, 2018

(87) PCT Pub. No.: WO2017/047097
PCT Pub. Date: Mar. 23, 2017

(65) Prior Publication Data
US 2018/0223281 A1   Aug. 9, 2018

(30) Foreign Application Priority Data
Sep. 18, 2015   (JP) .................. 2015-185365

(51) Int. Cl.
*C12N 15/113* (2010.01)
*A61K 31/713* (2006.01)
*A61K 48/00* (2006.01)
*A61K 31/712* (2006.01)

(52) U.S. Cl.
CPC .......... *C12N 15/113* (2013.01); *A61K 31/712* (2013.01); *A61K 31/713* (2013.01); *A61K 48/00* (2013.01); *C12N 2310/141* (2013.01); *C12N 2310/3231* (2013.01)

(58) Field of Classification Search
CPC ........................... C12N 15/113; A61K 31/713
See application file for complete search history.

(56) References Cited

U.S. PATENT DOCUMENTS

2007/0167387 A1   7/2007   Imanishi et al.
2011/0245481 A1   10/2011  Iba et al.

FOREIGN PATENT DOCUMENTS

| EP | 1661905 A1 | 5/2006 |
| EP | 2363467 A1 | 9/2011 |
| WO | 2005/021570 A1 | 3/2005 |
| WO | 2010/047216 A1 | 4/2010 |

OTHER PUBLICATIONS

Rahman et al., "Design, Synthesis, and Properties of 2',4'-BNA$^{NC}$: A Bridged Nucleic Acid Analogue," *J. Am. Chem. Soc.* 130:4886-4896 (2008).
Haraguchi et al., "Vectors expressing efficient RNA decoys achieve the long-term suppression of specific microRNA activity in mammalian cells," *Nucleic Acids Research* 37(6), 2009, 13 pages.
Hollensen et al., "Suppression of microRNAs by dual-targeting and clustered Tough Decoy inhibitors," *RNA Biology* 10(3):406-414, 2013.

*Primary Examiner* — Amy H Bowman
(74) *Attorney, Agent, or Firm* — Seed IP Law Group LLP

(57) ABSTRACT

The present invention pertains to the improvement of a miRNA inhibitor (a synthesized Tough Decoy (S-TuD)). The present invention provides a miRNA inhibitory complex including RNA or an analog thereof, wherein the RNA inhibitory complex includes at least one double-stranded structure and a miRNA binding sequence, each of two strands of the miRNA binding sequence being bound to two strands of at least one end of the double-stranded structure, and the miRNA inhibitory complex further includes at least one crosslinked nucleic acid.

18 Claims, 51 Drawing Sheets
Specification includes a Sequence Listing.

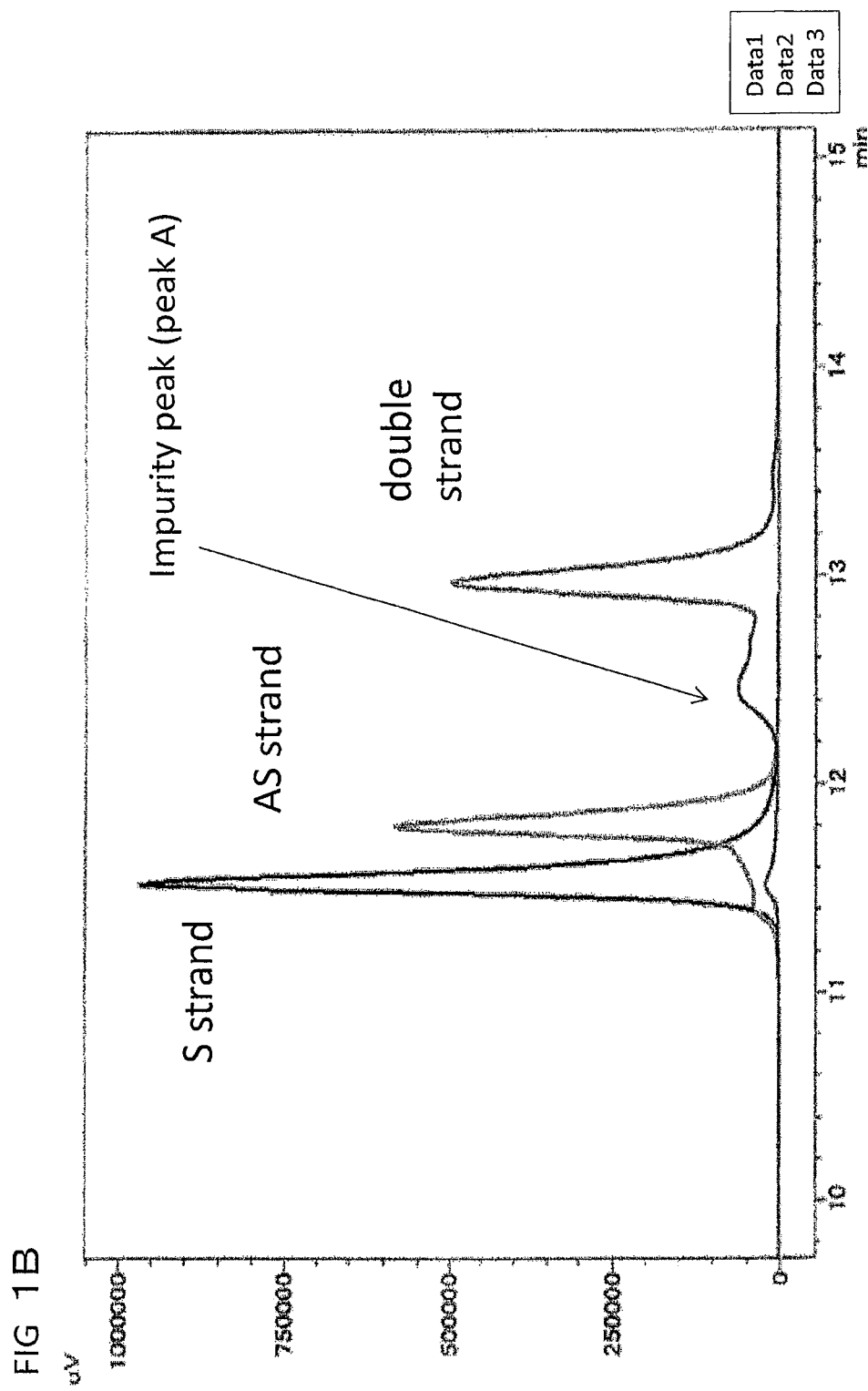

FIG. 2A

```
Original          AAACAAUGUGCAGACUACUGUAAA
                              18                  GUAUUCUGGU (SEQ ID NO: 1)
                  GACGGGCGCUAGGAUCAUC
                  CUGCCCGCGAUCCUAGUAG
                              24                  CAUAAGACCA (SEQ ID NO: 2)
                  AAAUGUCAUCAGACGUGUAACAAA (1) S-TuD199a-3p-1_18-pf-CU2F
                  AAACAAUGUGCAGACUACUGUAAA
                                                  GUAUUCUGGU (SEQ ID NO: 3)
                  GACGGGCGCUAGGAUCAUC
                  CUGCCCGCGAUCCUAGUAG
                                                  CAUAAGACCA (SEQ ID NO: 4)
                  AAAUGUCAUCAGACGUGUAACAAA (2) S-TuD199a-3p-1_18-pf-U4BNA
                  AAACAAUGUGCAGACUACUGUAAA
                                                  GUAUtCUGGt (SEQ ID NO: 5)
                  GACGGCGCtAGGAtCAUC
                  CUGCCGCGAUCCUaGUAG
                                                  CAUAAGACCA (SEQ ID NO: 6)
                  AAAUGUCAUCAGACGUGUAACAAA (3) S-TuD199a-3p-1_18-pf-U2BNA
                  AAACAAUGUGCAGACUACUGUAAA
                                                  GUAUUCUGGt (SEQ ID NO: 7)
                  GACGGCGCtAGGAUCAUC
                  CUGCCGCGAUCCtAGUAG
                                                  CAtAAGACCA (SEQ ID NO: 8)
                  AAAUGUCAUCAGACGUGUAACAAA (4) S-TuD199a-3p-1_18-pf-U4BNA-ds
                  AAACAAUGUGCAGACUACUGUAAA
                                                  GUAUtCUGGt (SEQ ID NO: 9)
                  GACGGCGCtAGGAtCAUC
                  CUGCCGCGaUCCUaGUAG
                                                  CAUAaGACCa (SEQ ID NO: 10)
                  AAAUGUCAUCAGACGUGUAACAAA (5) S-TuD199a-3p-1_18-pf-U4BNA_SI-8
                  AAACAAUGUGCAGACUACUGUAAA
                              t AGGAtCAUC         GUAUtCUGGt (SEQ ID NO: 11)
                              24
                              a UCCUaGUAG         CAUAaGACCa (SEQ ID NO: 12)
                  AAAUGUCAUCAGACGUGUAACAAA
                              10
```

BNANC(NMe): lower case
2'-Fluoro form: double underline

FIG. 2B (1)' S-TuD199a-3p-1_18-pf-S10
UAGGAUCAUC AAACAAUGUGCAGACUACUGUAAA GUAUUCUGGU (SEQ ID NO: 31)
AUCCUAGUAG AAAUGUCAUCAGACGUGUAACAAA CAUAAGACCA (SEQ ID NO: 32)

(1)" S-TuD199a-3p-1_18-pf-S10-BT4
tAGGAUCAUC AAACAAUGUGCAGACUACUGUAAA GUAUUCtGGU (SEQ ID NO: 65)
AUCCtAGUAG AAAUGUCAUCAGACGUGUAACAAA CAtAAGACCA (SEQ ID NO: 66)

(2)" S-TuD199a-3p-1_18-pf-S8-BT6
GGAUCAtC AAACAAUGUGCAGACUACUGUAAA GUAUtCtG (SEQ ID NO: 67)
CCtAGtAG AAAUGUCAUCAGACGUGUAACAAA CAtAAGAC (SEQ ID NO: 68)

(3)" S-TuD199a-3p-1_18-pf-S8-BT4
GGAUCAtC AAACAAUGUGCAGACUACUGUAAA GUAUUCtG (SEQ ID NO: 69)
CCtAGUAG AAAUGUCAUCAGACGUGUAACAAA CAtAAGAC (SEQ ID NO: 70)

(4)" S-TuD199a-3p-1_18-pf-S6-BT6
AtCAtC AAACAAUGUGCAGACUACUGUAAA GtAUtC (SEQ ID NO: 71)
UAGtAG AAAUGUCAUCAGACGUGUAACAAA CAtAAG (SEQ ID NO: 72)

(5)" S-TuD199a-3p-1_18-pf-S6-BT4
AtCAUC AAACAAUGUGCAGACUACUGUAAA GUAUtC (SEQ ID NO: 73)
UAGtAG AAAUGUCAUCAGACGUGUAACAAA CAtAAG (SEQ ID NO: 74)

BNANC(NMe): lower case

FIG. 4-2

Original

```
                            AAACAAUGUGCAGACUACUGUAAA
        GACGGCGCUAGGAUCAUC                              GUAUUCUGGU (SEQ ID NO: 1)

CUGCCGCGAUCCUAGUAG                              CAUAAGACCA (SEQ ID NO: 2)
                            AAAUGUCAUCAGACGUGUAACAAA
```

① S-TuD199a-3p-1_18-pf-CU2F

```
                            AAACAAUGUGCAGACUACUGUAAA
        GACGGCGCUAGGAUCAUC                              GUAUUCUGGU (SEQ ID NO: 3)

CUGCCGCGAUCCUAGUAG                              CAUAAGACCA (SEQ ID NO: 4)
                            AAAUGUCAUCAGACGUGUAACAAA
```

② S-TuD199a-3p-1_18-pf-U4BNA

```
                            AAACAAUGUGCAGACUACUGUAAA
        GACGGCGCt AGGAt CAUC                            GUAUt CUGGt (SEQ ID NO: 5)

CUGCCGCGAUCCUAGUAG                              CAUAAGACCA (SEQ ID NO: 6)
                            AAAUGUCAUCAGACGUGUAACAAA
```

③ S-TuD199a-3p-1_18-pf-U2BNA

```
                            AAACAAUGUGCAGACUACUGUAAA
        GACGGCGC t AGGAUCAUC                            GUAUUCUGGt (SEQ ID NO: 7)

CUGCCGCGAUCC t AGUAG                            CA t AAGACCA (SEQ ID NO: 8)
                            AAAUGUCAUCAGACGUGUAACAAA
```

④ S-TuD199a-3p-1_18-pf-U4BNA-ds

```
                            AAACAAUGUGCAGACUACUGUAAA
        GACGGCGC t AGGAtCAUC                            GUAUt CUGGt (SEQ ID NO: 9)

CUGCCGCGaUCCUaGUAG                              CAUAaGACCa (SEQ ID NO: 10)
                            AAAUGUCAUCAGACGUGUAACAAA
```

⑤ S-TuD199a-3p-1_18-pf-U4BNA_SI-8

```
                            AAACAAUGUGCAGACUACUGUAAA
                 t AGGAtCAUC                            GUAUt CUGGt (SEQ ID NO: 11)

a UCCUaGUAG                            CAUAaGACCa (SEQ ID NO: 12)
                            AAAUGUCAUCAGACGUGUAACAAA
```

BNANC(NMe): lower case, 2'-Fluoro form: double underline

S-TuD199a-3p

FIG. 6

Original
```
                AAACAAUGUGCAGACUACUGUAAA
    GACGGCGCUAGGAUCAUC         GUAUUCUGGU (SEQ ID NO: 1)
    CUGCCGCGAUCCUAGUAG         CAUAAGACCA (SEQ ID NO: 2)
                AAAUGUCAUCAGACGUGUAACAAA
```

⑯ S-TuD-miR-199a-3p-1_18-pf-L18B6-2
```
                AAACAAUGUGCAGACUACUGUAAA
    tACGGCGCUAGGAUCAUC         GtAUUCtGGA (SEQ ID NO: 13)
    AUGCCGCGAtCCUAGtAG         CAUAAGACCt (SEQ ID NO: 14)
                AAAUGUCAUCAGACGUGUAACAAA
```

㉒ S-TuD-miR-199a-3p-1_18-pf-L18B6-2-MBSB1 (complementary sequence to seed region includes BNA)
```
                AAACAAUGUGCAGACtACtGUAAA
    tACGGCGCUAGGAUCAUC         GtAUUCtGGA (SEQ ID NO: 15)
    AUGCCGCGAtCCUAGtAG         CAUAAGACCt (SEQ ID NO: 16)
                AAAUGtCAtCAGACGUGUAACAAA
```

㉓ S-TuD-miR-199a-3p-1_18-pf-L18B6-2-MBSB2 (complementary sequence to non-seed region includes BNA)
```
                AAACAaUGtGCAGACUACUGUAAA
    tACGGCGCUAGGAUCAUC         GtAUUCtGGA (SEQ ID NO: 17)
    AUGCCGCGAtCCUAGtAG         CAUAAGACCt (SEQ ID NO: 18)
                AAAUGUCAUCAGACGtGUaACAAA
```

㉔ S-TuD-miR-199a-3p-1_18-pf-L18B6-3-MBSB2 (complementary sequence to non-seed region includes BNA)
```
                AAACAaUGtGCAGACUACUGUAAA
    AtCGGCGCUAGGAUCAUC         GtAUUCUGAt (SEQ ID NO: 19)
    tAGCCGCGAtCCUAGtAG         CAUAAGACtA (SEQ ID NO: 20)
                AAAUGUCAUCAGACGtGUaACAAA
```

BNANC(NMe): lower case

FIG. 7

⑰ S-TuD199a-3p-1_18-pf-S10-BT6-MBSB1 (complementary sequence to seed region includes BNA)

AAACAAUGUGCAGACtACtGUAAA
tAGGAUCAUC                    GUAUtCUGGt (SEQ ID NO: 21)
AUCCtAGtAG                    CAtAAGACCA (SEQ ID NO: 22)
AAAUtCAtCAGACGUGUAACAAA

⑱ S-TuD199a-3p-1_18-pf-S10-BT6-MBSB2 (complementary sequence to non-seed region includes BNA)

AAACAaUGtGCAGACUACUGUAAA
tAGGAUCAUC                    GUAUtCUGGt (SEQ ID NO: 23)
AUCCtAGtAG                    CAtAAGACCA (SEQ ID NO: 24)
AAAUGUCAUCAGACGtGUaACAAA

BNANC(NMe): lower case, phosphorothioate structure: underline

㉓-① S-TuD-miR-199a-3p-1_18-pf-L18B6-2-PS1 (complementary sequence to non-seed region includes BNA)

AAACAaUGtGCAGACUACUGUAAA
tACGGGCUAGGAUCAUC                    GtAUUCtGGA (SEQ ID NO: 25)
AUGCCGCGAtCCUAGtAG                   CAUAAGACCt (SEQ ID NO: 26)
AAAUGUCAUCAGACGtGUaACAAA

㉓-② S-TuD-miR-199a-3p-1_18-pf-L18B6-2-PS2 (complementary sequence to non-seed region includes BNA)

AAACAaUGtGCAGACUACUGUAAA
<u>tACGGGCUAGGAUCAUC</u>                    <u>GtAUUCtGGA</u> (SEQ ID NO: 27)
<u>AUGCCGCGAtCCUAGtAG</u>                   <u>CAUAAGACCt</u> (SEQ ID NO: 28)
AAAUGUCAUCAGACGtGUaACAAA

㉓-③ S-TuD-miR-199a-3p-1_18-pf-L18B6-2-PS3 (complementary sequence to non-seed region includes BNA)

AAACAaUGtGCAGACUACUGUAAA
<u>tACGGGCUAGGAUCAUC</u>                    <u>GtAUUCtGGA</u> (SEQ ID NO: 29)
<u>AUGCCGCGAtCCUAGtAG</u>                   <u>CAUAAGACCt</u> (SEQ ID NO: 30)
AAAUGUCAUCAGACGtGUaACAAA

S-TuD199a-3p

FIG. 10

```
Original                              AAACAAUGUGCAGACUACUGUAAA
                                      GACGGGCGCUAGGAUCAUC       GUAUUCUGGU  (SEQ ID NO: 1)
                                      CUGCCCGCGAUCCUAGUAG       CAUAAGACCA  (SEQ ID NO: 2)
                                      AAAUGUCAUCAGACGUGUAACAAA ⑯ S-TuD-miR-199a-3p-1_18-pf-L18B6-2
                                      AAACAAUGUGCAGACUACUGUAAA
                                      tACGGGCGCUAGGAUCAUC       GtAUUCtGGA  (SEQ ID NO: 13)
                                      AUGCCCGCGAUCCUAGtAG       CAUAAGACCt  (SEQ ID NO: 14)
                                      AAAUGUCAUCAGACGUGUAACAAA ①' S-TuD199a-3p-1_18-pf-S10
                                      AAACAAUGUGCAGACUACUGUAAA
                                      UAGGAUCAUC                GUAUUCUGGU  (SEQ ID NO: 31)
                                      AUCCUAGUAG                CAUAAGACCA  (SEQ ID NO: 32)
                                      AAAUGUCAUCAGACGUGUAACAAA ⑥' S-TuD199a-3p-1_18-pf-S10-BT6
                                      AAACAAUGUGCAGACUACUGUAAA
                                      tAGGAUCAUC                GUAUtCUGGt  (SEQ ID NO: 33)
                                      AUCCtAGtAG                CAtAAGACCA  (SEQ ID NO: 34)
                                      AAAUGUCAUCAGACGUGUAACAAA ⑰ S-TuD199a-3p-1_18-pf-S10-BT6-MBSB1  (complementary sequence to seed region includes BNA)
                                      AAACAAUGUGCAGAtACtGUAAA
                                      tAGGAUCAUC                GUAUtCUGGt  (SEQ ID NO: 21)
                                      AUCCtAGtAG                CAtAAGACCA  (SEQ ID NO: 22)
                                      AAAUGtCAtCAGACGUGUAACAAA ⑱ S-TuD199a-3p-1_18-pf-S10-BT6-MBSB2  (complementary sequence to non-seed region includes BNA)
                                      AAACAaUGtGCAGACUACUGUAAA
                                      tAGGAUCAUC                GUAUtCUGGt  (SEQ ID NO: 23)
                                      AUCCtAGtAG                CAtAAGACCA  (SEQ ID NO: 24)
                                      AAAUGUCAUCAGACGtGUaACAAA
```

BNANC(NMe): lower case

FIG. 12

S-TuD199a-3p

```
Original       GACGGGCGCUAGGAUCAUC       AAACAAUGUGCAGACUACUGUAAA     GUAUUCUGGU  (SEQ ID NO: 1)
               CUGCCCGGCGAUCCUAGUAG                                   CAUAAGACCA  (SEQ ID NO: 2)
                                          AAAUGUCAUCAGACGUGUAACAAA
```

⑯ S-TuD-miR-199a-3p-1_18-pf-L18B6-2
```
               tACGGGCGCUAGGAUCAUC        AAACAAUGUGCAGACUACUGUAAA    GtAUUCtGGA  (SEQ ID NO: 13)
               AUGCCCGCGAtCCUAGtAG        AAAUGUCAUCAGACGUGUAACAAA    CAUAAGACCt  (SEQ ID NO: 14)
```

㉓ S-TuD-miR-199a-3p-1_18-pf-L18B6-2-MBSB2 (complementary sequence to non-seed region includes BNA)
```
               tACGGGCGCUAGGAUCAUC        AAACAaUGtGCAGACUACUGUAAA    GtAUUCtGGA  (SEQ ID NO: 35)
               AUGCCCGCGAtCCUAGtAG        AAAUGUCAUCAGACGtGUaACAAA    CAUAAGACCt  (SEQ ID NO: 36)
```

㉓-① S-TuD-miR-199a-3p-1_18-pf-L18B6-2-PS1 (complementary sequence to non-seed region includes BNA)
```
               tACGGGCGCUAGGAUCAUC        AAACAaUGtGCAGACUACUGUAAA    GtAUUCtGGA  (SEQ ID NO: 25)
               AUGCCCGCGAtCCUAGtAG        AAAUGUCAUCAGACGtGUaACAAA    CAUAAGACCt  (SEQ ID NO: 26)
```

㉓-② S-TuD-miR-199a-3p-1_18-pf-L18B6-2-PS2 (complementary sequence to non-seed region includes BNA)
```
               tACGGGCGCUAGGAUCAUC        AAACAaUGtGCAGACUACUGUAAA    GtAUUCtGGA  (SEQ ID NO: 27)
               AUGCCCGCGAtCCUAGtAG        AAAUGUCAUCAGACGtGUaACAAA    CAUAAGACCt  (SEQ ID NO: 28)
```

㉓-③ S-TuD-miR-199a-3p-1_18-pf-L18B6-2-PS3 (complementary sequence to non-seed region includes BNA)
```
               tACGGGCGCUAGGAUCAUC        AAACAaUGtGCAGACUACUGUAAA    GtAUUCtGGA  (SEQ ID NO: 29)
               AUGCCCGCGAtCCUAGtAG        AAAUGUCAUCAGACGtGUaACAAA    CAUAAGACCt  (SEQ ID NO: 30)
```

BNANC(NMe): lower case
Phosphorothioate structure: underline

S-TuD199a-3p

FIG. 13

① S-TuD199a-3p-1_18-pf-S10

```
   AAACAAUGUGCAGACUACUGUAAA
UAGGAUCAUC                GUAUUCUGGU  (SEQ ID NO: 31)
AUCCUAGUAG                CAUAAGACCA  (SEQ ID NO: 32)
   AAAUGUCAUCAGACGUGUAACAAA
```

⑥ S-TuD199a-3p-1_18-pf-S10-BT6

```
   AAACAAUGUGCAGACUACUGUAAA
tAGGAUCAUC                GUAUtCUGGt  (SEQ ID NO: 33)
AUCCtAGtAG                CAtAAGACCA  (SEQ ID NO: 34)
   AAAUGUCAUCAGACGUGUAACAAA
```

⑰ S-TuD199a-3p-1_18-pf-S10-BT6-MBSB1 (complementary sequence to seed region includes BNA)

```
   AAACAAUGUGCAGACtACtGUAAA
tAGGAUCAUC                GUAUtCUGGt  (SEQ ID NO: 21)
AUCCtAGtAG                CAtAAGACCA  (SEQ ID NO: 22)
   AAAUGtCAtCAGACGUGUAACAAA
```

⑱ S-TuD199a-3p-1_18-pf-S10-BT6-MBSB2 (complementary sequence to non-seed region includes BNA)

```
   AAACAaUGtGCAGACUACUGUAAA
tAGGAUCAUC                GUAUtCUGGt  (SEQ ID NO: 23)
AUCCtAGtAG                CAtAAGACCA  (SEQ ID NO: 24)
   AAAUGUCAUCAGACGtGUaACAAA
```

BNANC(NMe): lower case

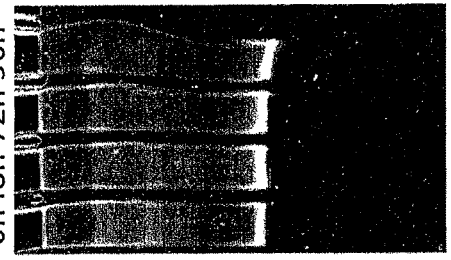
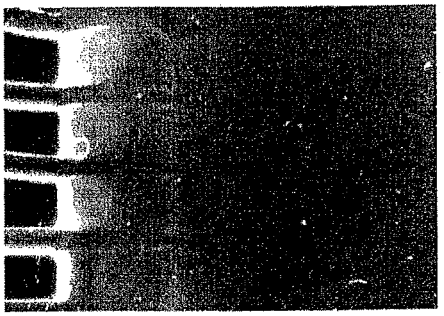
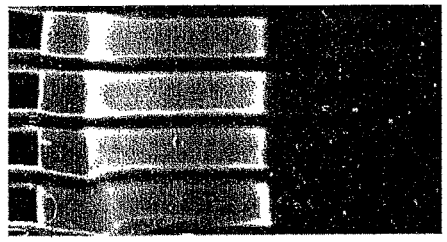
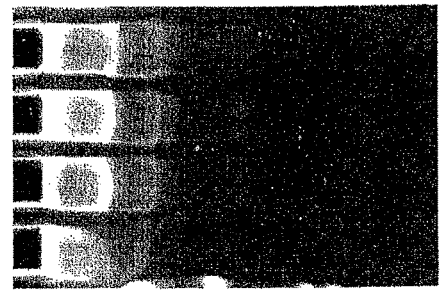
FIG. 14

Short type
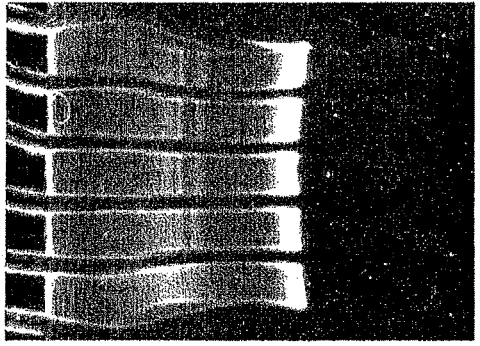
①′ S-TuD199a-3p-1_18-pf-S10
0h 24h 48h 72h 96h
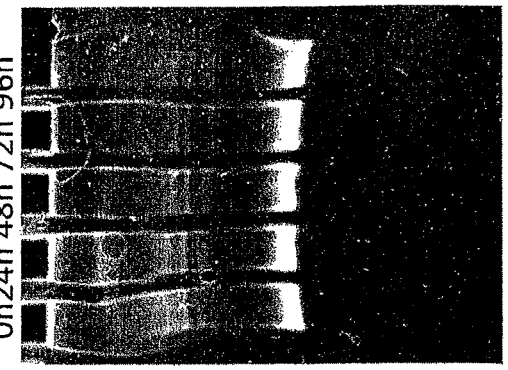
⑥′ S-TuD199a-3p-1_18-pf-S10-BT6
0h 24h 48h 72h 96h
FIG. 15
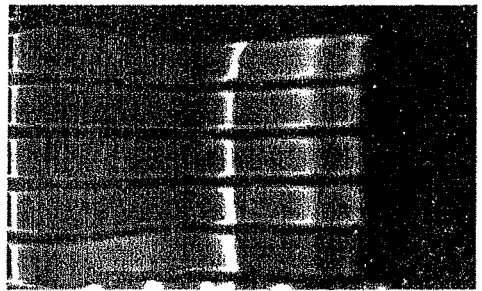
⑰ S-TuD199a-3p-1_18-pf-S10-BT6-MBSB1
0h 24h 48h 72h 96h
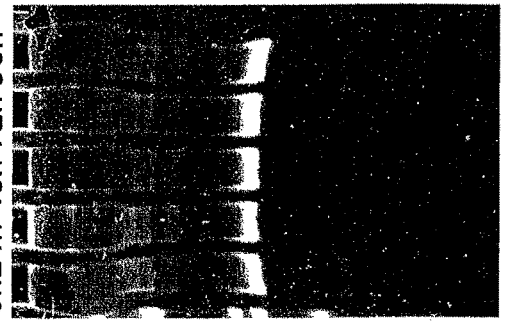
⑱ S-TuD199a-3p-1_18-pf-S10-BT6-MBSB2
0h 24h 48h 72h 96h Luciferase reporter vector
Oligo was inserted in XbaI-NotI site psiCHECK2-T200c-3p-s
5'-TCGAGTCCATCATTACCCGGCAGTATTAGC-3' (SEQ ID NO: 75)

psiCHECK2-T200c-3p-a
5'-GGCCGCTAATACTGCCGGGTAATGATGGAC-3' (SEQ ID NO: 76)

psiCHECK2-T199a-3px3-s
5'-TCGAGTAACCAATGTGCAGACTACTGTATAACCAATGTGCAGACTACTGTATA
ACCAATGTGCAGACTACTGTGC-3' (SEQ ID NO: 77)

psiCHECK2-T199a-3px3-a
5'-GGCCGCACAGTAGTCTGCACATTGGTTATACAGTAGTCTGCACATTGGTTATA
CAGTAGTCTGCACATTGGTTAC-3' (SEQ ID NO: 78)

psiCHECK2-T21-5p-s
5'-TCGAGTCAACATCAGTCTGATAAGCTAGC-3' (SEQ ID NO: 79)

psiCHECK2-T21-5p-a
5'-GGCCGCTAGCTTATCAGACTGATGTTGAC-3' (SEQ ID NO: 80)

FIG. 17

S-TuD-NC2

FIG. 18

GACGGCGCUAGGAUCAUC AACUAUCGGAGUAUCGACGUCGAGGCCCAA GUAUUCUGGU (SEQ ID NO: 57)
CUGCCGGAUCCUAGUAG AACCCGGAGCUGCAGCUAUGAGCGCUAUCAA CAUAAGACCA (SEQ ID NO: 58)

S-TuD200c

㊶ S-TuD-200c-1_22-pf

```
              AACCCAUCAUUACCCGGCAGUAUUACAA
UACGGGCGCUAGGAUCAUC                         GUAUUCUGGA  (SEQ ID NO: 37)
AUGCCCGCGAUCCUAGUAG                         CAUAAGACCU  (SEQ ID NO: 38)
              AACAUUAUGACGGCCCAUUACUACCCAA
```

㊷ S-TuD-200c-1_22-pf-L18B6

```
              AACCCAUCAUUACCCGGCAGUAUUACAA
tACGGGCGCUAGGAUCAUC                         GtAUUCtGGA  (SEQ ID NO: 39)
AUGCCCGCGAtCCUAGtAG                         CAUAAGACCt  (SEQ ID NO: 40)
              AACAUUAUGACGGCCCAUUACUACCCAA
```

㊸ S-TuD-200c-1_22-pf-L18B6-MBSB1 (complementary sequence to seed region includes BNA)

```
              AACCCAUCAUUACCCGGCAGtAUtACAA
tACGGGCGCUAGGAUCAUC                         GtAUUCtGGA  (SEQ ID NO: 41)
AUGCCCGCGAtCCUAGtAG                         CAUAAGACCt  (SEQ ID NO: 42)
              AACAtUAtGACGGCCCAUUACUACCCAA
```

㊹ S-TuD-200c-1_22-pf-L18B6-MBSB2 (complementary sequence to non-seed region includes BNA)

```
              AACCCAUCAUtACCCGGCAGUAUUACAA
tACGGGCGCUAGGAUCAUC                         GtAUUCtGGA  (SEQ ID NO: 43)
AUGCCCGCGAtCCUAGtAG                         CAUAAGACCt  (SEQ ID NO: 44)
              AACAUUAUGACGGCCcAUtACUACCCAA
```

㊺ S-TuD-200c-1_22-pf-S10-BT6-MBSB2 (complementary sequence to non-seed region includes BNA)

```
              AACCCAUCAtUACCCGGCAGUAUUACAA
tAGGAUCAUC                                  GUAUtCUGGt  (SEQ ID NO: 45)
AUCCtAGtAG                                  CAtAAGACCA  (SEQ ID NO: 46)
              AACAUUAUGACGGCCcAUtACUACCCAA
```

BNANC(NMe): lower case

FIG. 19

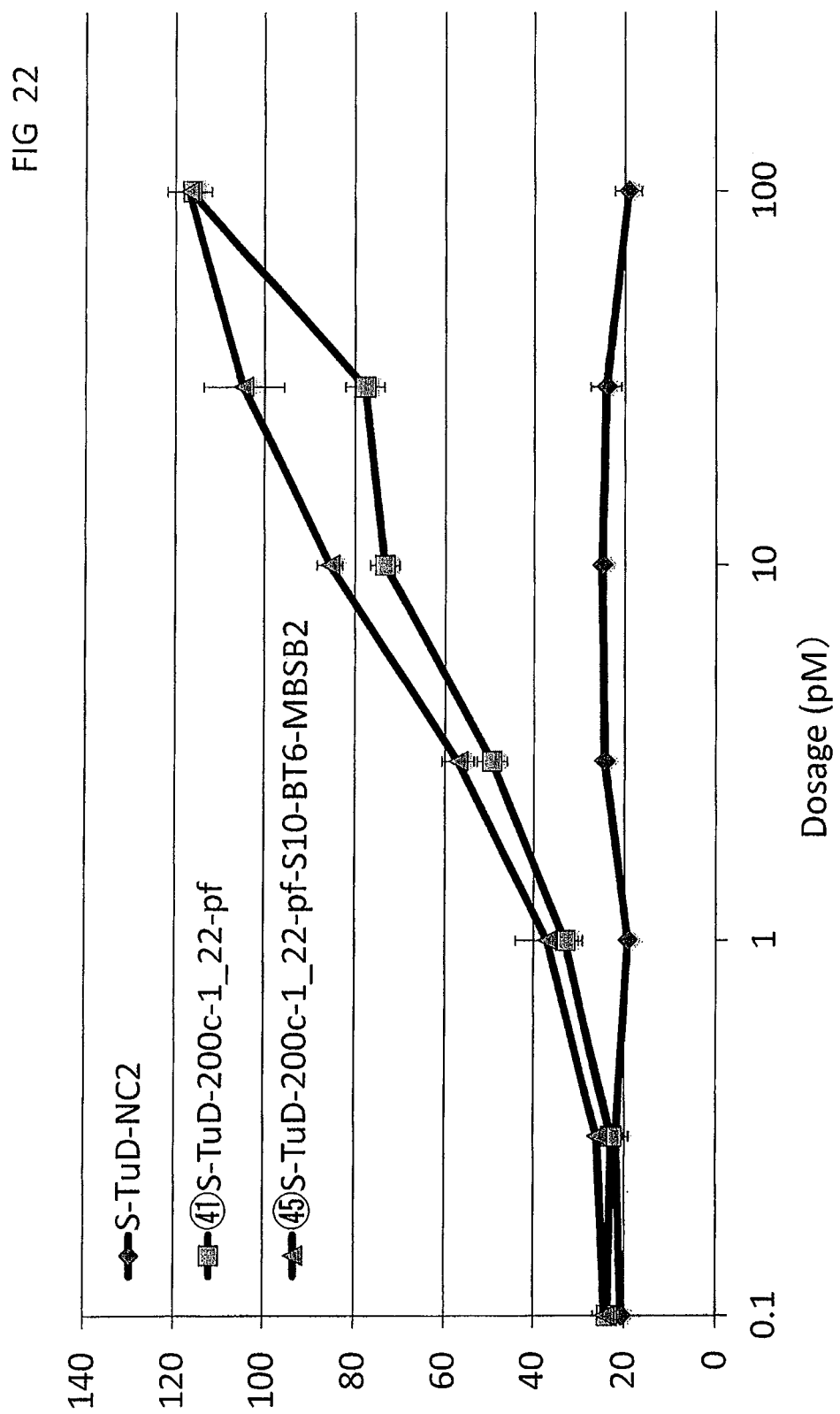

S-TuD21

FIG. 23

(51) S-TuD-21-1_17-10mut

```
                 AACAUCAGUCGGAUAAGCUACAA
UACGGGCGCUAGGAUCAUC                    GUAUUCUGGA  (SEQ ID NO: 47)
AUGCCCGCGAUCCUAGUAG                    CAUAAGACCU  (SEQ ID NO: 48)
                 AACAUCGAAUAGGCUGACUACAA
```

(52) S-TuD-21-1_17-10mut-L18B6

```
                 AACAUCAGUCGGAUAAGCUACAA
tACGGGCGCUAGGAUCAUC                    GtAUUCtGGA  (SEQ ID NO: 49)
AUGCCCGCGAtCCUAGtAG                    CAUAAGACCt  (SEQ ID NO: 50)
                 AACAUCGAAUAGGCUGACUACAA
```

(53) S-TuD-21-1_17-10mut-L18B6-MBSB1

```
                 AACAtCAgUCGGAUAAGCUACAA
tACGGGCGCUAGGAUCAUC                    GtAUUCtGGA  (SEQ ID NO: 51)
AUGCCCGCGAtCCUAGtAG                    CAUAAGACCt  (SEQ ID NO: 52)
                 AACAUCGAAUAGGCUgACtACAA
```

(54) S-TuD-21-1_17-10mut-S10-BT6

```
                 AACAUCAGUCGGAUAAGCUACAA
tAGGAUCAUC                             GUAUtCUGGt  (SEQ ID NO: 53)
AUCCtAGtAG                             CAtAAGACCA  (SEQ ID NO: 54)
                 AACAUCGAAUAGGCUGACUACAA
```

(55) S-TuD-21-1_17-10mut-S10-BT6-MBSB1

```
                 AACAtCAgUCGGAUAAGCUACAA
tAGGAUCAUC                             GUAUtCUGGt  (SEQ ID NO: 55)
AUCCtAGtAG                             CAtAAGACCA  (SEQ ID NO: 56)
                 AACAUCGAAUAGGCUgACtACAA
```

BNANC(NMe): lower case

FIG. 27

(51) S-TuD-21-1_17-10mut

UACGGGCUAGGAUCAUC    AACAUCAGUCGGAUAAGCUACAA    GUAUUCUGGA (SEQ ID NO: 47)
AUGCCGGCGAUCCUAGUAG                                              CAUAAGACCU (SEQ ID NO: 48)
                            AACAUCGAAUAGGCUGACUACAA

(53) S-TuD-21-1_17-10mut-L18B6-MBSB1 tACGGGCUAGGAUCAUC    AACAtCAgUCGGAUAAGCUACAA    GtAUUCtGGA (SEQ ID NO: 51)
AUGCCGGCGAtCCUAGtAG                                              CAUAAGACCt (SEQ ID NO: 52)
                            AACAUCGAAUAGGCUgActACAA

(55) S-TuD-21-1_17-10mut-S10-BT6-MBSB1 tAGGAUCAUC    AACAtCAgUCGGAUAAGCUACAA    GUAUtCUGGt (SEQ ID NO: 55)
AUCCtAGtAG                                                CAtAAGACCA (SEQ ID NO: 56)
                  AACAUCGAAUAGGCUgActACAA

BNANC(NMe): lower case

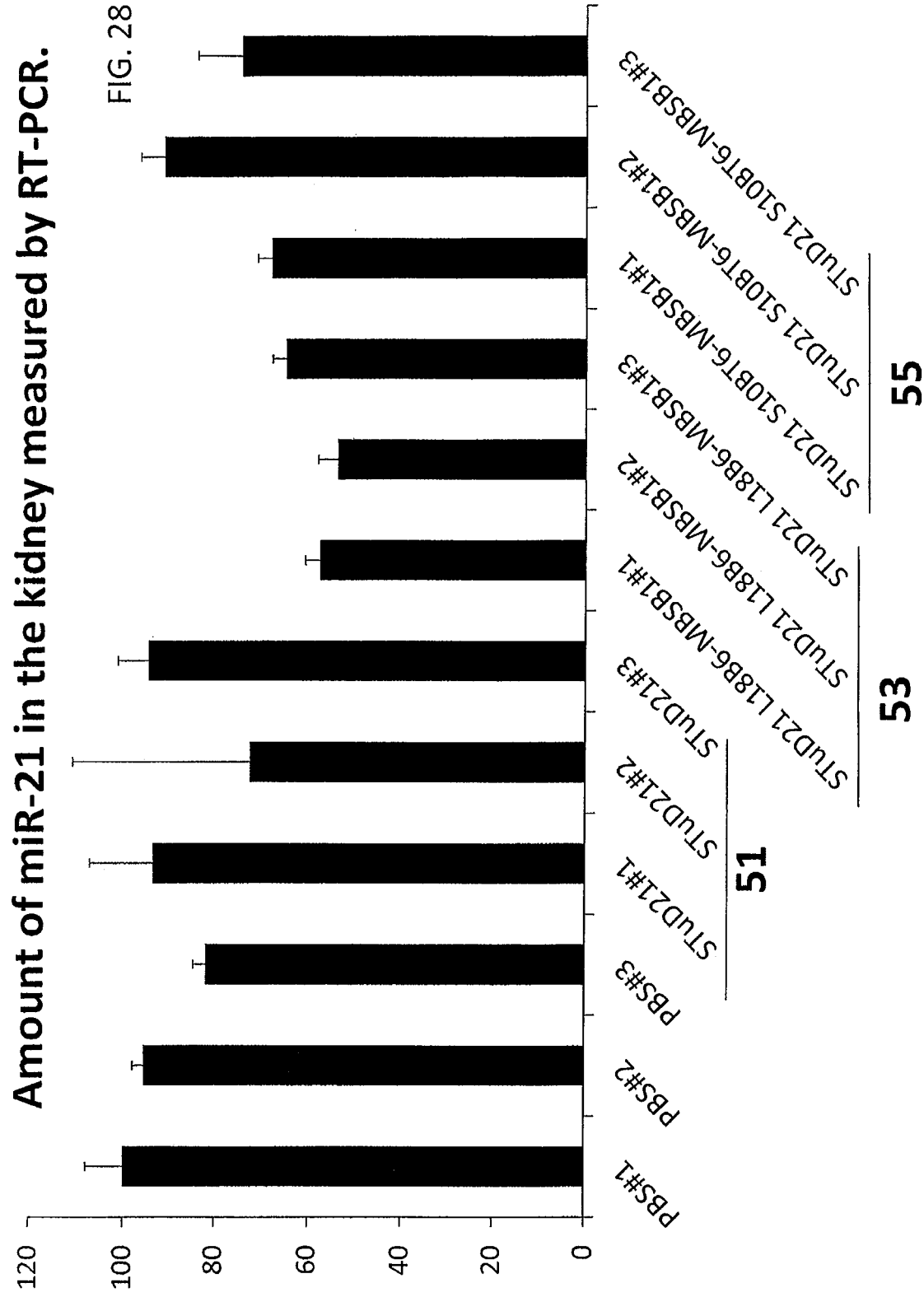

FIG. 32

Original

```
       GACGGCGCUAGGAUCAUC                         AAACAAUGUGCAGACUACUGUAAA
                          GUAUUCUGGU  (SEQ ID NO: 1)
       CUGCCGCGAUCCUAGUAG                         AAAUGUCAUCAGACGUGUAACAAA
                          CAUAAGACCA  (SEQ ID NO: 2)
```

S-TuD prepared first

⑤ S-TuD199a-3p-1_18-pf-U4BNA_SI-8

```
       tAGGAtCAUC                         AAACAAUGUGCAGACUACUGUAAA
                  GUAUtCUGGt  (SEQ ID NO: 11)
       aUCCUaGUAG                         AAAUGUCAUCAGACGUGUAACAAA
                  CAUAaGACCa  (SEQ ID NO: 12)
```

S-TuD prepared second

① S-TuD199a-3p-1_18-pf-S10

```
                   AAACAAUGUGCAGACUACUGUAAA
       UAGGAUCAUC                         GUAUUCUGGU  (SEQ ID NO: 31)
       AUCCUAGUAG                         CAUAAGACCA  (SEQ ID NO: 32)
                   AAAUGUCAUCAGACGUGUAACAAA
```

② S-TuD199a-3p-1_18-pf-S10-BT8

```
                   AAACAAUGUGCAGACUACUGUAAA
       tAGGAtCAUC                         GUAUtCtGGt  (SEQ ID NO: 59)
       AtCCUaGtAG                         CAtAAGACCA  (SEQ ID NO: 60)
                   AAAUGUCAUCAGACGUGUAACAAA
```

⑥ S-TuD199a-3p-1_18-pf-S10-BT6

```
                   AAACAAUGUGCAGACUACUGUAAA
       tAGGAUCAUC                         GUAUtCUGGt  (SEQ ID NO: 33)
       AUCCtAGUAG                         CAUAAGACCA  (SEQ ID NO: 34)
                   AAAUGUCAUCAGACGUGUAACAAA
```

⑦ S-TuD199a-3p-1_18-pf-S10-LT6

```
                   AAACAAUGUGCAGACUACUGUAAA
       <u>T</u>AGGAUCAUC                         GUAU<u>T</u>CUGG<u>T</u>  (SEQ ID NO: 61)
       AUCC<u>T</u>AG<u>T</u>AG                         CA<u>T</u>AAGACCA  (SEQ ID NO: 62)
                   AAAUGUCAUCAGACGUGUAACAAA
```

⑧ S-TuD199a-3p-1_18-pf-S10-BT12

```
                   AAACAAUGUGCAGACUACUGUAAA
       tAGGAtCAtC                         GtAttCtGGt  (SEQ ID NO: 63)
       AtCCtAGtAG                         CAtAAGACCA  (SEQ ID NO: 64)
                   AAAUGUCAUCAGACGUGUAACAAA
```

BNANC(NMe): lower case
LNA: slanted double underline

Original
```
GACGGCGCUAGGAUCAUC AAACAAUGUGCAGACUACUGUAAA GUAUUCUGGU (SEQ ID NO: 1)
CUGCCGCGAUCCUAGUAG                              CAUAAGACCA (SEQ ID NO: 2)
                   AAAUGUCAUCAGACGUGUAACAAA
```

S-TuD prepared second

⑥′ S-TuD199a-3p-1_18-pf-S10-BT6
```
                   AAACAAUGUGCAGACUACUGUAAA
tAGGAUCAUC                                   GUAUtCUGGt (SEQ ID NO: 33)
AUCCtAGtAG                                   CAtAAGACCA (SEQ ID NO: 34)
                   AAAUGUCAUCAGACGUGUAACAAA
```

S-TuD prepared third

①″ S-TuD199a-3p-1_18-pf-S10-BT4
```
                   AAACAAUGUGCAGACUACUGUAAA
tAGGAUCAUC                                   GUAUUCtGGU (SEQ ID NO: 65)
AUCCtAGUAG                                   CAtAAGACCA (SEQ ID NO: 66)
                   AAAUGUCAUCAGACGUGUAACAAA
```

②″ S-TuD199a-3p-1_18-pf-S8-BT6
```
                   AAACAAUGUGCAGACUACUGUAAA
GGAUCAtC                                     GUAUtCtG (SEQ ID NO: 67)
CCtAGtAG                                     CAtAAGAC (SEQ ID NO: 68)
                   AAAUGUCAUCAGACGUGUAACAAA
```

③″ S-TuD199a-3p-1_18-pf-S8-BT4
```
                   AAACAAUGUGCAGACUACUGUAAA
GGAUCAtC                                     GUAUUCtG (SEQ ID NO: 69)
CCtAGUAG                                     CAtAAGAC (SEQ ID NO: 70)
                   AAAUGUCAUCAGACGUGUAACAAA
```

④″ S-TuD199a-3p-1_18-pf-S6-BT6
```
                   AAACAAUGUGCAGACUACUGUAAA
AtCAtC                                       GtAUtC (SEQ ID NO: 71)
UAGtAG                                       CAtAAG (SEQ ID NO: 72)
                   AAAUGUCAUCAGACGUGUAACAAA
```

⑤″ S-TuD199a-3p-1_18-pf-S6-BT4
```
                   AAACAAUGUGCAGACUACUGUAAA
AtCAUC                                       GUAUtC (SEQ ID NO: 73)
UAGtAG                                       CAtAAG (SEQ ID NO: 74)
                   AAAUGUCAUCAGACGUGUAACAAA
```

BNANC(NMe): lower case

FIG. 36

Overall evaluation of modified S-TuDs prepared thus far

```
Original
                    AAACAAUGUGCAGACUACUGUAAA
        GACGGCGCUAGGAUCAUC          GUAUUCUGGU    (SEQ ID NO: 1)
        CUGCCGCGAUCCUAGUAG          CAUAAGACCA    (SEQ ID NO: 2)
                    AAAUGUCAUCAGACGUGUAACAAA ④ S-TuD-miR-199a-3p-1_18-pf-U4BNA-ds
                    AAACAAUGUGCAGACUACUGUAAA
        GACGGCGCtAGGAtCAUC          GUAUtCUGGt    (SEQ ID NO: 9)
        CUGCCGCGaUCCUaGUAG          CAUAaGACCa    (SEQ ID NO: 10)
                    AAAUGUCAUCAGACGUGUAACAAA ①' S-TuD199a-3p-1_18-pf-S10
                    AAACAAUGUGCAGACUACUGUAAA
        UAGGAUCAUC                  GUAUUCUGGU    (SEQ ID NO: 31)
        AUCCUAGUAG                  CAUAAGACCA    (SEQ ID NO: 32)
                    AAAUGUCAUCAGACGUGUAACAAA ②' S-TuD199a-3p-1_18-pf-S10-BT8
                    AAACAAUGUGCAGACUACUGUAAA
        tAGGAtCAUC                  GUAUtCtGGt    (SEQ ID NO: 59)
        AtCCUAGtAG                  CAtAAGACCA    (SEQ ID NO: 60)
                    AAAUGUCAUCAGACGUGUAACAAA ⑥' S-TuD199a-3p-1_18-pf-S10-BT6
                    AAACAAUGUGCAGACUACUGUAAA
        tAGGAUCAUC                  GUAUtCUGGt    (SEQ ID NO: 33)
        AUCCtAGtAG                  CAtAAGACCA    (SEQ ID NO: 34)
                    AAAUGUCAUCAGACGUGUAACAAA ①" S-TuD199a-3p-1_18-pf-S10-BT4
                    AAACAAUGUGCAGACUACUGUAAA
        tAGGAUCAUC                  GUAUUCtGGU    (SEQ ID NO: 65)
        AUCCtAGUAG                  CAtAAGACCA    (SEQ ID NO: 66)
                    AAAUGUCAUCAGACGUGUAACAAA
```

BNANC(NMe): lower case

Fig 38
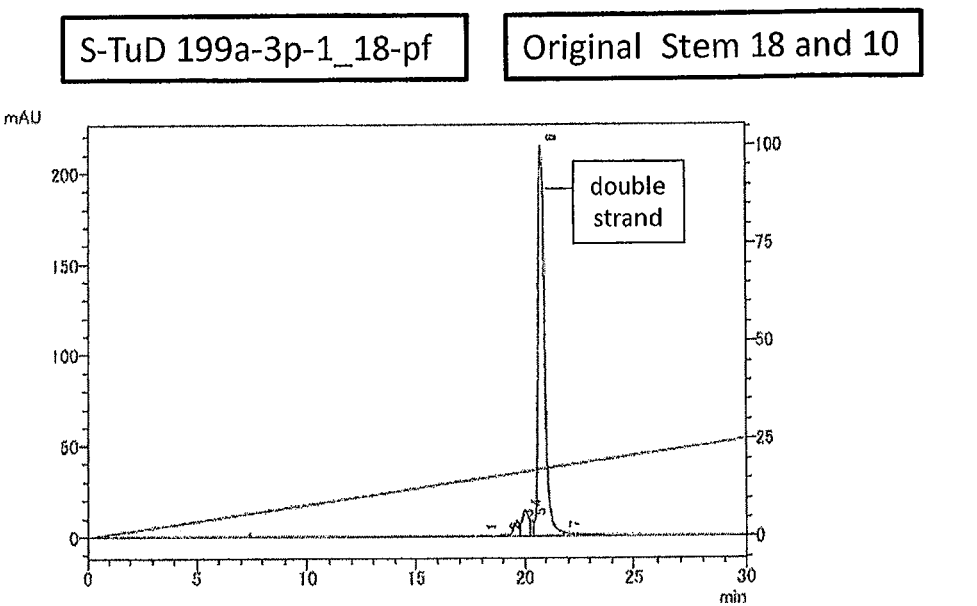
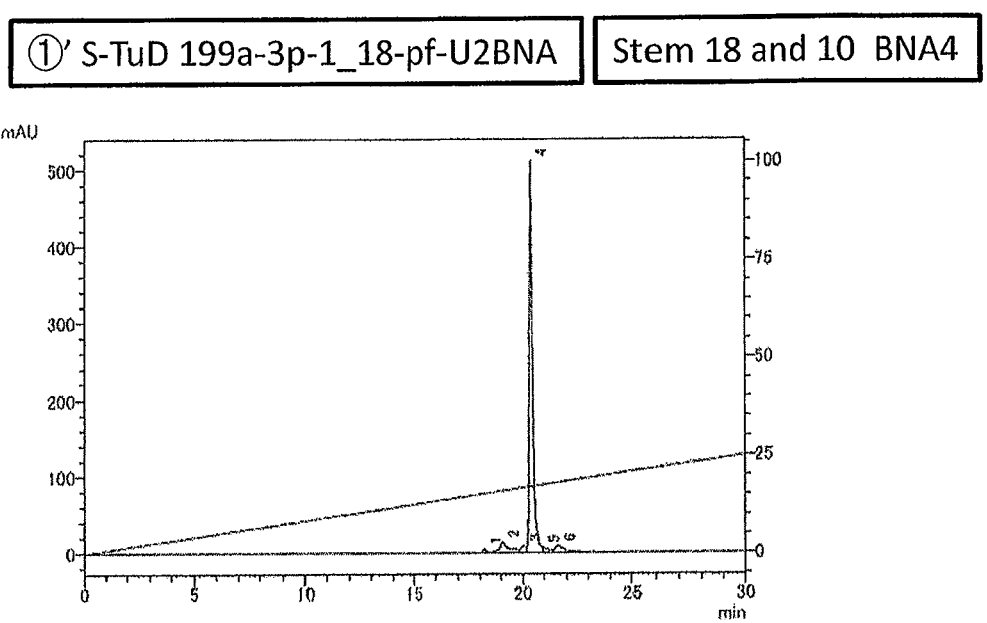

Fig 40
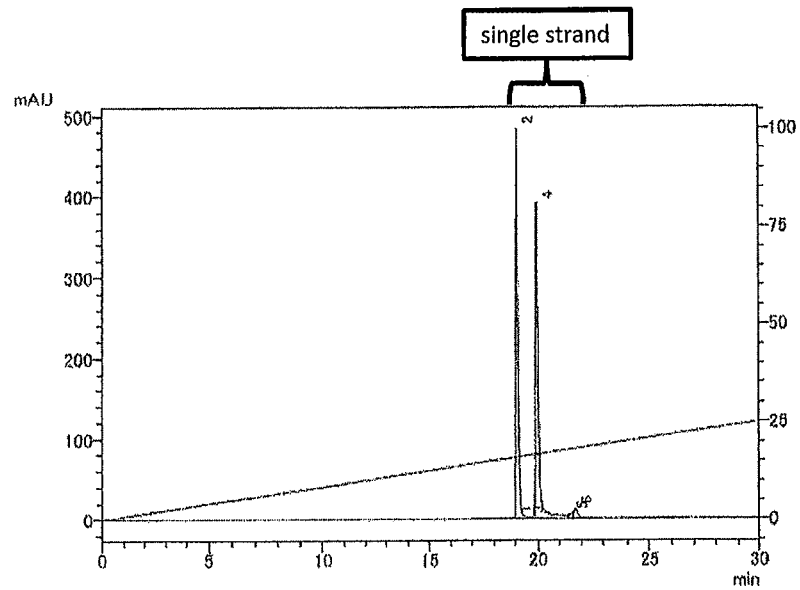
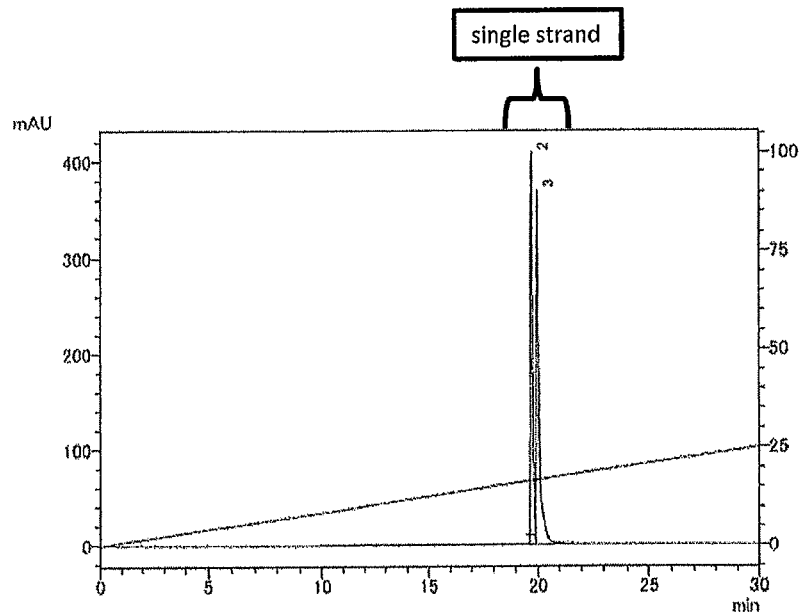

SEQUENCE LISTING

```
<160> NUMBER OF SEQ ID NOS: 80

<210> SEQ ID NO 1
<211> LENGTH: 52
<212> TYPE: DNA
<213> ORGANISM: artificial sequence
<220> FEATURE:
<223> OTHER INFORMATION: original sense sequence
<220> FEATURE:
<221> NAME/KEY: 2'-OMe
<222> LOCATION: (1)..(52)

<400> SEQUENCE: 1
gacggcgcua ggaucaucaa acaaugugca gacuacugua aaguauucug gu          52

<210> SEQ ID NO 2
<211> LENGTH: 52
<212> TYPE: DNA
<213> ORGANISM: artificial sequence
<220> FEATURE:
<223> OTHER INFORMATION: original antisense sequence
<220> FEATURE:
<221> NAME/KEY: 2'-OMe
<222> LOCATION: (1)..(52)

<400> SEQUENCE: 2
accagaauac uuuacaaugug cagacuacug uaaagaugau ccuagcgccg uc          52

<210> SEQ ID NO 3
<211> LENGTH: 52
<212> TYPE: DNA
<213> ORGANISM: artificial sequence
<220> FEATURE:
<223> OTHER INFORMATION: sense sequence (1)
<220> FEATURE:
<221> NAME/KEY: 2'-OMe
<222> LOCATION: (1)..(2)
<220> FEATURE:
<221> NAME/KEY: 2'-F
<222> LOCATION: (3)..(3)
<220> FEATURE:
<221> NAME/KEY: 2'-OMe
```

-continued

```
<222> LOCATION: (4)..(5)
<220> FEATURE:
<221> NAME/KEY: 2'-F
<222> LOCATION: (6)..(6)
<220> FEATURE:
<221> NAME/KEY: 2'-OMe
<222> LOCATION: (7)..(7)
<220> FEATURE:
<221> NAME/KEY: 2'-F
<222> LOCATION: (8)..(9)
<220> FEATURE:
<221> NAME/KEY: 2'-OMe
<222> LOCATION: (10)..(13)
<220> FEATURE:
<221> NAME/KEY: 2'-F
<222> LOCATION: (14)..(15)
<220> FEATURE:
<221> NAME/KEY: 2'-OMe
<222> LOCATION: (16)..(16)
<220> FEATURE:
<221> NAME/KEY: 2'-F
<222> LOCATION: (17)..(18)
<220> FEATURE:
<221> NAME/KEY: 2'-OMe
<222> LOCATION: (19)..(21)
<220> FEATURE:
<221> NAME/KEY: 2'-F
<222> LOCATION: (22)..(22)
<220> FEATURE:
<221> NAME/KEY: 2'-OMe
<222> LOCATION: (23)..(24)
<220> FEATURE:
<221> NAME/KEY: 2'-F
<222> LOCATION: (25)..(25)
<220> FEATURE:
<221> NAME/KEY: 2'-OMe
<222> LOCATION: (26)..(26)
<220> FEATURE:
<221> NAME/KEY: 2'-F
<222> LOCATION: (27)..(27)
<220> FEATURE:
<221> NAME/KEY: 2'-OMe
<222> LOCATION: (28)..(28)
<220> FEATURE:
<221> NAME/KEY: 2'-F
<222> LOCATION: (29)..(29)
<220> FEATURE:
<221> NAME/KEY: 2'-OMe
<222> LOCATION: (30)..(32)
<220> FEATURE:
<221> NAME/KEY: 2'-F
<222> LOCATION: (33)..(34)
<220> FEATURE:
<221> NAME/KEY: 2'-OMe
<222> LOCATION: (35)..(35)
<220> FEATURE:
<221> NAME/KEY: 2'-F
<222> LOCATION: (36)..(37)
<220> FEATURE:
<221> NAME/KEY: 2'-OMe
<222> LOCATION: (38)..(38)
<220> FEATURE:
<221> NAME/KEY: 2'-F
<222> LOCATION: (39)..(39)
<220> FEATURE:
<221> NAME/KEY: 2'-OMe
<222> LOCATION: (40)..(43)
<220> FEATURE:
<221> NAME/KEY: 2'-F
<222> LOCATION: (44)..(44)
<220> FEATURE:
<221> NAME/KEY: 2'-OMe
<222> LOCATION: (45)..(45)
<220> FEATURE:
<221> NAME/KEY: 2'-F
<222> LOCATION: (46)..(49)
<220> FEATURE:
<221> NAME/KEY: 2'-OMe
<222> LOCATION: (50)..(51)
```

-continued

```
<220> FEATURE:
<221> NAME/KEY: 2'-F
<222> LOCATION: (52)..(52)

<400> SEQUENCE: 3
gacggcgcua ggaucaucaa acaaugugca gacuacugua aaguauucug gu            52

<210> SEQ ID NO 4
<211> LENGTH: 52
<212> TYPE: DNA
<213> ORGANISM: artificial sequence
<220> FEATURE:
<223> OTHER INFORMATION: antisense sequence (1)
<220> FEATURE:
<221> NAME/KEY: 2'-OMe
<222> LOCATION: (1)..(1)
<220> FEATURE:
<221> NAME/KEY: 2'-F
<222> LOCATION: (2)..(3)
<220> FEATURE:
<221> NAME/KEY: 2'-OMe
<222> LOCATION: (4)..(7)
<220> FEATURE:
<221> NAME/KEY: 2'-F
<222> LOCATION: (8)..(8)
<220> FEATURE:
<221> NAME/KEY: 2'-OMe
<222> LOCATION: (9)..(9)
<220> FEATURE:
<221> NAME/KEY: 2'-F
<222> LOCATION: (10)..(10)
<220> FEATURE:
<221> NAME/KEY: 2'-OMe
<222> LOCATION: (11)..(13)
<220> FEATURE:
<221> NAME/KEY: 2'-F
<222> LOCATION: (14)..(14)
<220> FEATURE:
<221> NAME/KEY: 2'-OMe
<222> LOCATION: (15)..(16)
<220> FEATURE:
<221> NAME/KEY: 2'-F
<222> LOCATION: (17)..(17)
<220> FEATURE:
<221> NAME/KEY: 2'-OMe
<222> LOCATION: (18)..(18)
<220> FEATURE:
<221> NAME/KEY: 2'-F
<222> LOCATION: (19)..(19)
<220> FEATURE:
<221> NAME/KEY: 2'-OMe
<222> LOCATION: (20)..(20)
<220> FEATURE:
<221> NAME/KEY: 2'-F
<222> LOCATION: (21)..(21)
<220> FEATURE:
<221> NAME/KEY: 2'-OMe
<222> LOCATION: (22)..(24)
<220> FEATURE:
<221> NAME/KEY: 2'-F
<222> LOCATION: (25)..(26)
<220> FEATURE:
<221> NAME/KEY: 2'-OMe
<222> LOCATION: (27)..(27)
<220> FEATURE:
<221> NAME/KEY: 2'-F
<222> LOCATION: (28)..(29)
<220> FEATURE:
<221> NAME/KEY: 2'-OMe
<222> LOCATION: (30)..(30)
<220> FEATURE:
<221> NAME/KEY: 2'-F
<222> LOCATION: (31)..(31)
<220> FEATURE:
<221> NAME/KEY: 2'-OMe
<222> LOCATION: (32)..(36)
<220> FEATURE:
```

```
<221> NAME/KEY: 2'-F
<222> LOCATION: (37)..(37)
<220> FEATURE:
<221> NAME/KEY: 2'-OMe
<222> LOCATION: (38)..(39)
<220> FEATURE:
<221> NAME/KEY: 2'-F
<222> LOCATION: (40)..(43)
<220> FEATURE:
<221> NAME/KEY: 2'-OMe
<222> LOCATION: (44)..(45)
<220> FEATURE:
<221> NAME/KEY: 2'-F
<222> LOCATION: (46)..(46)
<220> FEATURE:
<221> NAME/KEY: 2'-OMe
<222> LOCATION: (47)..(47)
<220> FEATURE:
<221> NAME/KEY: 2'-F
<222> LOCATION: (48)..(49)
<220> FEATURE:
<221> NAME/KEY: 2'-OMe
<222> LOCATION: (50)..(50)
<220> FEATURE:
<221> NAME/KEY: 2'-F
<222> LOCATION: (51)..(52)

<400> SEQUENCE: 4
accagaauac aaacaaugug cagacuacug uaaagaugau ccuagcgccg uc              52

<210> SEQ ID NO 5
<211> LENGTH: 52
<212> TYPE: DNA
<213> ORGANISM: artificial sequence
<220> FEATURE:
<223> OTHER INFORMATION: sense sequence (2)
<220> FEATURE:
<221> NAME/KEY: 2'-OMe
<222> LOCATION: (1)..(8)
<220> FEATURE:
<221> NAME/KEY: BNANC(NMe)
<222> LOCATION: (9)..(9)
<220> FEATURE:
<221> NAME/KEY: 2'-OMe
<222> LOCATION: (10)..(13)
<220> FEATURE:
<221> NAME/KEY: BNANC(NMe)
<222> LOCATION: (14)..(14)
<220> FEATURE:
<221> NAME/KEY: 2'-OMe
<222> LOCATION: (15)..(46)
<220> FEATURE:
<221> NAME/KEY: BNANC(NMe)
<222> LOCATION: (47)..(47)
<220> FEATURE:
<221> NAME/KEY: 2'-OMe
<222> LOCATION: (48)..(51)
<220> FEATURE:
<221> NAME/KEY: BNANC(NMe)
<222> LOCATION: (52)..(52)

<400> SEQUENCE: 5
gacggcgcta ggatcaucaa acaaugugca gacuacugua aaguaucug gt              52

<210> SEQ ID NO 6
<211> LENGTH: 52
<212> TYPE: DNA
<213> ORGANISM: artificial sequence
<220> FEATURE:
<223> OTHER INFORMATION: antisense sequence (2)
<220> FEATURE:
<221> NAME/KEY: 2'-OMe
<222> LOCATION: (1)..(52)

<400> SEQUENCE: 6
```

```
accagaauac aaacaaugug cagacuacug uaaagaugau ccuagcgccg uc          52
```

<210> SEQ ID NO 7
<211> LENGTH: 52
<212> TYPE: DNA
<213> ORGANISM: artificial sequence
<220> FEATURE:
<223> OTHER INFORMATION: sense sequence (3)
<220> FEATURE:
<221> NAME/KEY: 2'-OMe
<222> LOCATION: (1)..(8)
<220> FEATURE:
<221> NAME/KEY: BNANC(NMe)
<222> LOCATION: (9)..(9)
<220> FEATURE:
<221> NAME/KEY: 2'-OMe
<222> LOCATION: (10)..(51)
<220> FEATURE:
<221> NAME/KEY: BNANC(NMe)
<222> LOCATION: (52)..(52)

<400> SEQUENCE: 7

```
gacggcgcta ggaucaucaa acaaugugca gacuacugua aaguauucug gt          52
```

<210> SEQ ID NO 8
<211> LENGTH: 52
<212> TYPE: DNA
<213> ORGANISM: artificial sequence
<220> FEATURE:
<223> OTHER INFORMATION: antisense sequence (3)
<220> FEATURE:
<221> NAME/KEY: 2'-OMe
<222> LOCATION: (1)..(7)
<220> FEATURE:
<221> NAME/KEY: BNANC(NMe)
<222> LOCATION: (8)..(8)
<220> FEATURE:
<221> NAME/KEY: 2'-OMe
<222> LOCATION: (9)..(39)
<220> FEATURE:
<221> NAME/KEY: BNANC(NMe)
<222> LOCATION: (40)..(40)
<220> FEATURE:
<221> NAME/KEY: 2'-OMe
<222> LOCATION: (41)..(52)

<400> SEQUENCE: 8

```
accagaatac aaacaaugug cagacuacug uaaagaugat ccuagcgccg uc          52
```

<210> SEQ ID NO 9
<211> LENGTH: 52
<212> TYPE: DNA
<213> ORGANISM: artificial sequence
<220> FEATURE:
<223> OTHER INFORMATION: sense sequence (4)
<220> FEATURE:
<221> NAME/KEY: 2'-OMe
<222> LOCATION: (1)..(8)
<220> FEATURE:
<221> NAME/KEY: BNANC(NMe)
<222> LOCATION: (9)..(9)
<220> FEATURE:
<221> NAME/KEY: 2'-OMe
<222> LOCATION: (10)..(13)
<220> FEATURE:
<221> NAME/KEY: BNANC(NMe)
<222> LOCATION: (14)..(14)
<220> FEATURE:
<221> NAME/KEY: 2'-OMe
<222> LOCATION: (15)..(46)
<220> FEATURE:
<221> NAME/KEY: BNANC(NMe)
<222> LOCATION: (47)..(47)

```
<220> FEATURE:
<221> NAME/KEY: 2'-OMe
<222> LOCATION: (48)..(51)
<220> FEATURE:
<221> NAME/KEY: BNANC(NMe)
<222> LOCATION: (52)..(52)

<400> SEQUENCE: 9
gacggcgcta ggatcaucaa acaaugugca gacuacugua aaguautcug gt      52

<210> SEQ ID NO 10
<211> LENGTH: 52
<212> TYPE: DNA
<213> ORGANISM: artificial sequence
<220> FEATURE:
<223> OTHER INFORMATION: antisense sequence (4)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(5)
<220> FEATURE:
<221> NAME/KEY: BNANC(NMe)
<222> LOCATION: (6)..(6)
<220> FEATURE:
<221> NAME/KEY: 2'-OMe
<222> LOCATION: (7)..(38)
<220> FEATURE:
<221> NAME/KEY: BNANC(NMe)
<222> LOCATION: (39)..(39)
<220> FEATURE:
<221> NAME/KEY: 2'-OMe
<222> LOCATION: (40)..(43)
<220> FEATURE:
<221> NAME/KEY: BNANC(NMe)
<222> LOCATION: (44)..(44)
<220> FEATURE:
<221> NAME/KEY: 2'-OMe
<222> LOCATION: (45)..(52)

<400> SEQUENCE: 10
accagaauac aaacaaugug cagacuacug uaaagaugau ccuagcgccg uc      52

<210> SEQ ID NO 11
<211> LENGTH: 44
<212> TYPE: DNA
<213> ORGANISM: artificial sequence
<220> FEATURE:
<223> OTHER INFORMATION: sense sequence (5)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(5)
<220> FEATURE:
<221> NAME/KEY: BNANC(NMe)
<222> LOCATION: (6)..(6)
<220> FEATURE:
<221> NAME/KEY: 2'-OMe
<222> LOCATION: (7)..(38)
<220> FEATURE:
<221> NAME/KEY: BNANC(NMe)
<222> LOCATION: (39)..(39)
<220> FEATURE:
<221> NAME/KEY: 2'-OMe
<222> LOCATION: (40)..(43)
<220> FEATURE:
<221> NAME/KEY: BNANC(NMe)
<222> LOCATION: (44)..(44)

<400> SEQUENCE: 11
taggatcauc aaacaaugug cagacuacug uaaaguautc uggt              44
```

```
<210> SEQ ID NO 12
<211> LENGTH: 44
<212> TYPE: DNA
<213> ORGANISM: artificial sequence
<220> FEATURE:
<223> OTHER INFORMATION: antisense sequence (5)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(5)
<220> FEATURE:
<221> NAME/KEY: BNANC(NMe)
<222> LOCATION: (6)..(6)
<220> FEATURE:
<221> NAME/KEY: 2'-OMe
<222> LOCATION: (7)..(38)
<220> FEATURE:
<221> NAME/KEY: BNANC(NMe)
<222> LOCATION: (39)..(39)
<220> FEATURE:
<221> NAME/KEY: 2'-OMe
<222> LOCATION: (40)..(43)
<220> FEATURE:
<221> NAME/KEY: BNANC(NMe)
<222> LOCATION: (44)..(44)

<400> SEQUENCE: 12
accagaauac aaacaaugug cagacuacug uaaagaugau ccua             44

<210> SEQ ID NO 13
<211> LENGTH: 52
<212> TYPE: DNA
<213> ORGANISM: artificial sequence
<220> FEATURE:
<223> OTHER INFORMATION: sense sequence (16)
<220> FEATURE:
<221> NAME/KEY: BNANC(NMe)
<222> LOCATION: (1)..(1)
<220> FEATURE:
<221> NAME/KEY: 2'-OMe
<222> LOCATION: (1)..(1)
<220> FEATURE:
<221> NAME/KEY: 2'-OMe
<222> LOCATION: (2)..(43)
<220> FEATURE:
<221> NAME/KEY: BNANC(NMe)
<222> LOCATION: (44)..(44)
<220> FEATURE:
<221> NAME/KEY: 2'-OMe
<222> LOCATION: (45)..(48)
<220> FEATURE:
<221> NAME/KEY: BNANC(NMe)
<222> LOCATION: (49)..(49)
<220> FEATURE:
<221> NAME/KEY: 2'-OMe
<222> LOCATION: (50)..(52)

<400> SEQUENCE: 13
tacggcgcua ggaucaucaa acaaugugca gacuacugua aagtauucctg ga        52

<210> SEQ ID NO 14
<211> LENGTH: 52
<212> TYPE: DNA
<213> ORGANISM: artificial sequence
<220> FEATURE:
<223> OTHER INFORMATION: antisense sequence (16)
<220> FEATURE:
<221> NAME/KEY: BNANC(NMe)
<222> LOCATION: (1)..(1)
<220> FEATURE:
<221> NAME/KEY: 2'-OMe
```

```
<222> LOCATION: (2)..(36)
<220> FEATURE:
<221> NAME/KEY: BNANC(NMe)
<222> LOCATION: (37)..(37)
<220> FEATURE:
<221> NAME/KEY: 2'-OMe
<222> LOCATION: (38)..(42)
<220> FEATURE:
<221> NAME/KEY: BNANC(NMe)
<222> LOCATION: (43)..(43)
<220> FEATURE:
<221> NAME/KEY: 2'-OMe
<222> LOCATION: (44)..(52)

<400> SEQUENCE: 14
tccagaauac aaacaaugug cagacuacug uaaagatgau cctagcgccg ua        52

<210> SEQ ID NO 15
<211> LENGTH: 52
<212> TYPE: DNA
<213> ORGANISM: artificial sequence
<220> FEATURE:
<223> OTHER INFORMATION: sense sequence (22)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(33)
<220> FEATURE:
<221> NAME/KEY: BNANC(NMe)
<222> LOCATION: (34)..(34)
<220> FEATURE:
<221> NAME/KEY: 2'-OMe
<222> LOCATION: (35)..(36)
<220> FEATURE:
<221> NAME/KEY: BNANC(NMe)
<222> LOCATION: (37)..(37)
<220> FEATURE:
<221> NAME/KEY: 2'-OMe
<222> LOCATION: (38)..(43)
<220> FEATURE:
<221> NAME/KEY: BNANC(NMe)
<222> LOCATION: (44)..(44)
<220> FEATURE:
<221> NAME/KEY: 2'-OMe
<222> LOCATION: (45)..(48)
<220> FEATURE:
<221> NAME/KEY: BNANC(NMe)
<222> LOCATION: (49)..(49)
<220> FEATURE:
<221> NAME/KEY: 2'-OMe
<222> LOCATION: (50)..(52)

<400> SEQUENCE: 15
tacggcgcua ggaucaucaa acaaugugca gactactgua aagtauucug ga        52

<210> SEQ ID NO 16
<211> LENGTH: 52
<212> TYPE: DNA
<213> ORGANISM: artificial sequence
<220> FEATURE:
<223> OTHER INFORMATION: antisense sequence (22)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(25)
<220> FEATURE:
<221> NAME/KEY: BNANC(NMe)
<222> LOCATION: (26)..(26)
<220> FEATURE:
<221> NAME/KEY: 2'-OMe
<222> LOCATION: (27)..(28)
```

-continued

```
<220> FEATURE:
<221> NAME/KEY: BNANC(NMe)
<222> LOCATION: (29)..(29)
<220> FEATURE:
<221> NAME/KEY: 2'-OMe
<222> LOCATION: (30)..(36)
<220> FEATURE:
<221> NAME/KEY: BNANC(NMe)
<222> LOCATION: (37)..(37)
<220> FEATURE:
<221> NAME/KEY: 2'-OMe
<222> LOCATION: (38)..(42)
<220> FEATURE:
<221> NAME/KEY: BNANC(NMe)
<222> LOCATION: (43)..(43)
<220> FEATURE:
<221> NAME/KEY: 2'-OMe
<222> LOCATION: (44)..(52)

<400> SEQUENCE: 16
tccagaauac aaacaaugug cagactactg uaaagatgau cctagcgccg ua            52

<210> SEQ ID NO 17
<211> LENGTH: 52
<212> TYPE: DNA
<213> ORGANISM: artificial sequence
<220> FEATURE:
<223> OTHER INFORMATION: sense sequence (23)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(23)
<220> FEATURE:
<221> NAME/KEY: BNANC(NMe)
<222> LOCATION: (24)..(24)
<220> FEATURE:
<221> NAME/KEY: 2'-OMe
<222> LOCATION: (25)..(26)
<220> FEATURE:
<221> NAME/KEY: BNANC(NMe)
<222> LOCATION: (27)..(27)
<220> FEATURE:
<221> NAME/KEY: 2'-OMe
<222> LOCATION: (28)..(43)
<220> FEATURE:
<221> NAME/KEY: BNANC(NMe)
<222> LOCATION: (44)..(44)
<220> FEATURE:
<221> NAME/KEY: 2'-OMe
<222> LOCATION: (45)..(48)
<220> FEATURE:
<221> NAME/KEY: BNANC(NMe)
<222> LOCATION: (49)..(49)
<220> FEATURE:
<221> NAME/KEY: 2'-OMe
<222> LOCATION: (50)..(52)

<400> SEQUENCE: 17
tacggcgcua ggaucaucaa acaaugtgca gacuacugua aagtauuctg ga            52

<210> SEQ ID NO 18
<211> LENGTH: 52
<212> TYPE: DNA
<213> ORGANISM: artificial sequence
<220> FEATURE:
<223> OTHER INFORMATION: antisense sequence (23)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(15)
<220> FEATURE:
```

```
<221> NAME/KEY: BNANC(NMe)
<222> LOCATION: (16)..(16)
<220> FEATURE:
<221> NAME/KEY: 2'-OMe
<222> LOCATION: (17)..(18)
<220> FEATURE:
<221> NAME/KEY: BNANC(NMe)
<222> LOCATION: (19)..(19)
<220> FEATURE:
<221> NAME/KEY: 2'-OMe
<222> LOCATION: (20)..(36)
<220> FEATURE:
<221> NAME/KEY: BNANC(NMe)
<222> LOCATION: (37)..(37)
<220> FEATURE:
<221> NAME/KEY: 2'-OMe
<222> LOCATION: (38)..(42)
<220> FEATURE:
<221> NAME/KEY: BNANC(NMe)
<222> LOCATION: (43)..(43)
<220> FEATURE:
<221> NAME/KEY: 2'-OMe
<222> LOCATION: (44)..(52)

<400> SEQUENCE: 18
tccagaauac aaacaaugtg cagacuacug uaaagatgau cctagcgccg ua          52

<210> SEQ ID NO 19
<211> LENGTH: 52
<212> TYPE: DNA
<213> ORGANISM: artificial sequence
<220> FEATURE:
<223> OTHER INFORMATION: sense sequence (24)
<220> FEATURE:
<221> NAME/KEY: 2'-OMe
<222> LOCATION: (1)..(1)
<220> FEATURE:
<221> NAME/KEY: BNANC(NMe)
<222> LOCATION: (2)..(2)
<220> FEATURE:
<221> NAME/KEY: 2'-OMe
<222> LOCATION: (3)..(23)
<220> FEATURE:
<221> NAME/KEY: BNANC(NMe)
<222> LOCATION: (24)..(24)
<220> FEATURE:
<221> NAME/KEY: 2'-OMe
<222> LOCATION: (25)..(26)
<220> FEATURE:
<221> NAME/KEY: BNANC(NMe)
<222> LOCATION: (27)..(27)
<220> FEATURE:
<221> NAME/KEY: 2'-OMe
<222> LOCATION: (28)..(43)
<220> FEATURE:
<221> NAME/KEY: BNANC(NMe)
<222> LOCATION: (44)..(44)
<220> FEATURE:
<221> NAME/KEY: 2'-OMe
<222> LOCATION: (45)..(51)
<220> FEATURE:
<221> NAME/KEY: BNANC(NMe)
<222> LOCATION: (52)..(52)

<400> SEQUENCE: 19
atcggcgcua ggaucaucaa acaaugtgca gacuacugua aagtauucug at          52

<210> SEQ ID NO 20
<211> LENGTH: 52
<212> TYPE: DNA
<213> ORGANISM: artificial sequence
<220> FEATURE:
<223> OTHER INFORMATION: antisense sequence (24)
<220> FEATURE:
<221> NAME/KEY: 2'-OMe
```

```
<222> LOCATION: (1)..(1)
<220> FEATURE:
<221> NAME/KEY: BNANC(NMe)
<222> LOCATION: (2)..(2)
<220> FEATURE:
<221> NAME/KEY: 2'-OMe
<222> LOCATION: (3)..(15)
<220> FEATURE:
<221> NAME/KEY: BNANC(NMe)
<222> LOCATION: (16)..(16)
<220> FEATURE:
<221> NAME/KEY: 2'-OMe
<222> LOCATION: (17)..(18)
<220> FEATURE:
<221> NAME/KEY: BNANC(NMe)
<222> LOCATION: (19)..(19)
<220> FEATURE:
<221> NAME/KEY: 2'-OMe
<222> LOCATION: (20)..(42)
<220> FEATURE:
<221> NAME/KEY: BNANC(NMe)
<222> LOCATION: (43)..(43)
<220> FEATURE:
<221> NAME/KEY: 2'-OMe
<222> LOCATION: (44)..(51)
<220> FEATURE:
<221> NAME/KEY: BNANC(NMe)
<222> LOCATION: (52)..(52)

<400> SEQUENCE: 20
atcagaauac aaacaaugtg cagacuacug uaaagaugau cctagcgccg at        52

<210> SEQ ID NO 21
<211> LENGTH: 44
<212> TYPE: DNA
<213> ORGANISM: artificial sequence
<220> FEATURE:
<223> OTHER INFORMATION: sense sequence (17)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(25)
<220> FEATURE:
<221> NAME/KEY: BNANC(NMe)
<222> LOCATION: (26)..(26)
<220> FEATURE:
<221> NAME/KEY: 2'-OMe
<222> LOCATION: (27)..(28)
<220> FEATURE:
<221> NAME/KEY: BNANC(NMe)
<222> LOCATION: (29)..(29)
<220> FEATURE:
<221> NAME/KEY: 2'-OMe
<222> LOCATION: (30)..(38)
<220> FEATURE:
<221> NAME/KEY: BNANC(NMe)
<222> LOCATION: (39)..(39)
<220> FEATURE:
<221> NAME/KEY: 2'-OMe
<222> LOCATION: (40)..(43)
<220> FEATURE:
<221> NAME/KEY: BNANC(NMe)
<222> LOCATION: (44)..(44)

<400> SEQUENCE: 21
taggaucauc aaacaaugug cagactactg uaaaguautc uggt        44

<210> SEQ ID NO 22
<211> LENGTH: 44
<212> TYPE: DNA
<213> ORGANISM: artificial sequence
<220> FEATURE:
<223> OTHER INFORMATION: antisense sequence (17)
```

```
<220> FEATURE:
<221> NAME/KEY: 2'-OMe
<222> LOCATION: (1)..(7)
<220> FEATURE:
<221> NAME/KEY: BNANC(NMe)
<222> LOCATION: (8)..(8)
<220> FEATURE:
<221> NAME/KEY: 2'-OMe
<222> LOCATION: (9)..(25)
<220> FEATURE:
<221> NAME/KEY: BNANC(NMe)
<222> LOCATION: (26)..(26)
<220> FEATURE:
<221> NAME/KEY: 2'-OMe
<222> LOCATION: (27)..(28)
<220> FEATURE:
<221> NAME/KEY: BNANC(NMe)
<222> LOCATION: (29)..(29)
<220> FEATURE:
<221> NAME/KEY: 2'-OMe
<222> LOCATION: (30)..(36)
<220> FEATURE:
<221> NAME/KEY: BNANC(NMe)
<222> LOCATION: (37)..(37)
<220> FEATURE:
<221> NAME/KEY: 2'-OMe
<222> LOCATION: (38)..(39)
<220> FEATURE:
<221> NAME/KEY: BNANC(NMe)
<222> LOCATION: (40)..(40)
<220> FEATURE:
<221> NAME/KEY: 2'-OMe
<222> LOCATION: (41)..(44)

<400> SEQUENCE: 22
accagaatac aaacaaugug cagactactg uaaagatgat ccua          44

<210> SEQ ID NO 23
<211> LENGTH: 44
<212> TYPE: DNA
<213> ORGANISM: artificial sequence
<220> FEATURE:
<223> OTHER INFORMATION: sense sequence (18)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(15)
<220> FEATURE:
<221> NAME/KEY: BNANC(NMe)
<222> LOCATION: (16)..(16)
<220> FEATURE:
<221> NAME/KEY: 2'-OMe
<222> LOCATION: (17)..(18)
<220> FEATURE:
<221> NAME/KEY: BNANC(NMe)
<222> LOCATION: (19)..(19)
<220> FEATURE:
<221> NAME/KEY: 2'-OMe
<222> LOCATION: (20)..(38)
<220> FEATURE:
<221> NAME/KEY: BNANC(NMe)
<222> LOCATION: (39)..(39)
<220> FEATURE:
<221> NAME/KEY: 2'-OMe
<222> LOCATION: (40)..(43)
<220> FEATURE:
<221> NAME/KEY: BNANC(NMe)
<222> LOCATION: (44)..(44)

<400> SEQUENCE: 23
taggaucauc aaacaaugtg cagacuacug uaaaguautc uggt          44

<210> SEQ ID NO 24
```

```
<211> LENGTH: 44
<212> TYPE: DNA
<213> ORGANISM: artificial sequence
<220> FEATURE:
<223> OTHER INFORMATION: antisense sequence (18)
<220> FEATURE:
<221> NAME/KEY: 2'-OMe
<222> LOCATION: (1)..(7)
<220> FEATURE:
<221> NAME/KEY: BNANC(NMe)
<222> LOCATION: (8)..(8)
<220> FEATURE:
<221> NAME/KEY: 2'-OMe
<222> LOCATION: (9)..(15)
<220> FEATURE:
<221> NAME/KEY: BNANC(NMe)
<222> LOCATION: (16)..(16)
<220> FEATURE:
<221> NAME/KEY: 2'-OMe
<222> LOCATION: (17)..(18)
<220> FEATURE:
<221> NAME/KEY: BNANC(NMe)
<222> LOCATION: (19)..(19)
<220> FEATURE:
<221> NAME/KEY: 2'-OMe
<222> LOCATION: (20)..(36)
<220> FEATURE:
<221> NAME/KEY: BNANC(NMe)
<222> LOCATION: (37)..(37)
<220> FEATURE:
<221> NAME/KEY: 2'-OMe
<222> LOCATION: (38)..(39)
<220> FEATURE:
<221> NAME/KEY: BNANC(NMe)
<222> LOCATION: (40)..(40)
<220> FEATURE:
<221> NAME/KEY: 2'-OMe
<222> LOCATION: (41)..(44)

<400> SEQUENCE: 24
accagaatac aaacaaugtg cagacuacug uaaagatgat ccua                44

<210> SEQ ID NO 25
<211> LENGTH: 52
<212> TYPE: DNA
<213> ORGANISM: artificial sequence
<220> FEATURE:
<223> OTHER INFORMATION: sense sequence (23)-(1)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(23)
<220> FEATURE:
<221> NAME/KEY: phosphorothioate linkage
<222> LOCATION: (19)..(41)
<220> FEATURE:
<221> NAME/KEY: BNANC(NMe)
<222> LOCATION: (24)..(24)
<220> FEATURE:
<221> NAME/KEY: 2'-OMe
<222> LOCATION: (25)..(26)
<220> FEATURE:
<221> NAME/KEY: BNANC(NMe)
<222> LOCATION: (27)..(27)
<220> FEATURE:
<221> NAME/KEY: 2'-OMe
<222> LOCATION: (28)..(43)
<220> FEATURE:
<221> NAME/KEY: BNANC(NMe)
<222> LOCATION: (44)..(44)
<220> FEATURE:
<221> NAME/KEY: 2'-OMe
<222> LOCATION: (45)..(48)
<220> FEATURE:
<221> NAME/KEY: BNANC(NMe)
```

```
<222> LOCATION: (49)..(49)
<220> FEATURE:
<221> NAME/KEY: 2'-OMe
<222> LOCATION: (50)..(52)

<400> SEQUENCE: 25
tacggcgcua ggaucaucaa acaaugtgca gacuacugua aagtauuctg ga          52

<210> SEQ ID NO 26
<211> LENGTH: 52
<212> TYPE: DNA
<213> ORGANISM: artificial sequence
<220> FEATURE:
<223> OTHER INFORMATION: antisense sequence (23)-(1)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(15)
<220> FEATURE:
<221> NAME/KEY: phosphorothioate linkage
<222> LOCATION: (12)..(34)
<220> FEATURE:
<221> NAME/KEY: BNANC(NMe)
<222> LOCATION: (16)..(16)
<220> FEATURE:
<221> NAME/KEY: 2'-OMe
<222> LOCATION: (17)..(18)
<220> FEATURE:
<221> NAME/KEY: BNANC(NMe)
<222> LOCATION: (19)..(19)
<220> FEATURE:
<221> NAME/KEY: 2'-OMe
<222> LOCATION: (20)..(36)
<220> FEATURE:
<221> NAME/KEY: BNANC(NMe)
<222> LOCATION: (37)..(37)
<220> FEATURE:
<221> NAME/KEY: 2'-OMe
<222> LOCATION: (38)..(42)
<220> FEATURE:
<221> NAME/KEY: BNANC(NMe)
<222> LOCATION: (43)..(43)
<220> FEATURE:
<221> NAME/KEY: 2'-OMe
<222> LOCATION: (44)..(52)

<400> SEQUENCE: 26
tccagaauac aaacaaugtg cagacuacug uaaagatgau cctagcgccg ua          52

<210> SEQ ID NO 27
<211> LENGTH: 52
<212> TYPE: DNA
<213> ORGANISM: artificial sequence
<220> FEATURE:
<223> OTHER INFORMATION: sense sequence (23)-(2)
<220> FEATURE:
<221> NAME/KEY: phosphorothioate linkage
<222> LOCATION: (1)..(17)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(23)
<220> FEATURE:
<221> NAME/KEY: BNANC(NMe)
<222> LOCATION: (24)..(24)
<220> FEATURE:
<221> NAME/KEY: 2'-OMe
<222> LOCATION: (25)..(26)
<220> FEATURE:
<221> NAME/KEY: BNANC(NMe)
<222> LOCATION: (27)..(27)
```

<220> FEATURE:
<221> NAME/KEY: 2'-OMe
<222> LOCATION: (28)..(43)
<220> FEATURE:
<221> NAME/KEY: phosphorothioate linkage
<222> LOCATION: (43)..(51)
<220> FEATURE:
<221> NAME/KEY: BNANC(NMe)
<222> LOCATION: (44)..(44)
<220> FEATURE:
<221> NAME/KEY: 2'-OMe
<222> LOCATION: (45)..(48)
<220> FEATURE:
<221> NAME/KEY: BNANC(NMe)
<222> LOCATION: (49)..(49)
<220> FEATURE:
<221> NAME/KEY: 2'-OMe
<222> LOCATION: (50)..(52)

<400> SEQUENCE: 27
tacggcgcua ggaucaucaa acaaugtgca gacuacugua aagtauuctg ga          52

<210> SEQ ID NO 28
<211> LENGTH: 52
<212> TYPE: DNA
<213> ORGANISM: artificial sequence
<220> FEATURE:
<223> OTHER INFORMATION: antisense sequence (23)-(2)
<220> FEATURE:
<221> NAME/KEY: BNANC(NMe)
<222> LOCATION: (1)..(1)
<220> FEATURE:
<221> NAME/KEY: phosphorothioate linkage
<222> LOCATION: (2)..(10)
<220> FEATURE:
<221> NAME/KEY: 2'-OMe
<222> LOCATION: (2)..(15)
<220> FEATURE:
<221> NAME/KEY: BNANC(NMe)
<222> LOCATION: (16)..(16)
<220> FEATURE:
<221> NAME/KEY: 2'-OMe
<222> LOCATION: (17)..(18)
<220> FEATURE:
<221> NAME/KEY: BNANC(NMe)
<222> LOCATION: (19)..(19)
<220> FEATURE:
<221> NAME/KEY: 2'-OMe
<222> LOCATION: (20)..(36)
<220> FEATURE:
<221> NAME/KEY: phosphorothioate linkage
<222> LOCATION: (36)..(52)
<220> FEATURE:
<221> NAME/KEY: BNANC(NMe)
<222> LOCATION: (37)..(37)
<220> FEATURE:
<221> NAME/KEY: 2'-OMe
<222> LOCATION: (38)..(42)
<220> FEATURE:
<221> NAME/KEY: BNANC(NMe)
<222> LOCATION: (43)..(43)
<220> FEATURE:
<221> NAME/KEY: 2'-OMe
<222> LOCATION: (44)..(52)

<400> SEQUENCE: 28
tccagaauac aaacaaugtg cagacuacug uaaagatgau cctagcgccg ua          52

<210> SEQ ID NO 29
<211> LENGTH: 52
<212> TYPE: DNA
<213> ORGANISM: artificial sequence
<220> FEATURE:
<223> OTHER INFORMATION: sense sequence (23)-(3)
<220> FEATURE:

```
<221> NAME/KEY: BNANC(NMe)
<222> LOCATION: (1)..(1)
<220> FEATURE:
<221> NAME/KEY: phosphorothioate linkage
<222> LOCATION: (1)..(51)
<220> FEATURE:
<221> NAME/KEY: 2'-OMe
<222> LOCATION: (2)..(23)
<220> FEATURE:
<221> NAME/KEY: BNANC(NMe)
<222> LOCATION: (24)..(24)
<220> FEATURE:
<221> NAME/KEY: 2'-OMe
<222> LOCATION: (25)..(26)
<220> FEATURE:
<221> NAME/KEY: BNANC(NMe)
<222> LOCATION: (27)..(27)
<220> FEATURE:
<221> NAME/KEY: 2'-OMe
<222> LOCATION: (28)..(43)
<220> FEATURE:
<221> NAME/KEY: BNANC(NMe)
<222> LOCATION: (44)..(44)
<220> FEATURE:
<221> NAME/KEY: 2'-OMe
<222> LOCATION: (45)..(48)
<220> FEATURE:
<221> NAME/KEY: BNANC(NMe)
<222> LOCATION: (49)..(49)
<220> FEATURE:
<221> NAME/KEY: 2'-OMe
<222> LOCATION: (50)..(52)

<400> SEQUENCE: 29
tacggcgcua ggaucaucaa acaaugtgca gacuacugua aagtauucctg ga          52

<210> SEQ ID NO 30
<211> LENGTH: 52
<212> TYPE: DNA
<213> ORGANISM: artificial sequence
<220> FEATURE:
<223> OTHER INFORMATION: antisense sequence (23)-(3)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(15)
<220> FEATURE:
<221> NAME/KEY: phosphorothioate linkage
<222> LOCATION: (2)..(52)
<220> FEATURE:
<221> NAME/KEY: BNANC(NMe)
<222> LOCATION: (16)..(16)
<220> FEATURE:
<221> NAME/KEY: 2'-OMe
<222> LOCATION: (17)..(18)
<220> FEATURE:
<221> NAME/KEY: BNANC(NMe)
<222> LOCATION: (19)..(19)
<220> FEATURE:
<221> NAME/KEY: 2'-OMe
<222> LOCATION: (20)..(36)
<220> FEATURE:
<221> NAME/KEY: BNANC(NMe)
<222> LOCATION: (37)..(37)
<220> FEATURE:
<221> NAME/KEY: 2'-OMe
<222> LOCATION: (38)..(42)
<220> FEATURE:
<221> NAME/KEY: BNANC(NMe)
<222> LOCATION: (43)..(43)
<220> FEATURE:
<221> NAME/KEY: 2'-OMe
<222> LOCATION: (44)..(52)

<400> SEQUENCE: 30
```
tccagaauac aaacaaugtg cagacuacug uaaagatgau cctagcgccg ua        52

<210> SEQ ID NO 31
<211> LENGTH: 44
<212> TYPE: DNA
<213> ORGANISM: artificial sequence
<220> FEATURE:
<223> OTHER INFORMATION: sense sequence (1)'
<220> FEATURE:
<221> NAME/KEY: 2'-OMe
<222> LOCATION: (1)..(44)

<400> SEQUENCE: 31
uaggaucauc aaacaaugug cagacuacug uaaaguauuc uggu        44

<210> SEQ ID NO 32
<211> LENGTH: 44
<212> TYPE: DNA
<213> ORGANISM: artificial sequence
<220> FEATURE:
<223> OTHER INFORMATION: antisense sequence (1)'
<220> FEATURE:
<221> NAME/KEY: 2'-OMe
<222> LOCATION: (1)..(44)

<400> SEQUENCE: 32
accagaauac aaacaaugug cagacuacug uaaagaugau ccua        44

<210> SEQ ID NO 33
<211> LENGTH: 44
<212> TYPE: DNA
<213> ORGANISM: artificial sequence
<220> FEATURE:
<223> OTHER INFORMATION: sense sequence (6)'
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(38)
<220> FEATURE:
<221> NAME/KEY: BNANC(NMe)
<222> LOCATION: (39)..(39)
<220> FEATURE:
<221> NAME/KEY: 2'-OMe
<222> LOCATION: (40)..(43)
<220> FEATURE:
<221> NAME/KEY: BNANC(NMe)
<222> LOCATION: (44)..(44)

<400> SEQUENCE: 33
taggaucauc aaacaaugug cagacuacug uaaaguautc uggt        44

<210> SEQ ID NO 34
<211> LENGTH: 44
<212> TYPE: DNA
<213> ORGANISM: artificial sequence
<220> FEATURE:
<223> OTHER INFORMATION: antisense sequence (6)'
<220> FEATURE:
<221> NAME/KEY: 2'-OMe
<222> LOCATION: (1)..(7)
<220> FEATURE:
<221> NAME/KEY: BNANC(NMe)
<222> LOCATION: (8)..(8)
<220> FEATURE:
<221> NAME/KEY: 2'-OMe
<222> LOCATION: (9)..(36)
<220> FEATURE:
<221> NAME/KEY: BNANC(NMe)
<222> LOCATION: (37)..(37)

```
<220> FEATURE:
<221> NAME/KEY: 2'-OMe
<222> LOCATION: (38)..(39)
<220> FEATURE:
<221> NAME/KEY: BNANC(NMe)
<222> LOCATION: (40)..(40)
<220> FEATURE:
<221> NAME/KEY: 2'-OMe
<222> LOCATION: (41)..(44)

<400> SEQUENCE: 34
accagaatac aaacaaugug cagacuacug uaaagatgat ccua              44

<210> SEQ ID NO 35
<211> LENGTH: 52
<212> TYPE: DNA
<213> ORGANISM: artificial sequence
<220> FEATURE:
<223> OTHER INFORMATION: sense sequence (23)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(23)
<220> FEATURE:
<221> NAME/KEY: BNANC(NMe)
<222> LOCATION: (24)..(24)
<220> FEATURE:
<221> NAME/KEY: 2'-OMe
<222> LOCATION: (25)..(26)
<220> FEATURE:
<221> NAME/KEY: BNANC(NMe)
<222> LOCATION: (27)..(27)
<220> FEATURE:
<221> NAME/KEY: 2'-OMe
<222> LOCATION: (28)..(43)
<220> FEATURE:
<221> NAME/KEY: BNANC(NMe)
<222> LOCATION: (44)..(44)
<220> FEATURE:
<221> NAME/KEY: 2'-OMe
<222> LOCATION: (45)..(48)
<220> FEATURE:
<221> NAME/KEY: BNANC(NMe)
<222> LOCATION: (49)..(49)
<220> FEATURE:
<221> NAME/KEY: 2'-OMe
<222> LOCATION: (50)..(52)

<400> SEQUENCE: 35
tacggcgcua ggaucaucaa acaaugtgca gacuacugua aagtauuctg ga          52

<210> SEQ ID NO 36
<211> LENGTH: 52
<212> TYPE: DNA
<213> ORGANISM: artificial sequence
<220> FEATURE:
<223> OTHER INFORMATION: antisense sequence (23)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(15)
<220> FEATURE:
<221> NAME/KEY: BNANC(NMe)
<222> LOCATION: (16)..(16)
<220> FEATURE:
<221> NAME/KEY: 2'-OMe
<222> LOCATION: (17)..(18)
<220> FEATURE:
<221> NAME/KEY: BNANC(NMe)
<222> LOCATION: (19)..(19)
<220> FEATURE:
```

```
<221> NAME/KEY: 2'-OMe
<222> LOCATION: (20)..(36)
<220> FEATURE:
<221> NAME/KEY: BNANC(NMe)
<222> LOCATION: (37)..(37)
<220> FEATURE:
<221> NAME/KEY: 2'-OMe
<222> LOCATION: (38)..(42)
<220> FEATURE:
<221> NAME/KEY: BNANC(NMe)
<222> LOCATION: (43)..(43)
<220> FEATURE:
<221> NAME/KEY: 2'-OMe
<222> LOCATION: (44)..(52)

<400> SEQUENCE: 36
tccagaauac aaacaaugtg cagacuacug uaaagatgau cctagcgccg ua           52

<210> SEQ ID NO 37
<211> LENGTH: 56
<212> TYPE: DNA
<213> ORGANISM: artificial sequence
<220> FEATURE:
<223> OTHER INFORMATION: sense sequence (41)
<220> FEATURE:
<221> NAME/KEY: 2'-OMe
<222> LOCATION: (1)..(56)

<400> SEQUENCE: 37
uacggcgcua ggaucaucaa cccaucauua cccggcagua uuacaaguau ucugga       56

<210> SEQ ID NO 38
<211> LENGTH: 56
<212> TYPE: DNA
<213> ORGANISM: artificial sequence
<220> FEATURE:
<223> OTHER INFORMATION: antisense sequence (41)
<220> FEATURE:
<221> NAME/KEY: 2'-OMe
<222> LOCATION: (1)..(56)

<400> SEQUENCE: 38
uccagaauac aacccaucau uacccggcag uauuacaaga ugauccuagc gccgua       56

<210> SEQ ID NO 39
<211> LENGTH: 56
<212> TYPE: DNA
<213> ORGANISM: artificial sequence
<220> FEATURE:
<223> OTHER INFORMATION: sense sequence (42)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(47)
<220> FEATURE:
<221> NAME/KEY: BNANC(NMe)
<222> LOCATION: (48)..(48)
<220> FEATURE:
<221> NAME/KEY: 2'-OMe
<222> LOCATION: (49)..(52)
<220> FEATURE:
<221> NAME/KEY: BNANC(NMe)
<222> LOCATION: (53)..(53)
<220> FEATURE:
<221> NAME/KEY: 2'-OMe
<222> LOCATION: (54)..(56)

<400> SEQUENCE: 39
tacggcgcua ggaucaucaa cccaucauua cccggcagua uuacaagtau uctgga       56
```

```
<210> SEQ ID NO 40
<211> LENGTH: 56
<212> TYPE: DNA
<213> ORGANISM: artificial sequence
<220> FEATURE:
<223> OTHER INFORMATION: antisense sequence (42)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(40)
<220> FEATURE:
<221> NAME/KEY: BNANC(NMe)
<222> LOCATION: (41)..(41)
<220> FEATURE:
<221> NAME/KEY: 2'-OMe
<222> LOCATION: (42)..(46)
<220> FEATURE:
<221> NAME/KEY: BNANC(NMe)
<222> LOCATION: (47)..(47)
<220> FEATURE:
<221> NAME/KEY: 2'-OMe
<222> LOCATION: (48)..(56)

<400> SEQUENCE: 40
tccagaauac aacccaucau uacccggcag uauuacaaga tgaucctagc gccgua      56

<210> SEQ ID NO 41
<211> LENGTH: 56
<212> TYPE: DNA
<213> ORGANISM: artificial sequence
<220> FEATURE:
<223> OTHER INFORMATION: sense sequence (43)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(38)
<220> FEATURE:
<221> NAME/KEY: BNANC(NMe)
<222> LOCATION: (39)..(39)
<220> FEATURE:
<221> NAME/KEY: 2'-OMe
<222> LOCATION: (40)..(41)
<220> FEATURE:
<221> NAME/KEY: BNANC(NMe)
<222> LOCATION: (42)..(42)
<220> FEATURE:
<221> NAME/KEY: 2'-OMe
<222> LOCATION: (43)..(47)
<220> FEATURE:
<221> NAME/KEY: BNANC(NMe)
<222> LOCATION: (48)..(48)
<220> FEATURE:
<221> NAME/KEY: 2'-OMe
<222> LOCATION: (49)..(52)
<220> FEATURE:
<221> NAME/KEY: BNANC(NMe)
<222> LOCATION: (53)..(53)
<220> FEATURE:
<221> NAME/KEY: 2'-OMe
<222> LOCATION: (54)..(56)

<400> SEQUENCE: 41
tacggcgcua ggaucaucaa cccaucauua cccggcagta utacaagtau uctgga      56

<210> SEQ ID NO 42
<211> LENGTH: 56
<212> TYPE: DNA
<213> ORGANISM: artificial sequence
<220> FEATURE:
<223> OTHER INFORMATION: antisense sequence (43)
```

```
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(30)
<220> FEATURE:
<221> NAME/KEY: BNANC(NMe)
<222> LOCATION: (31)..(31)
<220> FEATURE:
<221> NAME/KEY: 2'-OMe
<222> LOCATION: (32)..(33)
<220> FEATURE:
<221> NAME/KEY: BNANC(NMe)
<222> LOCATION: (34)..(34)
<220> FEATURE:
<221> NAME/KEY: 2'-OMe
<222> LOCATION: (35)..(40)
<220> FEATURE:
<221> NAME/KEY: BNANC(NMe)
<222> LOCATION: (41)..(41)
<220> FEATURE:
<221> NAME/KEY: 2'-OMe
<222> LOCATION: (42)..(46)
<220> FEATURE:
<221> NAME/KEY: BNANC(NMe)
<222> LOCATION: (47)..(47)
<220> FEATURE:
<221> NAME/KEY: 2'-OMe
<222> LOCATION: (48)..(56)

<400> SEQUENCE: 42
tccagaauac aacccaucau uacccggcag tautacaaga tgaucctagc gccgua         56

<210> SEQ ID NO 43
<211> LENGTH: 56
<212> TYPE: DNA
<213> ORGANISM: artificial sequence
<220> FEATURE:
<223> OTHER INFORMATION: sense sequence (44)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(27)
<220> FEATURE:
<221> NAME/KEY: BNANC(NMe)
<222> LOCATION: (28)..(28)
<220> FEATURE:
<221> NAME/KEY: 2'-OMe
<222> LOCATION: (29)..(30)
<220> FEATURE:
<221> NAME/KEY: BNANC(NMe)
<222> LOCATION: (31)..(31)
<220> FEATURE:
<221> NAME/KEY: 2'-OMe
<222> LOCATION: (32)..(47)
<220> FEATURE:
<221> NAME/KEY: BNANC(NMe)
<222> LOCATION: (48)..(48)
<220> FEATURE:
<221> NAME/KEY: 2'-OMe
<222> LOCATION: (49)..(52)
<220> FEATURE:
<221> NAME/KEY: BNANC(NMe)
<222> LOCATION: (53)..(53)
<220> FEATURE:
<221> NAME/KEY: 2'-OMe
<222> LOCATION: (54)..(56)

<400> SEQUENCE: 43
tacggcgcua ggaucaucaa cccaucatua cccggcagua uuacaagtau uctgga         56

<210> SEQ ID NO 44
```

```
<211> LENGTH: 56
<212> TYPE: DNA
<213> ORGANISM: artificial sequence
<220> FEATURE:
<223> OTHER INFORMATION: antisense sequence (44)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(19)
<220> FEATURE:
<221> NAME/KEY: BNANC(NMe)
<222> LOCATION: (20)..(20)
<220> FEATURE:
<221> NAME/KEY: 2'-OMe
<222> LOCATION: (21)..(22)
<220> FEATURE:
<221> NAME/KEY: BNANC(NMe)
<222> LOCATION: (23)..(23)
<220> FEATURE:
<221> NAME/KEY: 2'-OMe
<222> LOCATION: (24)..(40)
<220> FEATURE:
<221> NAME/KEY: BNANC(NMe)
<222> LOCATION: (41)..(41)
<220> FEATURE:
<221> NAME/KEY: 2'-OMe
<222> LOCATION: (42)..(46)
<220> FEATURE:
<221> NAME/KEY: BNANC(NMe)
<222> LOCATION: (47)..(47)
<220> FEATURE:
<221> NAME/KEY: 2'-OMe
<222> LOCATION: (48)..(56)

<400> SEQUENCE: 44
tccagaauac aacccaucat uacccggcag uauuacaaga tgaucctagc gccgua      56

<210> SEQ ID NO 45
<211> LENGTH: 48
<212> TYPE: DNA
<213> ORGANISM: artificial sequence
<220> FEATURE:
<223> OTHER INFORMATION: sense sequence (45)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(19)
<220> FEATURE:
<221> NAME/KEY: BNANC(NMe)
<222> LOCATION: (20)..(20)
<220> FEATURE:
<221> NAME/KEY: 2'-OMe
<222> LOCATION: (21)..(22)
<220> FEATURE:
<221> NAME/KEY: BNANC(NMe)
<222> LOCATION: (23)..(23)
<220> FEATURE:
<221> NAME/KEY: 2'-OMe
<222> LOCATION: (24)..(42)
<220> FEATURE:
<221> NAME/KEY: BNANC(NMe)
<222> LOCATION: (43)..(43)
<220> FEATURE:
<221> NAME/KEY: 2'-OMe
<222> LOCATION: (44)..(47)
<220> FEATURE:
<221> NAME/KEY: BNANC(NMe)
<222> LOCATION: (48)..(48)

<400> SEQUENCE: 45
taggaucauc aacccaucat uacccggcag uauuacaagu autcuggt      48
```

```
<210> SEQ ID NO 46
<211> LENGTH: 48
<212> TYPE: DNA
<213> ORGANISM: artificial sequence
<220> FEATURE:
<223> OTHER INFORMATION: antisense sequence (45)
<220> FEATURE:
<221> NAME/KEY: 2'-OMe
<222> LOCATION: (1)..(7)
<220> FEATURE:
<221> NAME/KEY: BNANC(NMe)
<222> LOCATION: (8)..(8)
<220> FEATURE:
<221> NAME/KEY: 2'-OMe
<222> LOCATION: (9)..(19)
<220> FEATURE:
<221> NAME/KEY: BNANC(NMe)
<222> LOCATION: (20)..(20)
<220> FEATURE:
<221> NAME/KEY: 2'-OMe
<222> LOCATION: (21)..(22)
<220> FEATURE:
<221> NAME/KEY: BNANC(NMe)
<222> LOCATION: (23)..(23)
<220> FEATURE:
<221> NAME/KEY: 2'-OMe
<222> LOCATION: (24)..(40)
<220> FEATURE:
<221> NAME/KEY: BNANC(NMe)
<222> LOCATION: (41)..(41)
<220> FEATURE:
<221> NAME/KEY: 2'-OMe
<222> LOCATION: (42)..(43)
<220> FEATURE:
<221> NAME/KEY: BNANC(NMe)
<222> LOCATION: (44)..(44)
<220> FEATURE:
<221> NAME/KEY: 2'-OMe
<222> LOCATION: (45)..(48)

<400> SEQUENCE: 46
accagaatac aacccaucat uacccggcag uauuacaaga tgatccua           48

<210> SEQ ID NO 47
<211> LENGTH: 51
<212> TYPE: DNA
<213> ORGANISM: artificial sequence
<220> FEATURE:
<223> OTHER INFORMATION: sense sequence (51)
<220> FEATURE:
<221> NAME/KEY: 2'-OMe
<222> LOCATION: (1)..(51)

<400> SEQUENCE: 47
uacggcgcua ggaucaucaa caucagucgg auaagcuaca aguauucugg a         51

<210> SEQ ID NO 48
<211> LENGTH: 51
<212> TYPE: DNA
<213> ORGANISM: artificial sequence
<220> FEATURE:
<223> OTHER INFORMATION: antisense sequence (51)
<220> FEATURE:
<221> NAME/KEY: 2'-OMe
<222> LOCATION: (1)..(51)

<400> SEQUENCE: 48
uccagaauac aacaucaguc ggauaagcua caagaugauc cuagcgccgu a         51

<210> SEQ ID NO 49
<211> LENGTH: 51
<212> TYPE: DNA
```

```
<213> ORGANISM: artificial sequence
<220> FEATURE:
<223> OTHER INFORMATION: sense sequence (52)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(42)
<220> FEATURE:
<221> NAME/KEY: BNANC(NMe)
<222> LOCATION: (43)..(43)
<220> FEATURE:
<221> NAME/KEY: 2'-OMe
<222> LOCATION: (44)..(47)
<220> FEATURE:
<221> NAME/KEY: BNANC(NMe)
<222> LOCATION: (48)..(48)
<220> FEATURE:
<221> NAME/KEY: 2'-OMe
<222> LOCATION: (49)..(51)

<400> SEQUENCE: 49
tacggcgcua ggaucaucaa caucagucgg auaagcuaca agtauuctgg a          51

<210> SEQ ID NO 50
<211> LENGTH: 51
<212> TYPE: DNA
<213> ORGANISM: artificial sequence
<220> FEATURE:
<223> OTHER INFORMATION: antisense sequence (52)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(35)
<220> FEATURE:
<221> NAME/KEY: BNANC(NMe)
<222> LOCATION: (36)..(36)
<220> FEATURE:
<221> NAME/KEY: 2'-OMe
<222> LOCATION: (37)..(41)
<220> FEATURE:
<221> NAME/KEY: BNANC(NMe)
<222> LOCATION: (42)..(42)
<220> FEATURE:
<221> NAME/KEY: 2'-OMe
<222> LOCATION: (43)..(51)

<400> SEQUENCE: 50
tccagaauac aacaucaguc ggauaagcua caagatgauc ctagcgccgu a          51

<210> SEQ ID NO 51
<211> LENGTH: 51
<212> TYPE: DNA
<213> ORGANISM: artificial sequence
<220> FEATURE:
<223> OTHER INFORMATION: sense sequence (53)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(22)
<220> FEATURE:
<221> NAME/KEY: BNANC(NMe)
<222> LOCATION: (23)..(23)
<220> FEATURE:
<221> NAME/KEY: 2'-OMe
<222> LOCATION: (24)..(25)
<220> FEATURE:
<221> NAME/KEY: BNANC(NMe)
<222> LOCATION: (26)..(26)
<220> FEATURE:
```

```
<221> NAME/KEY: 2'-OMe
<222> LOCATION: (27)..(42)
<220> FEATURE:
<221> NAME/KEY: BNANC(NMe)
<222> LOCATION: (43)..(43)
<220> FEATURE:
<221> NAME/KEY: 2'-OMe
<222> LOCATION: (44)..(47)
<220> FEATURE:
<221> NAME/KEY: BNANC(NMe)
<222> LOCATION: (48)..(48)
<220> FEATURE:
<221> NAME/KEY: 2'-OMe
<222> LOCATION: (49)..(51)

<400> SEQUENCE: 51
tacggcgcua ggaucaucaa caucagucgg auaagcuaca agtauuctgg a       51

<210> SEQ ID NO 52
<211> LENGTH: 51
<212> TYPE: DNA
<213> ORGANISM: artificial sequence
<220> FEATURE:
<223> OTHER INFORMATION: antisense sequence (53)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(14)
<220> FEATURE:
<221> NAME/KEY: BNANC(NMe)
<222> LOCATION: (15)..(15)
<220> FEATURE:
<221> NAME/KEY: 2'-OMe
<222> LOCATION: (16)..(17)
<220> FEATURE:
<221> NAME/KEY: BNANC(NMe)
<222> LOCATION: (18)..(18)
<220> FEATURE:
<221> NAME/KEY: 2'-OMe
<222> LOCATION: (19)..(35)
<220> FEATURE:
<221> NAME/KEY: BNANC(NMe)
<222> LOCATION: (36)..(36)
<220> FEATURE:
<221> NAME/KEY: 2'-OMe
<222> LOCATION: (37)..(41)
<220> FEATURE:
<221> NAME/KEY: BNANC(NMe)
<222> LOCATION: (42)..(42)
<220> FEATURE:
<221> NAME/KEY: 2'-OMe
<222> LOCATION: (43)..(51)

<400> SEQUENCE: 52
tccagaauac aacaucaguc ggauaagcua caagatgauc ctagcgccgu a       51

<210> SEQ ID NO 53
<211> LENGTH: 43
<212> TYPE: DNA
<213> ORGANISM: artificial sequence
<220> FEATURE:
<223> OTHER INFORMATION: sense sequence (54)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(37)
<220> FEATURE:
<221> NAME/KEY: BNANC(NMe)
<222> LOCATION: (38)..(38)
<220> FEATURE:
<221> NAME/KEY: 2'-OMe
```

<222> LOCATION: (39)..(42)
<220> FEATURE:
<221> NAME/KEY: BNANC(NMe)
<222> LOCATION: (43)..(43)

<400> SEQUENCE: 53
taggaucauc aacaucaguc ggauaagcua caaguautcu ggt					43

<210> SEQ ID NO 54
<211> LENGTH: 43
<212> TYPE: DNA
<213> ORGANISM: artificial sequence
<220> FEATURE:
<223> OTHER INFORMATION: antisense sequence (54)
<220> FEATURE:
<221> NAME/KEY: 2'-OMe
<222> LOCATION: (1)..(7)
<220> FEATURE:
<221> NAME/KEY: BNANC(NMe)
<222> LOCATION: (8)..(8)
<220> FEATURE:
<221> NAME/KEY: 2'-OMe
<222> LOCATION: (9)..(35)
<220> FEATURE:
<221> NAME/KEY: BNANC(NMe)
<222> LOCATION: (36)..(36)
<220> FEATURE:
<221> NAME/KEY: 2'-OMe
<222> LOCATION: (37)..(38)
<220> FEATURE:
<221> NAME/KEY: BNANC(NMe)
<222> LOCATION: (39)..(39)
<220> FEATURE:
<221> NAME/KEY: 2'-OMe
<222> LOCATION: (40)..(43)

<400> SEQUENCE: 54
accagaatac aacaucaguc ggauaagcua caagatgatc cua					43

<210> SEQ ID NO 55
<211> LENGTH: 43
<212> TYPE: DNA
<213> ORGANISM: artificial sequence
<220> FEATURE:
<223> OTHER INFORMATION: sense sequence (55)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(14)
<220> FEATURE:
<221> NAME/KEY: BNANC(NMe)
<222> LOCATION: (15)..(15)
<220> FEATURE:
<221> NAME/KEY: 2'-OMe
<222> LOCATION: (16)..(17)
<220> FEATURE:
<221> NAME/KEY: BNANC(NMe)
<222> LOCATION: (18)..(18)
<220> FEATURE:
<221> NAME/KEY: 2'-OMe
<222> LOCATION: (19)..(37)
<220> FEATURE:
<221> NAME/KEY: BNANC(NMe)
<222> LOCATION: (38)..(38)
<220> FEATURE:
<221> NAME/KEY: 2'-OMe
<222> LOCATION: (39)..(42)
<220> FEATURE:
<221> NAME/KEY: BNANC(NMe)
<222> LOCATION: (43)..(43)

<400> SEQUENCE: 55
taggaucauc aacaucaguc ggauaagcua caaguaucu ggt        43

<210> SEQ ID NO 56
<211> LENGTH: 43
<212> TYPE: DNA
<213> ORGANISM: artificial sequence
<220> FEATURE:
<223> OTHER INFORMATION: antisense sequence (55)
<220> FEATURE:
<221> NAME/KEY: 2'-OMe
<222> LOCATION: (1)..(7)
<220> FEATURE:
<221> NAME/KEY: BNANC(NMe)
<222> LOCATION: (8)..(8)
<220> FEATURE:
<221> NAME/KEY: 2'-OMe
<222> LOCATION: (9)..(14)
<220> FEATURE:
<221> NAME/KEY: BNANC(NMe)
<222> LOCATION: (15)..(15)
<220> FEATURE:
<221> NAME/KEY: 2'-OMe
<222> LOCATION: (16)..(17)
<220> FEATURE:
<221> NAME/KEY: BNANC(NMe)
<222> LOCATION: (18)..(18)
<220> FEATURE:
<221> NAME/KEY: 2'-OMe
<222> LOCATION: (19)..(35)
<220> FEATURE:
<221> NAME/KEY: BNANC(NMe)
<222> LOCATION: (36)..(36)
<220> FEATURE:
<221> NAME/KEY: 2'-OMe
<222> LOCATION: (37)..(38)
<220> FEATURE:
<221> NAME/KEY: BNANC(NMe)
<222> LOCATION: (39)..(39)
<220> FEATURE:
<221> NAME/KEY: 2'-OMe
<222> LOCATION: (40)..(43)

<400> SEQUENCE: 56
accagaatac aacaucaguc ggauaagcua caagatgatc cua        43

<210> SEQ ID NO 57
<211> LENGTH: 59
<212> TYPE: DNA
<213> ORGANISM: artificial sequence
<220> FEATURE:
<223> OTHER INFORMATION: sense sequence of S-TuD NC2
<220> FEATURE:
<221> NAME/KEY: 2'-OMe
<222> LOCATION: (1)..(59)

<400> SEQUENCE: 57
gacggcgcua ggaucaucaa cuaucgcgag uaucgacguc gaggcccaag uauucuggu        59

<210> SEQ ID NO 58
<211> LENGTH: 59
<212> TYPE: DNA
<213> ORGANISM: artificial sequence
<220> FEATURE:
<223> OTHER INFORMATION: antisense sequence of S-TuD NC2
<220> FEATURE:
<221> NAME/KEY: 2'-OMe
<222> LOCATION: (1)..(59)

<400> SEQUENCE: 58
accagaauac aacuaucgcg aguaucgacg ucgaggccca agaugauccu agcgccguc        59

<210> SEQ ID NO 59

```
<211> LENGTH: 44
<212> TYPE: DNA
<213> ORGANISM: artificial sequence
<220> FEATURE:
<223> OTHER INFORMATION: sense sequence (2)'
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(5)
<220> FEATURE:
<221> NAME/KEY: BNANC(NMe)
<222> LOCATION: (6)..(6)
<220> FEATURE:
<221> NAME/KEY: 2'-OMe
<222> LOCATION: (7)..(38)
<220> FEATURE:
<221> NAME/KEY: BNANC(NMe)
<222> LOCATION: (39)..(39)
<220> FEATURE:
<221> NAME/KEY: 2'-OMe
<222> LOCATION: (40)..(40)
<220> FEATURE:
<221> NAME/KEY: BNANC(NMe)
<222> LOCATION: (41)..(41)
<220> FEATURE:
<221> NAME/KEY: 2'-OMe
<222> LOCATION: (42)..(43)
<220> FEATURE:
<221> NAME/KEY: BNANC(NMe)
<222> LOCATION: (44)..(44)

<400> SEQUENCE: 59
taggatcauc aaacaaugug cagacuacug uaaaguautc tggt         44

<210> SEQ ID NO 60
<211> LENGTH: 44
<212> TYPE: DNA
<213> ORGANISM: artificial sequence
<220> FEATURE:
<223> OTHER INFORMATION: antisense sequence (2)'
<220> FEATURE:
<221> NAME/KEY: 2'-OMe
<222> LOCATION: (1)..(7)
<220> FEATURE:
<221> NAME/KEY: BNANC(NMe)
<222> LOCATION: (8)..(8)
<220> FEATURE:
<221> NAME/KEY: 2'-OMe
<222> LOCATION: (9)..(36)
<220> FEATURE:
<221> NAME/KEY: BNANC(NMe)
<222> LOCATION: (37)..(37)
<220> FEATURE:
<221> NAME/KEY: 2'-OMe
<222> LOCATION: (38)..(42)
<220> FEATURE:
<221> NAME/KEY: BNANC(NMe)
<222> LOCATION: (43)..(43)
<220> FEATURE:
<221> NAME/KEY: 2'-OMe
<222> LOCATION: (44)..(44)

<400> SEQUENCE: 60
accagaatac aaacaaugug cagacuacug uaaagatgau ccta         44

<210> SEQ ID NO 61
<211> LENGTH: 44
<212> TYPE: DNA
<213> ORGANISM: artificial sequence
<220> FEATURE:
<223> OTHER INFORMATION: sense sequence (7)'
<220> FEATURE:
<221> NAME/KEY: LNA
```

```
<222> LOCATION: (1)..(1)
<220> FEATURE:
<221> NAME/KEY: 2'-OMe
<222> LOCATION: (2)..(38)
<220> FEATURE:
<221> NAME/KEY: LNA
<222> LOCATION: (39)..(39)
<220> FEATURE:
<221> NAME/KEY: 2'-OMe
<222> LOCATION: (40)..(43)
<220> FEATURE:
<221> NAME/KEY: LNA
<222> LOCATION: (44)..(44)

<400> SEQUENCE: 61
taggaucauc aaacaaugug cagacuacug uaaaguautc uggt            44

<210> SEQ ID NO 62
<211> LENGTH: 44
<212> TYPE: DNA
<213> ORGANISM: artificial sequence
<220> FEATURE:
<223> OTHER INFORMATION: antisense sequence (7)'
<220> FEATURE:
<221> NAME/KEY: 2'-OMe
<222> LOCATION: (1)..(7)
<220> FEATURE:
<221> NAME/KEY: LNA
<222> LOCATION: (8)..(8)
<220> FEATURE:
<221> NAME/KEY: 2'-OMe
<222> LOCATION: (9)..(36)
<220> FEATURE:
<221> NAME/KEY: LNA
<222> LOCATION: (37)..(37)
<220> FEATURE:
<221> NAME/KEY: 2'-OMe
<222> LOCATION: (38)..(39)
<220> FEATURE:
<221> NAME/KEY: LNA
<222> LOCATION: (40)..(40)
<220> FEATURE:
<221> NAME/KEY: 2'-OMe
<222> LOCATION: (41)..(44)

<400> SEQUENCE: 62
accagaatac aaacaaugug cagacuacug uaaagatgat ccua            44

<210> SEQ ID NO 63
<211> LENGTH: 44
<212> TYPE: DNA
<213> ORGANISM: artificial sequence
<220> FEATURE:
<223> OTHER INFORMATION: sense sequence (8)'
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(5)
<220> FEATURE:
<221> NAME/KEY: BNANC(NMe)
<222> LOCATION: (6)..(6)
<220> FEATURE:
<221> NAME/KEY: 2'-OMe
<222> LOCATION: (7)..(8)
<220> FEATURE:
<221> NAME/KEY: BNANC(NMe)
<222> LOCATION: (9)..(9)
<220> FEATURE:
<221> NAME/KEY: 2'-OMe
<222> LOCATION: (10)..(35)
<220> FEATURE:
<221> NAME/KEY: BNANC(NMe)
<222> LOCATION: (36)..(36)
```

```
<220> FEATURE:
<221> NAME/KEY: 2'-OMe
<222> LOCATION: (37)..(37)
<220> FEATURE:
<221> NAME/KEY: BNANC(NMe)
<222> LOCATION: (38)..(38)
<220> FEATURE:
<221> NAME/KEY: BNANC(NMe)
<222> LOCATION: (39)..(39)
<220> FEATURE:
<221> NAME/KEY: 2'-OMe
<222> LOCATION: (40)..(40)
<220> FEATURE:
<221> NAME/KEY: BNANC(NMe)
<222> LOCATION: (41)..(41)
<220> FEATURE:
<221> NAME/KEY: 2'-OMe
<222> LOCATION: (42)..(43)
<220> FEATURE:
<221> NAME/KEY: BNANC(NMe)
<222> LOCATION: (44)..(44)

<400> SEQUENCE: 63
taggatcatc aaacaaugug cagacuacug uaaagtattc tggt                          44

<210> SEQ ID NO 64
<211> LENGTH: 44
<212> TYPE: DNA
<213> ORGANISM: artificial sequence
<220> FEATURE:
<223> OTHER INFORMATION: antisense sequence (8)'
<220> FEATURE:
<221> NAME/KEY: 2'-OMe
<222> LOCATION: (1)..(7)
<220> FEATURE:
<221> NAME/KEY: BNANC(NMe)
<222> LOCATION: (8)..(8)
<220> FEATURE:
<221> NAME/KEY: 2'-OMe
<222> LOCATION: (9)..(36)
<220> FEATURE:
<221> NAME/KEY: BNANC(NMe)
<222> LOCATION: (37)..(37)
<220> FEATURE:
<221> NAME/KEY: 2'-OMe
<222> LOCATION: (38)..(39)
<220> FEATURE:
<221> NAME/KEY: BNANC(NMe)
<222> LOCATION: (40)..(40)
<220> FEATURE:
<221> NAME/KEY: 2'-OMe
<222> LOCATION: (41)..(42)
<220> FEATURE:
<221> NAME/KEY: BNANC(NMe)
<222> LOCATION: (43)..(43)
<220> FEATURE:
<221> NAME/KEY: 2'-OMe
<222> LOCATION: (44)..(44)

<400> SEQUENCE: 64
accagaatac aaacaaugug cagacuacug uaaagatgat ccta                          44

<210> SEQ ID NO 65
<211> LENGTH: 44
<212> TYPE: DNA
<213> ORGANISM: artificial sequence
<220> FEATURE:
<223> OTHER INFORMATION: sense sequence (1)''
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(40)
<220> FEATURE:
```

```
<221> NAME/KEY: BNANC(NMe)
<222> LOCATION: (41)..(41)
<220> FEATURE:
<221> NAME/KEY: 2'-OMe
<222> LOCATION: (42)..(44)

<400> SEQUENCE: 65
taggaucauc aaacaaugug cagacuacug uaaaguauuc tggu          44

<210> SEQ ID NO 66
<211> LENGTH: 44
<212> TYPE: DNA
<213> ORGANISM: artificial sequence
<220> FEATURE:
<223> OTHER INFORMATION: antisense sequence (1)''
<220> FEATURE:
<221> NAME/KEY: 2'-OMe
<222> LOCATION: (1)..(7)
<220> FEATURE:
<221> NAME/KEY: BNANC(NMe)
<222> LOCATION: (8)..(8)
<220> FEATURE:
<221> NAME/KEY: 2'-OMe
<222> LOCATION: (9)..(39)
<220> FEATURE:
<221> NAME/KEY: BNANC(NMe)
<222> LOCATION: (40)..(40)
<220> FEATURE:
<221> NAME/KEY: 2'-OMe
<222> LOCATION: (41)..(44)

<400> SEQUENCE: 66
accagaatac aaacaaugug cagacuacug uaaagaugat ccua          44

<210> SEQ ID NO 67
<211> LENGTH: 40
<212> TYPE: DNA
<213> ORGANISM: artificial sequence
<220> FEATURE:
<223> OTHER INFORMATION: sense sequence (2)''
<220> FEATURE:
<221> NAME/KEY: 2'-OMe
<222> LOCATION: (1)..(6)
<220> FEATURE:
<221> NAME/KEY: BNANC(NMe)
<222> LOCATION: (7)..(7)
<220> FEATURE:
<221> NAME/KEY: 2'-OMe
<222> LOCATION: (8)..(36)
<220> FEATURE:
<221> NAME/KEY: BNANC(NMe)
<222> LOCATION: (37)..(37)
<220> FEATURE:
<221> NAME/KEY: 2'-OMe
<222> LOCATION: (38)..(38)
<220> FEATURE:
<221> NAME/KEY: BNANC(NMe)
<222> LOCATION: (39)..(39)
<220> FEATURE:
<221> NAME/KEY: 2'-OMe
<222> LOCATION: (40)..(40)

<400> SEQUENCE: 67
ggaucatcaa acaaugugca gacuacugua aaguatctg               40

<210> SEQ ID NO 68
<211> LENGTH: 40
<212> TYPE: DNA
<213> ORGANISM: artificial sequence
<220> FEATURE:
<223> OTHER INFORMATION: antisense sequence (2)''
<220> FEATURE:
<221> NAME/KEY: 2'-OMe
```

```
<222> LOCATION: (1)..(5)
<220> FEATURE:
<221> NAME/KEY: BNANC(NMe)
<222> LOCATION: (6)..(6)
<220> FEATURE:
<221> NAME/KEY: 2'-OMe
<222> LOCATION: (7)..(34)
<220> FEATURE:
<221> NAME/KEY: BNANC(NMe)
<222> LOCATION: (35)..(35)
<220> FEATURE:
<221> NAME/KEY: 2'-OMe
<222> LOCATION: (36)..(37)
<220> FEATURE:
<221> NAME/KEY: BNANC(NMe)
<222> LOCATION: (38)..(38)
<220> FEATURE:
<221> NAME/KEY: 2'-OMe
<222> LOCATION: (39)..(40)

<400> SEQUENCE: 68
cagaatacaa acaaugugca gacuacugua aagatgatcc                               40

<210> SEQ ID NO 69
<211> LENGTH: 40
<212> TYPE: DNA
<213> ORGANISM: artificial sequence
<220> FEATURE:
<223> OTHER INFORMATION: sense sequence (3)''
<220> FEATURE:
<221> NAME/KEY: 2'-OMe
<222> LOCATION: (1)..(6)
<220> FEATURE:
<221> NAME/KEY: BNANC(NMe)
<222> LOCATION: (7)..(7)
<220> FEATURE:
<221> NAME/KEY: 2'-OMe
<222> LOCATION: (8)..(38)
<220> FEATURE:
<221> NAME/KEY: BNANC(NMe)
<222> LOCATION: (39)..(39)
<220> FEATURE:
<221> NAME/KEY: 2'-OMe
<222> LOCATION: (40)..(40)

<400> SEQUENCE: 69
ggaucatcaa acaaugugca gacuacugua aaguauuctg                               40

<210> SEQ ID NO 70
<211> LENGTH: 40
<212> TYPE: DNA
<213> ORGANISM: artificial sequence
<220> FEATURE:
<223> OTHER INFORMATION: antisense sequence (3)''
<220> FEATURE:
<221> NAME/KEY: 2'-OMe
<222> LOCATION: (1)..(5)
<220> FEATURE:
<221> NAME/KEY: BNANC(NMe)
<222> LOCATION: (6)..(6)
<220> FEATURE:
<221> NAME/KEY: 2'-OMe
<222> LOCATION: (7)..(37)
<220> FEATURE:
<221> NAME/KEY: BNANC(NMe)
<222> LOCATION: (38)..(38)
<220> FEATURE:
<221> NAME/KEY: 2'-OMe
<222> LOCATION: (39)..(40)

<400> SEQUENCE: 70
cagaatacaa acaaugugca gacuacugua aagaugatcc                               40
```

```
<210> SEQ ID NO 71
<211> LENGTH: 36
<212> TYPE: DNA
<213> ORGANISM: artificial sequence
<220> FEATURE:
<223> OTHER INFORMATION: sense sequence (4)''
<220> FEATURE:
<221> NAME/KEY: 2'-OMe
<222> LOCATION: (1)..(1)
<220> FEATURE:
<221> NAME/KEY: BNANC(NMe)
<222> LOCATION: (2)..(2)
<220> FEATURE:
<221> NAME/KEY: 2'-OMe
<222> LOCATION: (3)..(4)
<220> FEATURE:
<221> NAME/KEY: BNANC(NMe)
<222> LOCATION: (5)..(5)
<220> FEATURE:
<221> NAME/KEY: 2'-OMe
<222> LOCATION: (6)..(31)
<220> FEATURE:
<221> NAME/KEY: BNANC(NMe)
<222> LOCATION: (32)..(32)
<220> FEATURE:
<221> NAME/KEY: 2'-OMe
<222> LOCATION: (33)..(34)
<220> FEATURE:
<221> NAME/KEY: BNANC(NMe)
<222> LOCATION: (35)..(35)
<220> FEATURE:
<221> NAME/KEY: 2'-OMe
<222> LOCATION: (36)..(36)

<400> SEQUENCE: 71
atcatcaaac aaugugcaga cuacuguaaa gtautc                                  36

<210> SEQ ID NO 72
<211> LENGTH: 36
<212> TYPE: DNA
<213> ORGANISM: artificial sequence
<220> FEATURE:
<223> OTHER INFORMATION: antisense sequence (4)''
<220> FEATURE:
<221> NAME/KEY: 2'-OMe
<222> LOCATION: (1)..(3)
<220> FEATURE:
<221> NAME/KEY: BNANC(NMe)
<222> LOCATION: (4)..(4)
<220> FEATURE:
<221> NAME/KEY: 2'-OMe
<222> LOCATION: (5)..(32)
<220> FEATURE:
<221> NAME/KEY: BNANC(NMe)
<222> LOCATION: (33)..(33)
<220> FEATURE:
<221> NAME/KEY: 2'-OMe
<222> LOCATION: (34)..(36)

<400> SEQUENCE: 72
gaatacaaac aaugugcaga cuacuguaaa gatgau                                  36

<210> SEQ ID NO 73
<211> LENGTH: 36
<212> TYPE: DNA
<213> ORGANISM: artificial sequence
<220> FEATURE:
<223> OTHER INFORMATION: sense sequence (5)''
<220> FEATURE:
<221> NAME/KEY: 2'-OMe
<222> LOCATION: (1)..(1)
<220> FEATURE:
<221> NAME/KEY: BNANC(NMe)
<222> LOCATION: (2)..(2)
<220> FEATURE:
```

```
<221> NAME/KEY: 2'-OMe
<222> LOCATION: (3)..(34)
<220> FEATURE:
<221> NAME/KEY: BNANC(NMe)
<222> LOCATION: (35)..(35)
<220> FEATURE:
<221> NAME/KEY: 2'-OMe
<222> LOCATION: (36)..(36)

<400> SEQUENCE: 73
atcaucaaac aaugugcaga cuacuguaaa guautc                                   36

<210> SEQ ID NO 74
<211> LENGTH: 36
<212> TYPE: DNA
<213> ORGANISM: artificial sequence
<220> FEATURE:
<223> OTHER INFORMATION: antisense sequence (5)''
<220> FEATURE:
<221> NAME/KEY: 2'-OMe
<222> LOCATION: (1)..(3)
<220> FEATURE:
<221> NAME/KEY: BNANC(NMe)
<222> LOCATION: (4)..(4)
<220> FEATURE:
<221> NAME/KEY: 2'-OMe
<222> LOCATION: (5)..(32)
<220> FEATURE:
<221> NAME/KEY: BNANC(NMe)
<222> LOCATION: (33)..(33)
<220> FEATURE:
<221> NAME/KEY: 2'-OMe
<222> LOCATION: (34)..(36)

<400> SEQUENCE: 74
gaatacaaac aaugugcaga cuacuguaaa gatgau                                   36

<210> SEQ ID NO 75
<211> LENGTH: 30
<212> TYPE: DNA
<213> ORGANISM: artificial sequence
<220> FEATURE:
<223> OTHER INFORMATION: psiCHECK2-T200c-3p-s

<400> SEQUENCE: 75
tcgagtccat cattacccgg cagtattagc                                          30

<210> SEQ ID NO 76
<211> LENGTH: 30
<212> TYPE: DNA
<213> ORGANISM: artificial sequence
<220> FEATURE:
<223> OTHER INFORMATION: psiCHECK2-T200c-3p-a

<400> SEQUENCE: 76
ggccgctaat actgccgggt aatgatggac                                          30

<210> SEQ ID NO 77
<211> LENGTH: 75
<212> TYPE: DNA
<213> ORGANISM: artificial sequence
<220> FEATURE:
<223> OTHER INFORMATION: psiCHECK2-T199a-3px3-s

<400> SEQUENCE: 77
tcgagtaacc aatgtgcaga ctactgtata accaatgtgc agactactgt ataaccaatg         60
tgcagactac tgtgc                                                          75
```

```
<210> SEQ ID NO 78
<211> LENGTH: 75
<212> TYPE: DNA
<213> ORGANISM: artificial sequence
<220> FEATURE:
<223> OTHER INFORMATION: psiCHECK2-T199a-3px3-a

<400> SEQUENCE: 78
ggccgcacag tagtctgcac attggttata cagtagtctg cacattggtt atacagtagt    60
ctgcacattg gttac                                                    75

<210> SEQ ID NO 79
<211> LENGTH: 29
<212> TYPE: DNA
<213> ORGANISM: artificial sequence
<220> FEATURE:
<223> OTHER INFORMATION: psiCHECK2-T21-5p-s

<400> SEQUENCE: 79
tcgagtcaac atcagtctga taagctagc                                     29

<210> SEQ ID NO 80
<211> LENGTH: 29
<212> TYPE: DNA
<213> ORGANISM: artificial sequence
<220> FEATURE:
<223> OTHER INFORMATION: psiCHECK2-T21-5p-a

<400> SEQUENCE: 80
ggccgctagc ttatcagact gatgttgac                                     29
```

STRUCTURALLY-ENHANCED MIRNA INHIBITOR S-TUD

TECHNICAL FIELD

Statement Regarding Sequence Listing

The Sequence Listing associated with this application is provided in text format in lieu of a paper copy, and is hereby incorporated by reference into the specification. The name of the text file containing the Sequence Listing is 910248_401USPC_SEQUENCE_LISTING.txt. The text file is 41.2 KB, was created on Feb. 13, 2020, and is being submitted electronically via EFS-Web.

The present invention relates to a structurally-enhanced miRNA inhibitor.

BACKGROUND ART

MicroRNA (miRNA) is an endogenously-expressed small (about 20 to 24 nucleotides) regulatory non-coding RNA, which regulates the expression of numerous target genes at post-transcription levels as a component of an RNA-induced silencing complex (RISC). When a certain miRNA and a target sequence thereof in an mRNA are fully complementary, the miRNA induces cleavage of the mRNA to cause a rapid decrease in the mRNA level.

Some of the inventors have recently developed miRNA inhibitors for efficiently inhibiting miRNAs, vectors for expressing the inhibitors in cells, methods for constructing the vectors, and methods for inhibiting miRNAs using the inhibitors or vectors (Japanese Patent No. 4936343=Patent Literature 1).

CITATION LIST

Patent Literature

[PTL 1] Japanese Patent No. 4936343

SUMMARY OF INVENTION

Solution to Problem

The conventional miRNA inhibitor described in Patent Literature 1 (synthetic Tough Decoy, S-TuD) has drawn attention as a nucleic acid that inhibits miRNA activity at a low concentration, but the physical properties after double-strand formation, have room for improvement in view of the structural characteristics thereof. The inventors, after diligent research, have established stable mass production of S-TuDs and physical property testing method by employing a method of partially substituting a double-stranded region with a modified nucleic acid that improves the hybridization capability as a method of strengthening the double-strand to complete the present invention.

Thus, the present invention provides the following.

(1) An miRNA inhibiting complex comprising an RNA or an analog thereof, the miRNA inhibiting complex comprising at least one double-stranded structure and an miRNA binding sequence, wherein two strands of the miRNA binding sequence are each bound to one of two strands on at least one end of the double-stranded structure, and wherein the miRNA inhibiting complex comprises at least one bridged nucleic acid (BNA).

(2) The complex of item 1, wherein the BNA comprises a BNA that is bridged via at least one atom selected from the group consisting of oxygen and carbon on the position 2' side and via at least one atom selected from the group consisting of carbon and nitrogen and carbon on the position 4' side.

(3) The complex of item 1 or 2, wherein the BNA comprises a 2',4' substituted bridged nucleic acid represented by

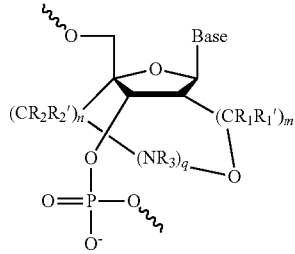

BNA-1 wherein $R_1$, $R_1'$, $R_2$, $R_2'$, and $R_3$ each independently represent a group selected from the group consisting of a hydrogen atom, a substituted or unsubstituted alkyl group, a substituted or unsubstituted alkenyl group, a substituted or unsubstituted cycloalkyl group, a substituted or unsubstituted aryl group, a substituted or unsubstituted aralkyl group, a substituted or unsubstituted acyl group, a substituted or unsubstituted sulfonyl group, a substituted or unsubstituted silyl group, and a functional molecule unit substituent, m is an integer from 0 to 2, Base represents a group selected from the group consisting of an adeninyl group, a thyminyl group, a uracilyl group, an inosinyl group, a cytosinyl group, a guaninyl group, and a methylcytosinyl group, n is an integer from 1 to 3, and q is an integer that is 0 or 1.

(4) The complex of any one of items 1 to 3, wherein the BNA comprises a 2',4' substituted bridged nucleic acid represented by

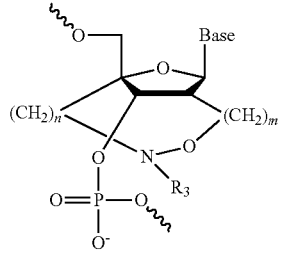

BNA-2 wherein $R_3$ represents a group selected from the group consisting of a hydrogen atom, an alkyl group, an alkenyl group, a cycloalkyl group, an aryl group, an aralkyl group, an acyl group, a sulfonyl group, a silyl group, and a functional molecule unit substituent, Base represents a group selected from the group consisting of an adeninyl group, a thyminyl group, a uracilyl group, an inosinyl group, a cytosinyl group, a guaninyl group, and a methylcytosinyl group, m is an integer from 0 to 2, and n is an integer from 1 to 3.

(5) The complex of any one of items 1 to 4, wherein the BNA comprises

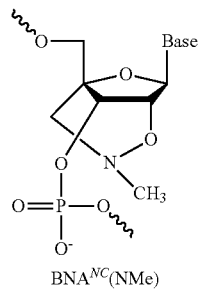

BNA$^{NC}$(NMe)

or a 2',4'-methano bridged nucleic acid (LNA).
(6) The complex of any one of items 1 to 5, wherein the BNA is BNA$^{NC}$(NMe).
(7) The complex of any one of items 1 to 6, wherein the BNA is comprised in at least one of the strands of the double-stranded structure moiety and at least one strand of complementary strands of the miRNA binding sequence.
(8) The complex of any one of items 1 to 7, wherein the BNA is comprised in at least one of the strands of the double-stranded structure moiety.
(9) The complex of any one of items 1 to 8, wherein the BNA is comprised in both strands of the double-stranded structure moiety.
(10) The complex of any one of items 1 to 9, wherein two or more of the BNA are comprised.
(11) The complex of any one of items 1 to 10, wherein four or more of the BNA are comprised.
(12) The complex of any one of items 1 to 11, wherein six or more of the BNA are comprised.
(13) The complex of any one of items 1 to 12, wherein the complex comprises two or more of the double-stranded structures, wherein strands comprising the miRNA binding sequence are each bound to one of two strands on one end of a first double-stranded structure of the double-stranded structure, and the other ends of the strands are each bound to one of two strands of a second double-stranded structure of the two or more of the double-stranded structures, so that the strands are sandwiched between the two or more of the double-stranded structures.
(14) The complex of any one of items 1 to 13, wherein an end of two strands comprising the miRNA binding sequence is bound via a linker.
(15) The complex of item 14, wherein a length of the linker is 1 to 5 bases long.
(16) The complex of any one of items 1 to 15, wherein the double-stranded structure is at least 6 bases long.
(17) The complex of any one of items 1 to 16, wherein the double-stranded structure is at least 8 bases long.
(18) The complex of any one of items 1 to 17, wherein the double-stranded structure is at least 10 bases long.
(19) The complex of any one of items 1 to 18, wherein the double-stranded structure is at least 15 bases long.
(20) The complex of any one of items 1 to 19, wherein the double-stranded structure is at least 18 bases long.
(21) The complex of any one of items 1 to 20, wherein the double-stranded structure is 50 bases long or less.
(22) The complex of any one of items 1 to 21, comprising 2 to 5 miRNA binding sequences.
(23) The complex of any one of items 1 to 22, comprising two miRNA binding sequences.

(24) The complex of any one of items 1 to 23, comprising the following structure represented by

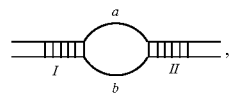

(C)

wherein I and II of the structure are double-stranded structures, and each of a and b of the structure comprises an miRNA binding sequence.
(24A) The complex of any one of items 1 to 24, wherein an end of each strand of the double-stranded structure binds to each other to form a single stranded nucleic acid.
(24B) The complex of any one of items 1 to 24 and 24A, comprised of a straight single stranded RNA or an analog thereof.
(24C) The complex of any one of items 1 to 24, 24A and 24B, wherein the complex comprises a second multi-stranded structure selected from double and quadruple stranded structures, wherein ends of two strands comprising the miRNA binding sequence are each bound to one of two strands on one end of the double-stranded structure via a 1 to 5 base linker, and the other ends of the two strands comprising the miRNA binding sequence are each bound to one of two strands on one end of the second multi-stranded structure via a 1 to 5 base linker, so that the strands are sandwiched by the double-stranded structure and the second multi-stranded structure.
An miRNA inhibiting complex, wherein two strands comprising the miRNA binding sequence each comprise an miRNA binding sequence, while there are two strands comprising an miRNA binding sequence.
(24D) The complex of any one of items 1 to 24, 24A, 24B, and 24C, wherein two strands comprising the miRNA binding sequence each comprise an miRNA binding sequence, while there are two strands comprising an miRNA binding sequence.
(25) An RNA constituting the complex of any one of items 1 to 24, 24A, 24B, 24C and 24D, or an analog thereof.
(26) A method of manufacturing the complex of any one of items 1 to 24, 24A, 24B, 24C and 24D or the RNA or an analog thereof of item 25, comprising:
A) synthesizing a protected entity of a single strand of an RNA of interest or an analog thereof and a protected entity of a complement thereof by chemical synthesis using a ribonucleic acid and a BNA;
B) deprotecting each of the protected entity of the single strand and the complement thereof, which have been generated; and optionally
C) placing each of the single strands that has been deprotected under a double-strand forming condition to form a double strand.
(27) A medicament comprising the complex of any one of items 1 to 24, 24A, 24B, 24C, and 24D.
(27A) The complex of any one of items 1 to 24, 24A, 24B, 24C, and 24D for use as a medicament.
(27B) A method of treating or preventing a disease or disorder, comprising administering the complex of any one of items 1 to 24, 24A, 24B, 24C, and 24D to a subject in need thereof.

In each of the above items, inventions combining any two or more inventions described in each item that is dependent from the same item are already intended in the invention described in a superordinate item from which they are dependent. The present specification is intended for any inventive element described herein and any combination thereof. The present specification is also intended for the above inventions, which excludes any element described herein or any combination thereof. When a specific embodiment is described herein as a preferred embodiment, the present specification discloses not only such an embodiment, but also inventions that exclude such an embodiment from a more superordinate invention disclosed herein including such an embodiment.

Advantageous Effects of Invention

The improved S-TuD of the present invention is found to have stable miRNA inhibiting activity in relative to conventional S-TuDs and have impurities unexpectedly reduced to a pharmaceutical grade without purification. By strengthening the double-strand, cost can be reduced as a STEM region shortened S-TuD with the same activity. The improved S-TuD of the present invention also had significantly improved biological activity in relative to conventional S-TuDs.

BRIEF DESCRIPTION OF DRAWINGS

FIG. 1B shows a comparison of an S strand, AS strand, and double-strand, which were analyzed by reverse phase HPLC (RP-HPLC) analysis (C18 reverse phase ion pairing HPLC with XBridge column) of a conventional S-TuD.

FIG. 2A shows the structures of the oligonucleotides that were used. The top row shows the original oligonucleotide. The second row and thereafter show modified oligonucleotides, which are, from the top, (1) C,U: 2'-F-C, 2'-F-U, (2) T: BNA-T (T of BNA$^{NC}$(NMe) inserted at 4 places on one of the strands), (3) T: BNA-T (T of BNA$^{NC}$(NMe) inserted at 2 places each on both strands), (4) T: BNA-T A: BNA-A (T and A of BNA$^{NC}$(NMe) inserted at 4 places each to be paired on both strands), (5) T: BNA-T A: BNA-A (10 bases) (stem I of (4) shortened to 10 bp). The sequences used herein represents a 2'-OCH$_3$(2'-OMe) form unless especially noted otherwise. Fluoro form (2'-F form) is depicted by a double underline. An LNA, when present, is indicated with a slanted double underline. Modified nucleic acids (BNA$^{NC}$(NMe)) are indicated in lower case. Phosphorothioate structures are indicated by an underline. The same applies hereinafter.

FIG. 2B shows the structures of oligonucleotides that were used. The sequences shown are the following: (1)' S-TuD199a-3p-1_18-pf-S10; (1)" S-TuD199a-3p-1_18-pf-S10-BT4; (2)" S-TuD199a-3p-1_18-pf-S8-BT6; (3)" S-TuD199a-3p-1_18-pf-S8-BT4; (4)" S-TuD199a-3p-1_18-pf-S6-BT6; and (5)" S-TuD199a-3p-1_18-pf-S6-BT4.

FIG. 4-2 shows results of an miR-199a-3p reporter assay for the oligoes in FIG. 4-1. The bars indicate the ratio of control reporter activity and miR-199a-3p reporter inhibiting activity. The bar is higher for a higher inhibitory effect of S-TuD.

FIG. 6 shows the structures of S-TuDs (S-TuD199a-3p) that were used in the experiment for substitution into an MBS region. The top row shows the structure of the original S-TuD199a-3p-1_18-pf. The second row and thereafter show the modified S-TuDs of the present invention, (16) S-TuD-miR-199a-3p-1_18-pf-L18B6-2, (22) S-TuD-miR-199a-3p-1_18-pf-L18B6-2-MBSB1 (complementary sequence to seed region includes BNA$^{NC}$(NMe)), (23) S-TuD-miR-199a-3p-1_18-pf-L18B6-2-MBSB2 (complementary sequence to non-seed region includes BNA$^{NC}$(NMe)), and (24) S-TuD-miR-199a-3p-1_18-pf-L18B6-3-MBSB2 (complementary sequence to non-seed region includes BNA$^{NC}$(NMe)). Modified nucleic acids are indicated in lower case.

FIG. 7 shows the structures of S-TuDs that were used in the experiment for substitution into an MBS region. The Figure shows from the top, in order, (17) S-TuD199a-3p-1_18-pf-S10-BT6-MBSB1 (complementary sequence to seed region includes BNA$^{NC}$(NMe)), (18) S-TuD199a-3p-1_18-pf-S10-BT6-MBSB2 (complementary sequence to non-seed region includes BNA$^{NC}$(NMe)), (23)-(1) S-TuD-miR-199a-3p-1_18-pf-L18B6-2-PS1 (complementary sequence to non-seed region includes BNA$^{NC}$(NMe)), (23)-(2) S-TuD-miR-199a-3p-1_18-pf-L18B6-2-PS2 (complementary sequence to non-seed region includes BNA$^{NC}$(NMe)), (23)-(3) S-TuD-miR-199a-3p-1_18-pf-L18B6-2-PS3 (complementary sequence to non-seed region includes BNA$^{NC}$(NMe)). The underlines indicate a phosphorothioate structure.

FIGS. 8-1 and 8-2 show results of a partial substitution of an MBS region with BNA$^{NC}$(NMe). As shown in FIGS. 8-1 and 8-2, it is possible to obtain a structure, which is observed to have a 3-fold or greater improvement in inhibitory activity compared to the original S-TuD. It was critical to insert BNA$^{NC}$(NMe) into a portion of a non-seed region of an MBS region.

FIGS. 8-1 and 8-2 show results of a partial substitution of an MBS region with BNA$^{NC}$(NMe). As shown in FIGS. 8-1 and 8-2, it is possible to obtain a structure, which is observed to have a 3-fold or greater improvement in inhibitory activity compared to the original S-TuD. It was critical to insert BNA$^{NC}$(NMe) into a portion of a non-seed region of an MBS region.

FIG. 10 shows the structures of S-TuDs that were used in an experiment to study the effect of shortening the STEM region and insertion of BNA$^{NC}$(NMe) into an MBS region. The top row shows the original structure of S-TuD199a-3p. The second row and thereafter shows (16) S-TuD-miR-199a-3p-1_18-pf-L18B6-2, (1)'S-TuD199a-3p-1_18-pf-S10, (6)'S-TuD199a-3p-1_18-pf-S10-BT6, (17) S-TuD199a-3p-1_18-pf-S10-BT6-MBSB1 (complementary sequence to seed region includes BNA$^{NC}$(NMe)), and (18) S-TuD199a-3p-1_18-pf-S10-BT6-MBSB2 (complementary sequence to non-seed region includes BNA$^{NC}$(NMe)), respectively.

FIGS. 11-1 and 11-2 show results (3xT199a-3p/UT (%)) for individual S-TuDs at 100 pM and 300 pM. FIG. 11-1 shows results at 100 pM. The effect of a BNA$^{NC}$(NMe) modification was examined for short types. The original type and long type Stem-BNA$^{NC}$(NMe) modification (16) were added to the comparison. Compared to short type-BNA$^{NC}$(NMe) modification free (1)', the effect significantly increased for (6)' provided with a BNA$^{NC}$(NMe) modification to the stem portion. The effect did not increase for (17) with an additional BNA$^{NC}$(NMe) modification to a seed corresponding site. However, the effect further increased for (18) provided with a BNA$^{NC}$(NMe) modification to a non-seed corresponding site, so that the effect was equal to or greater than (16). It was found that there is an increased effect for short types depending on the BNA$^{NC}$(NMe) modification site in MBS.

Figures 1, 4:
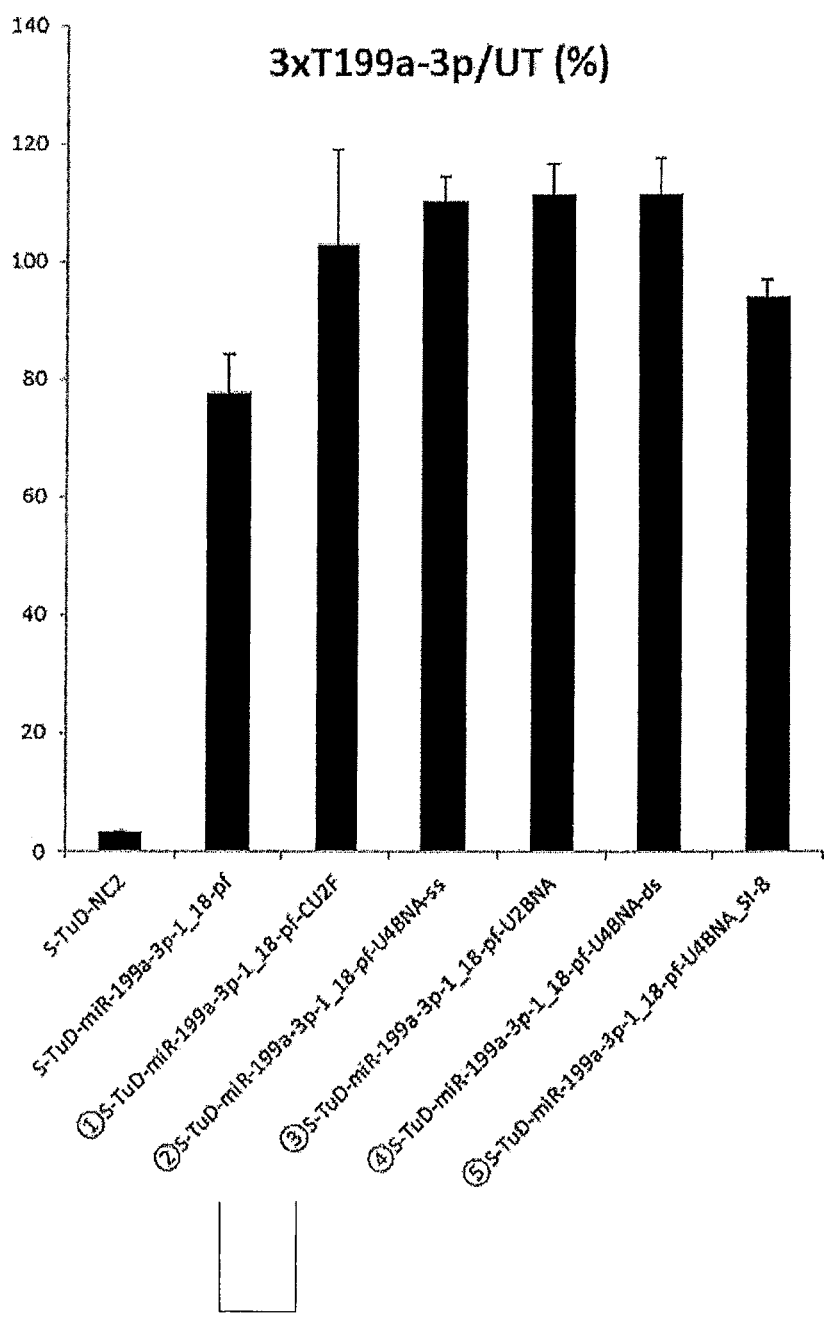
FIG. 4-1 shows the structure of oligoes used.
Figures 1, 8:
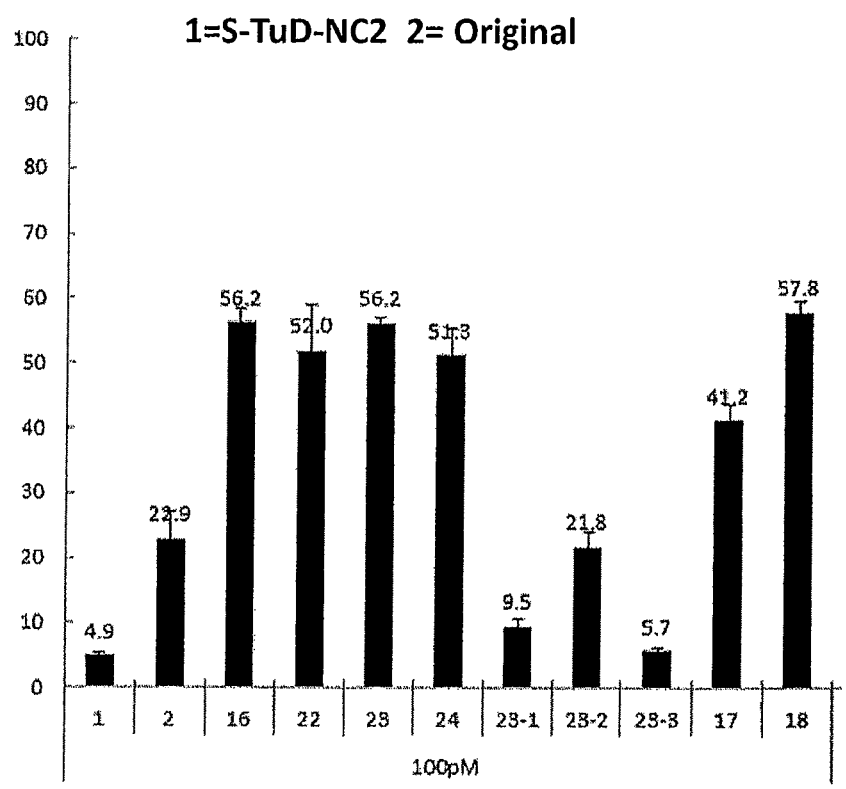
Figures 2, 8:
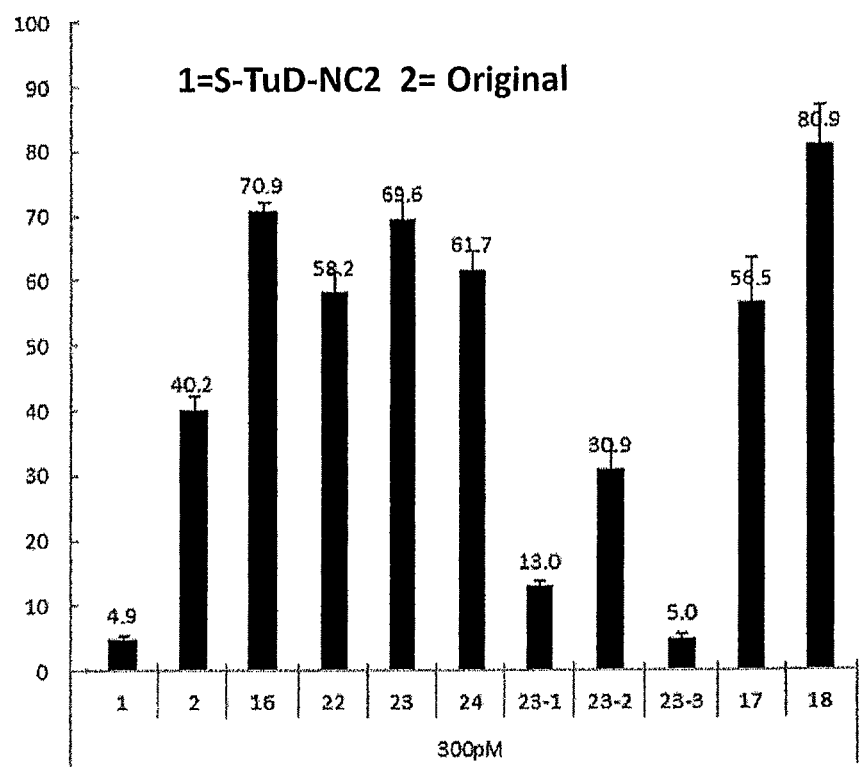
Figures 1, 11:
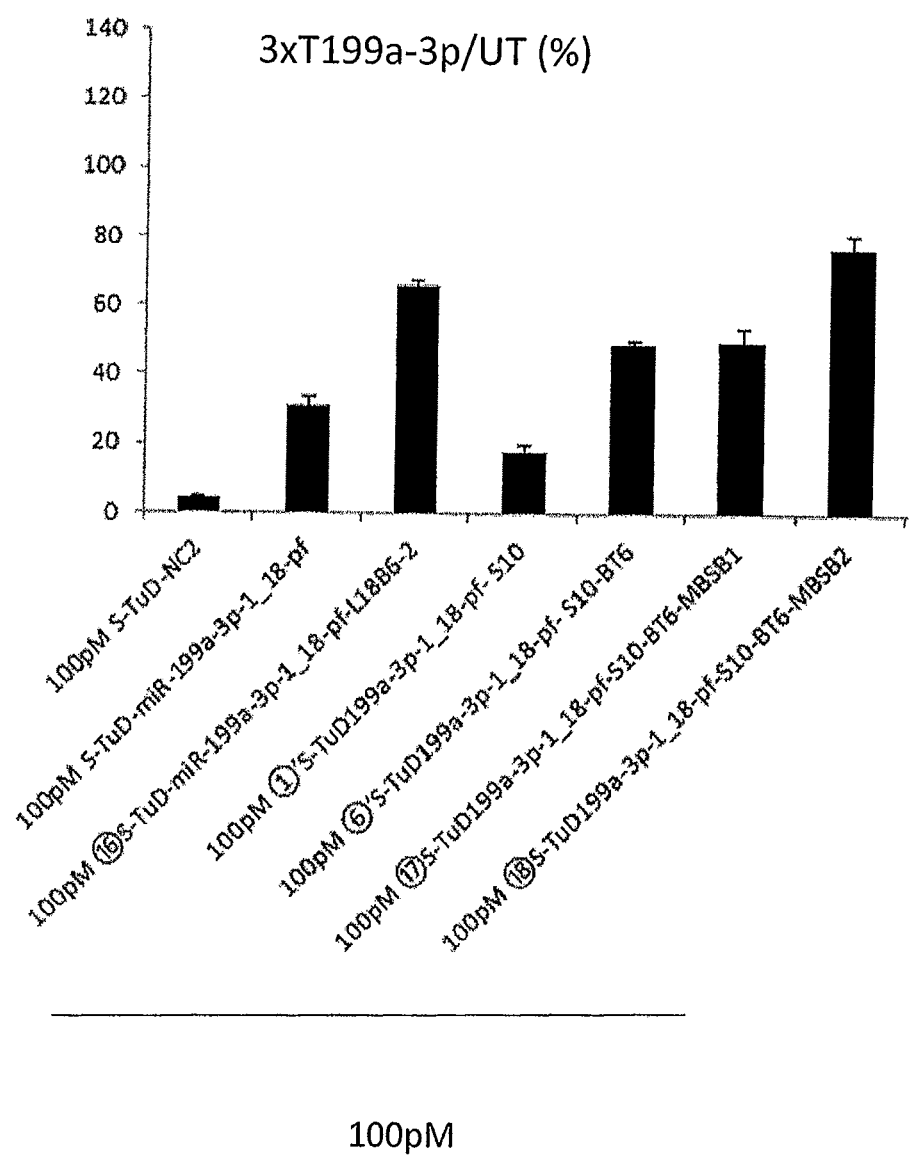
Figures 2, 11:
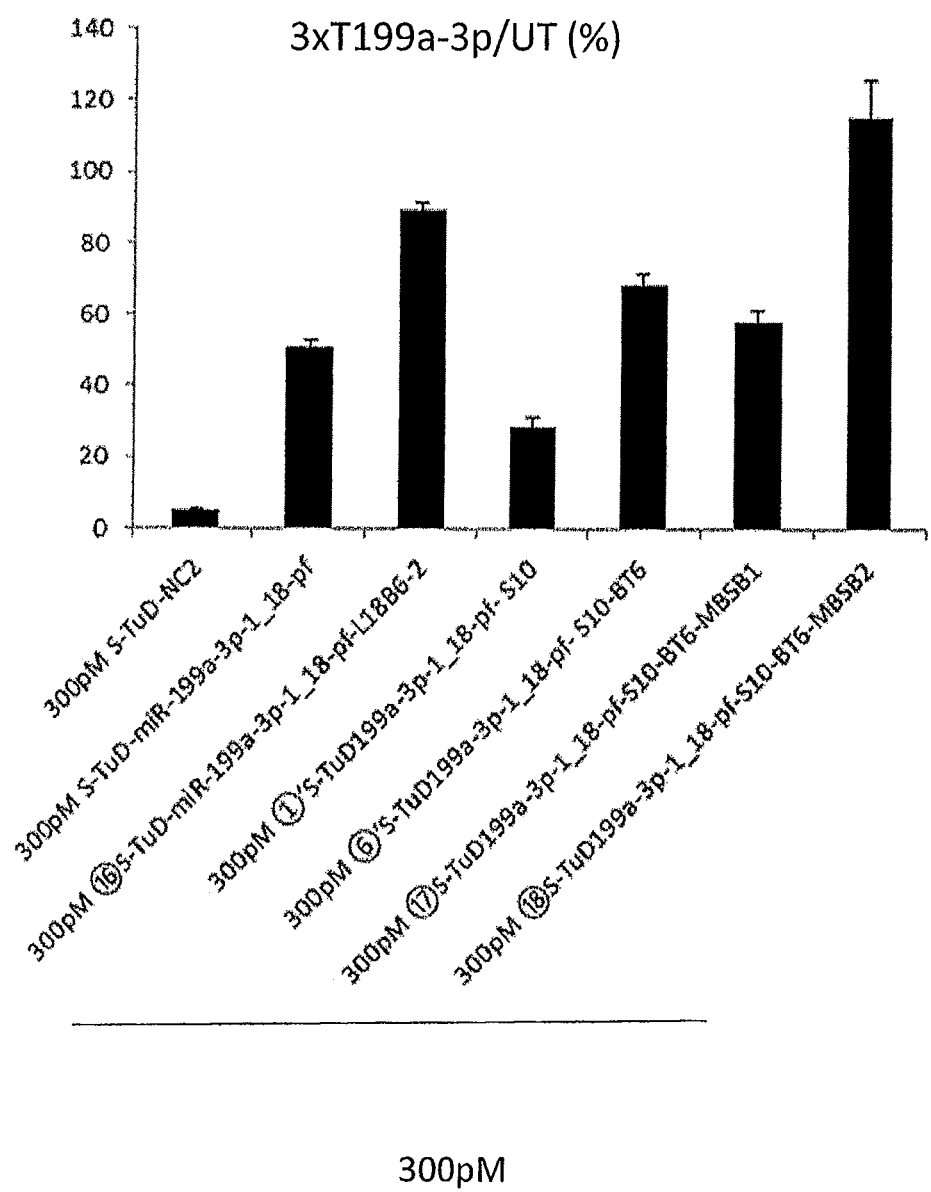

FIGS. 11-1 and 11-2 show results (3xT199a-3p/UT (%)) for individual S-TuDs at 100 pM and 300 pM. FIG. 11-2 shows results at 300 pM. The effect of a BNA$^{NC}$(NMe) modification was examined for short types. The original type and long type Stem-BNA$^{NC}$(NMe) modification (16) were added to the comparison. Compared to short type-BNA$^{NC}$(NMe) modification free (1)', the effect significantly increased for (6)' provided with a BNA$^{NC}$(NMe) modification to the stem portion. The effect did not increase for (17) provided with an additional BNA$^{NC}$(NMe) modification to a seed corresponding site. However, the effect further increased for (18) provided with a BNA$^{NC}$(NMe) modification to a non-seed corresponding site, so that the effect was equal to or greater than (16). It was found that there is an increased effect for short types depending on the BNA$^{NC}$(NMe) modification site in MBS.

FIG. 12 shows the structures of modified S-TuDs that were used in the serum stability experiment. The top row is the original structure. The second row and thereafter shows (16) S-TuD-miR-199a-3p-1_18-pf-L18B6-2, (23) S-TuD-miR-199a-3p-1_18-pf-L18B6-2-MBSB2 (complementary sequence to non-seed region includes BNA$^{NC}$(NMe)), (23)-(1) S-TuD-miR-199a-3p-1_18-pf-L18B6-2-PS1 (complementary sequence to non-seed region includes BNA$^{NC}$(NMe)), (23)-(2) S-TuD-miR-199a-3p-1_18-pf-L18B6-2-PS2 (complementary sequence to non-seed region includes BNA$^{NC}$(NMe)), and (23)-(3) S-TuD-miR-199a-3p-1_18-pf-L18B6-2-PS3 (complementary sequence to non-seed region includes BNA$^{NC}$(NMe)), respectively.

FIG. 13 shows the structures of modified S-TuDs that were used in a serum stability experiment. The Figure shows, from the top, (1)'S-TuD199a-3p-1_18-pf-S10, (6)'S-TuD199a-3p-1_18-pf-S10-BT6, (17) S-TuD199a-3p-1_18-pf-S10-BT6-MBSB1 (complementary sequence to seed region includes BNA$^{NC}$(NMe)), and (18) S-TuD199a-3p-1_18-pf-S10-BT6-MBSB2 (complementary sequence to non-seed region includes BNA$^{NC}$(NMe)).

FIG. 14 shows electropherograms after mouse serum treatment. 0h, 48h, 72h, and 96h indicate the time treated in 37° C. mouse serum. The figures in the top row show, from the left, the original structure, (16) S-TuD-miR-199a-3p-1_18-pf-L18B6-2, and (23) S-TuD-miR-199a-3p-1_18-pf-L18B6-2-MBSB2 (complementary sequence to non-seed region includes BNA$^{NC}$(NMe)), and the figures in the bottom row show, from the left, (23)-(1) S-TuD-miR-199a-3p-1_18-pf-L18B6-2-PS1 (complementary sequence to non-seed region includes BNA$^{NC}$(NMe)), (23)-(2) S-TuD-miR-199a-3p-1_18-pf-L18B6-2-PS2 (complementary sequence to non-seed region includes BNA$^{NC}$(NMe)), and (23)-(3) S-TuD-miR-199a-3p-1_18-pf-L18B6-2-PS3 (complementary sequence to non-seed region includes BNA$^{NC}$(NMe)).

FIG. 15 shows electropherograms. The figures on the top row show, from the left, (1)'S-TuD199a-3p-1_18-pf-S10 and (6)'S-TuD199a-3p-1_18-pf-S10-BT6, and the figures in the bottom row show, from the left, (17) S-TuD199a-3p-1_18-pf-S10-BT6-MBSB1 (complementary sequence to seed region includes BNA$^{NC}$(NMe)) and (18) S-TuD199a-3p-1_18-pf-S10-BT6-MBSB2 (complementary sequence to non-seed region includes BNA$^{NC}$(NMe)).

Figure 16:
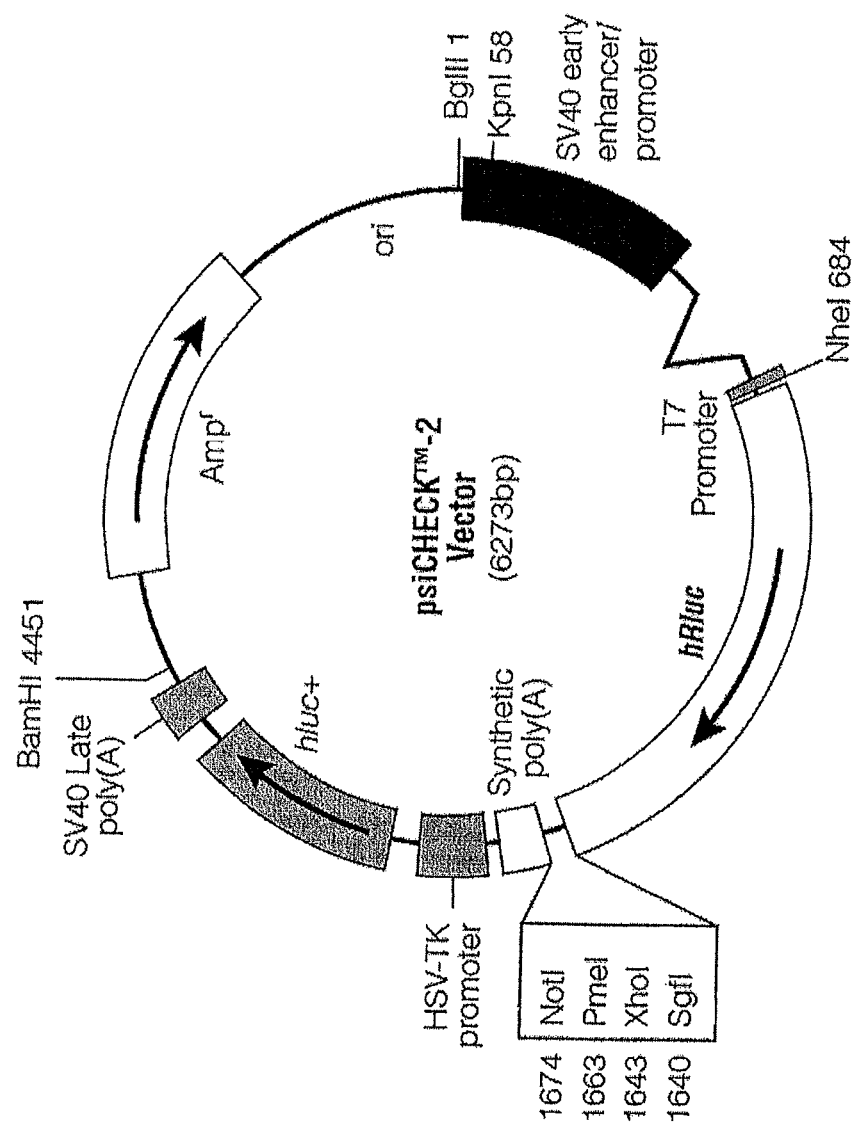

FIG. 16 shows a schematic diagram of a luciferase reporter vector used in the Examples.

FIG. 17 shows sequence information of psiCHECK2-T200c-3p-s, psiCHECK2-T200c-3p-a, psiCHECK2-T199a-3px3-s, psiCHECK2-T199a-3px3-a, psiCHECK2-T21-5p-s, and psiCHECK2-T21-5p-a that were used for luciferase reporter vectors. The sequences (SEQ ID NOs: 75-80) are all DNAs without any modification.

FIG. 18 shows the sequence of S-TuD-NC2 that was used in the Examples.

FIG. 19 shows the structures of S-TuD targeting miR-200c which were used in the universality confirmation experiment. The figure shows, from the top, each of (41) S-TuD-200c-1_22-pf, (42) S-TuD-200c-1_22-pf-L18B6, (43) S-TuD-200c-1_22-pf-L18B6-MBSB1 (complementary sequence to seed region includes BNA$^{NC}$(NMe)), (44) S-TuD-200c-1_22-pf-L18B6-MBSB2 (complementary sequence to non-seed region includes BNA$^{NC}$(NMe)), and (45) S-TuD-200c-1_22-pf-S10-BT6-MBSB2 (complementary sequence to non-seed region includes BNA$^{NC}$(NMe)).

Figure 20:
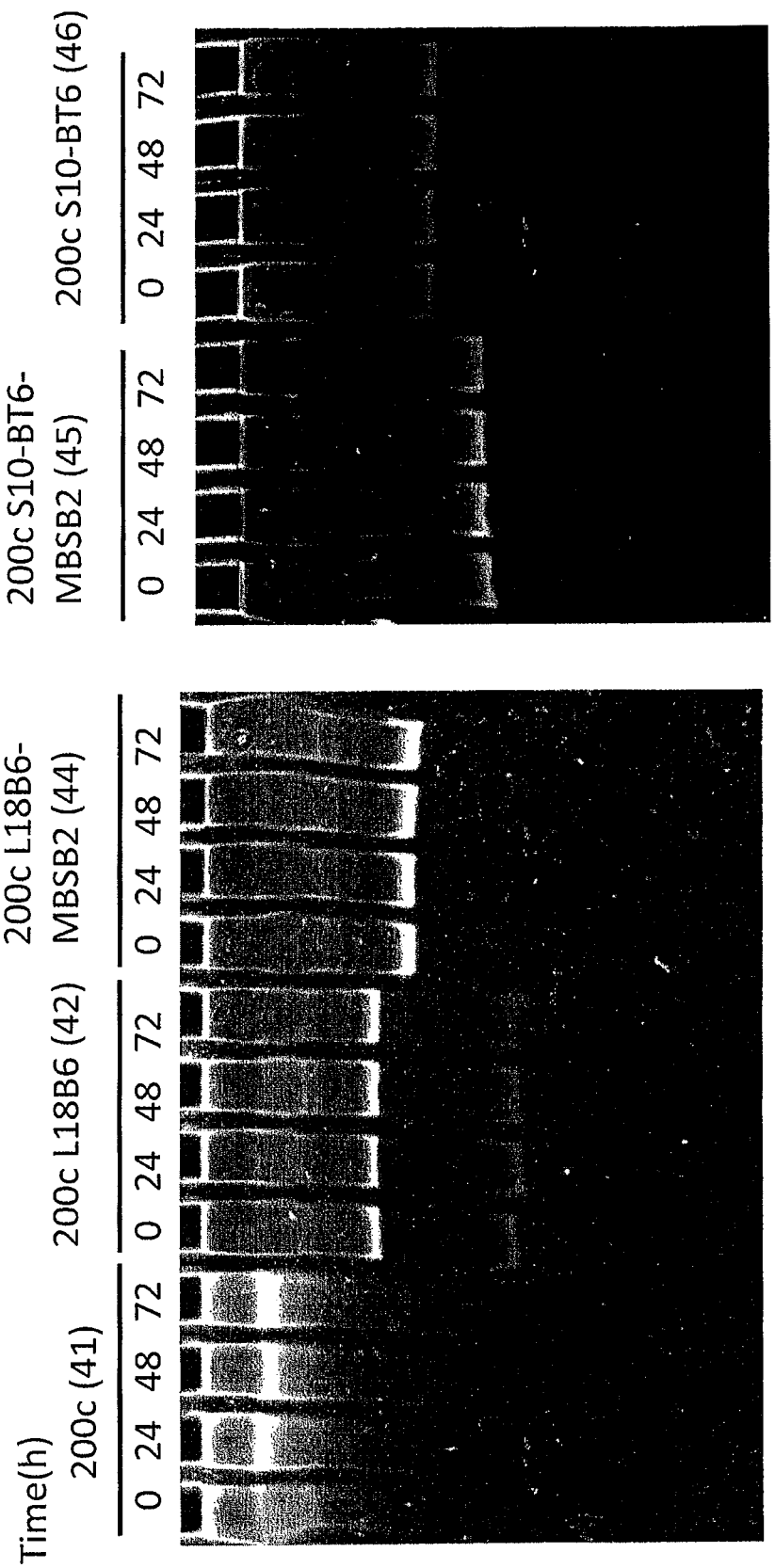

FIG. 20 shows electropherograms after mouse serum treatment. 0h, 24h, 48h, and 72h indicate the time treated with 37° C. mouse serum. The figure shows, from the left, (41) S-TuD-200c-1_22-pf, (42) S-TuD-200c-1_22-pf-L18B6, (44) S-TuD-200c-1_22-pf-L18B6-MBSB2, (45) S-TuD-200c-1_22-pf-S10-BT6-MBSB2, and (46) S-TuD-200c-1_22-pf-S10-BT6. Each of the numbers indicates time.

Figures 1, 21:
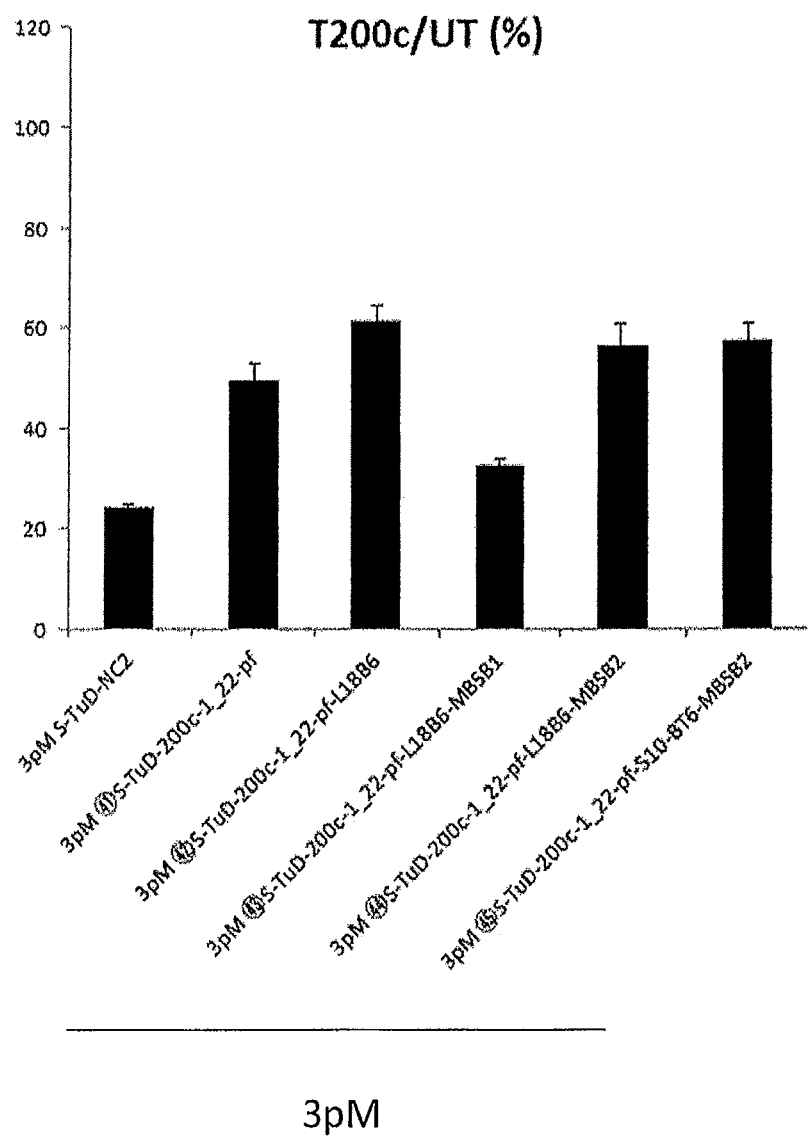
Figures 2, 21:
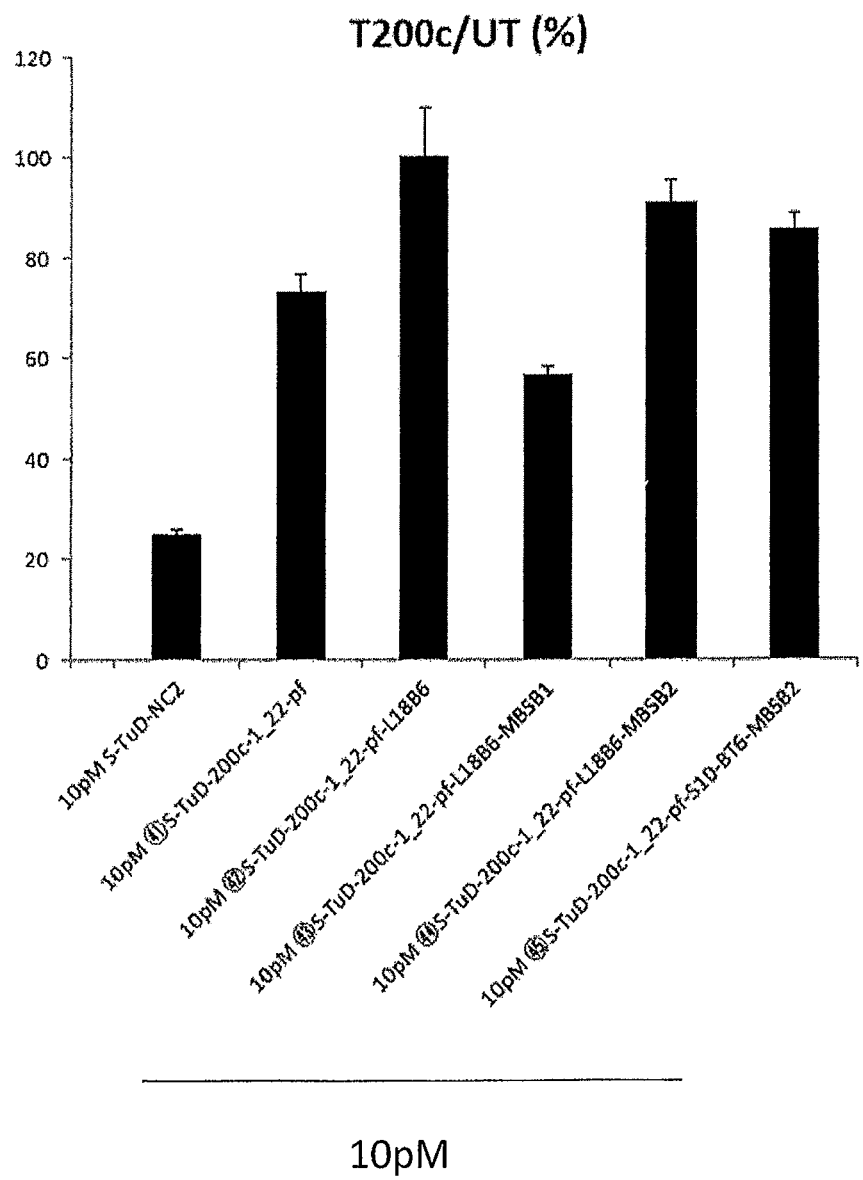

FIGS. 21-1 and 21-2 show results of a reporter assay, which is similar to that for miR199a-3p, with miR-200c. FIG. 21-1 shows results at 3 pM. The bars indicate the ratio of control reporter activity to miR-199a-3p reporter inhibitory activity. The bar is higher for a higher inhibitory effect of S-TuD.

FIGS. 21-1 and 21-2 show results of a reporter assay, which is similar that for miR199a-3p, with miR-200c. FIG. 21-2 shows results at 10 pM. The bars indicate the ratio of control reporter activity to miR-199a-3p reporter inhibitory activity. The bar is higher for a higher inhibitory effect of S-TuD.

FIG. 22 is a result showing concentration dependency in a similar reporter assay with miR-200c. Rhombuses indicate S-TuD NC2, squares indicate the original, and triangles indicate (45). When short type (Stem 1=10, Stem 2=10) stems are converted to BNA$^{NC}$(NMe) and the complementary sequence of the non-seed region of the MBS thereof is further modified by BNA$^{NC}$(NMe) (45), the effect was nearly about 2-fold higher than the original (41) without any BNA$^{NC}$(NMe) modification. In view of the possibility of S-TuDs adsorbing non-specifically to a tube with a dosage of 0.1 to 10 pM, analysis was also performed with 30 pM of S-TuD NC2 added as a carrier, but an effect of the addition was not observed.

FIG. 23 shows structures of S-TuD targeting miR-21 which were used in a universality confirmation experiment. The figure shows, from the top, each of (51) S-TuD-21-1_17-10mut, (52) S-TuD-21-1_17-10mut-L18B6, (53) S-TuD-21-1_17-10mut-L18B6-MBSB1, (54) S-TuD-21-1_17-10mut-S10-BT6, and (55) S-TuD-21-1_17-10mut-S10-BT6-MBSB1.

Figure 24:
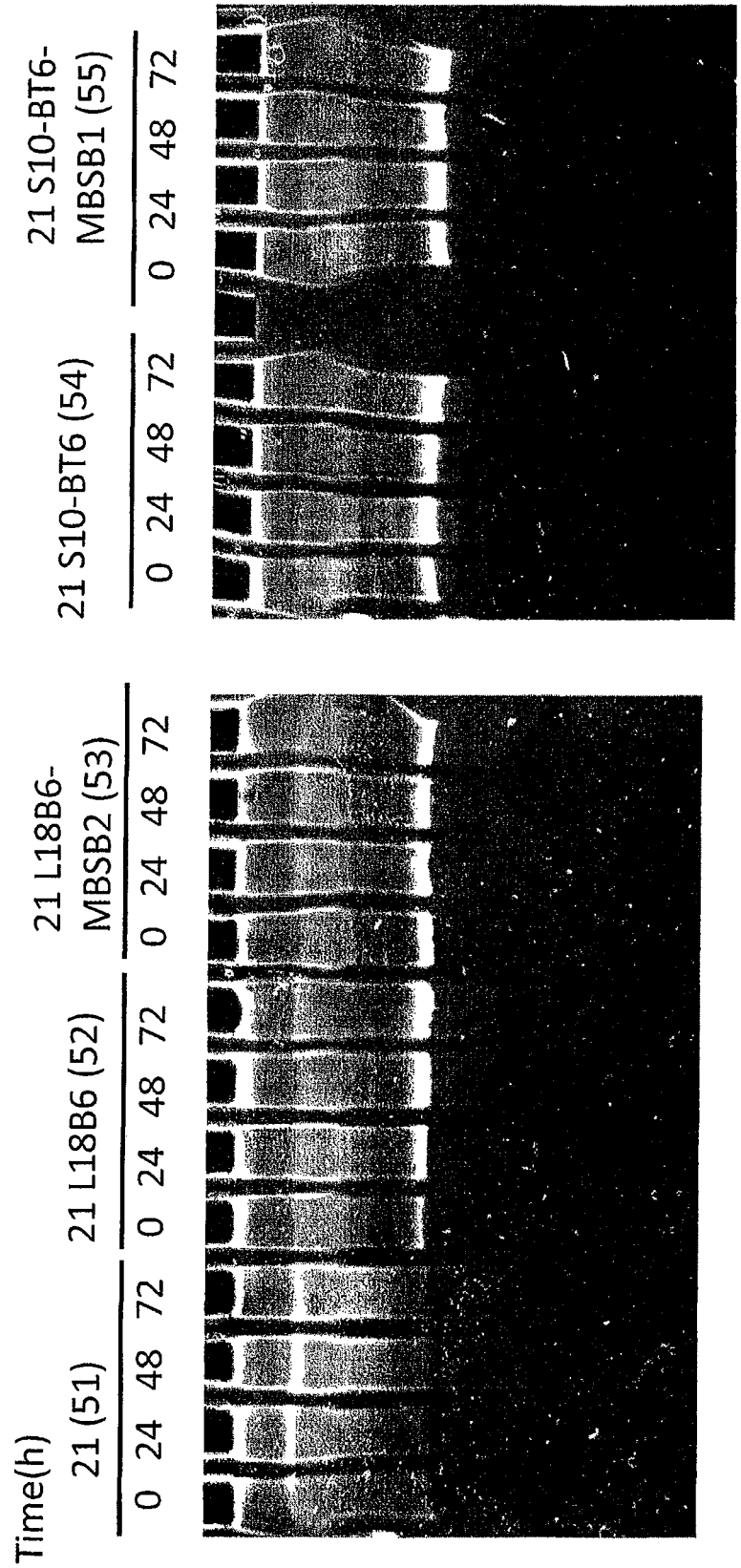

FIG. 24 shows electropherograms after mouse serum treatment. 0h, 24h, 48h, and 72h indicate the time treated with 37° C. mouse serum. The figure shows, from the left, (51) S-TuD-21-1_17-10mut, (52) S-TuD-21-1_17-10mut-L18B6, (53) S-TuD-21-1_17-10mut-L18B6-MBSB1, (54) S-TuD-21-1_17-10mut-S10-BT6, and (55) S-TuD-21-1_17-10mut-S10-BT6-MBSB1. Each of the numbers indicates time.

Figures 1, 25:
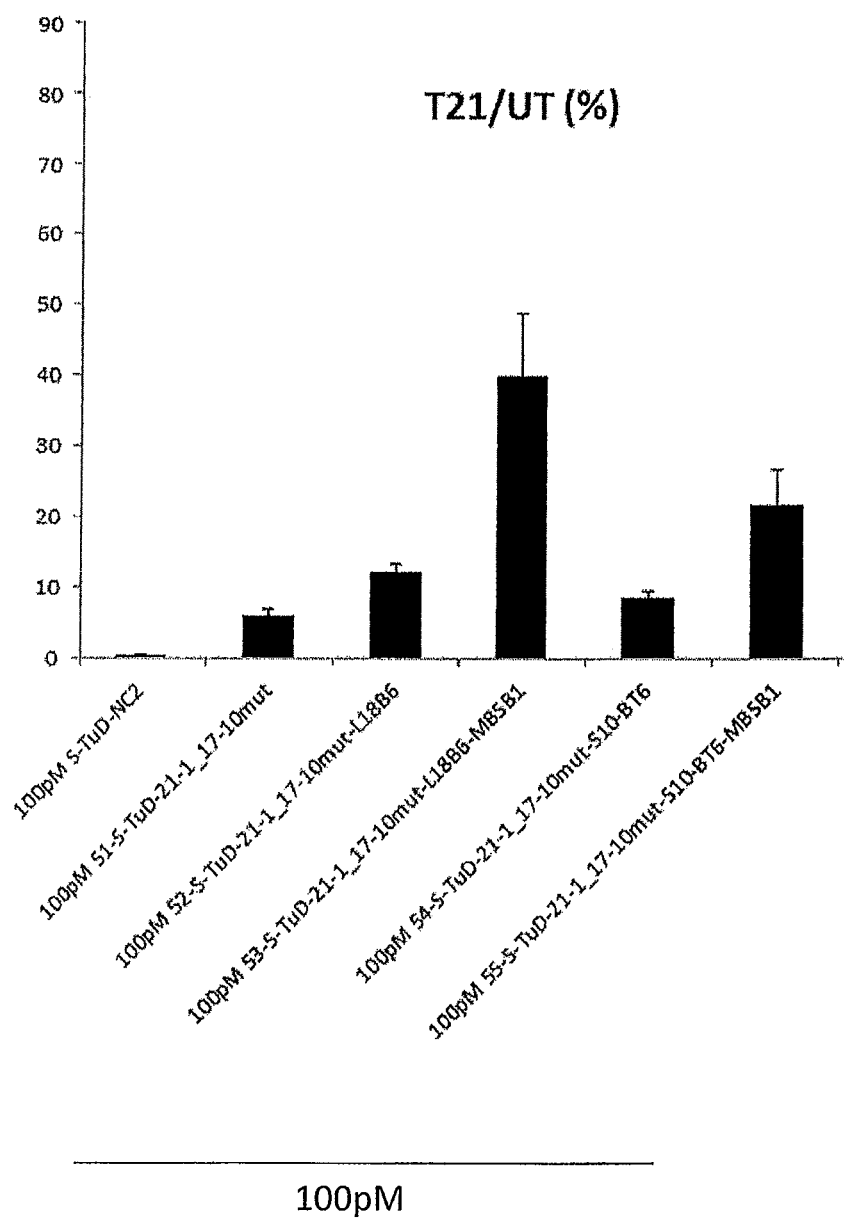
Figures 2, 25:
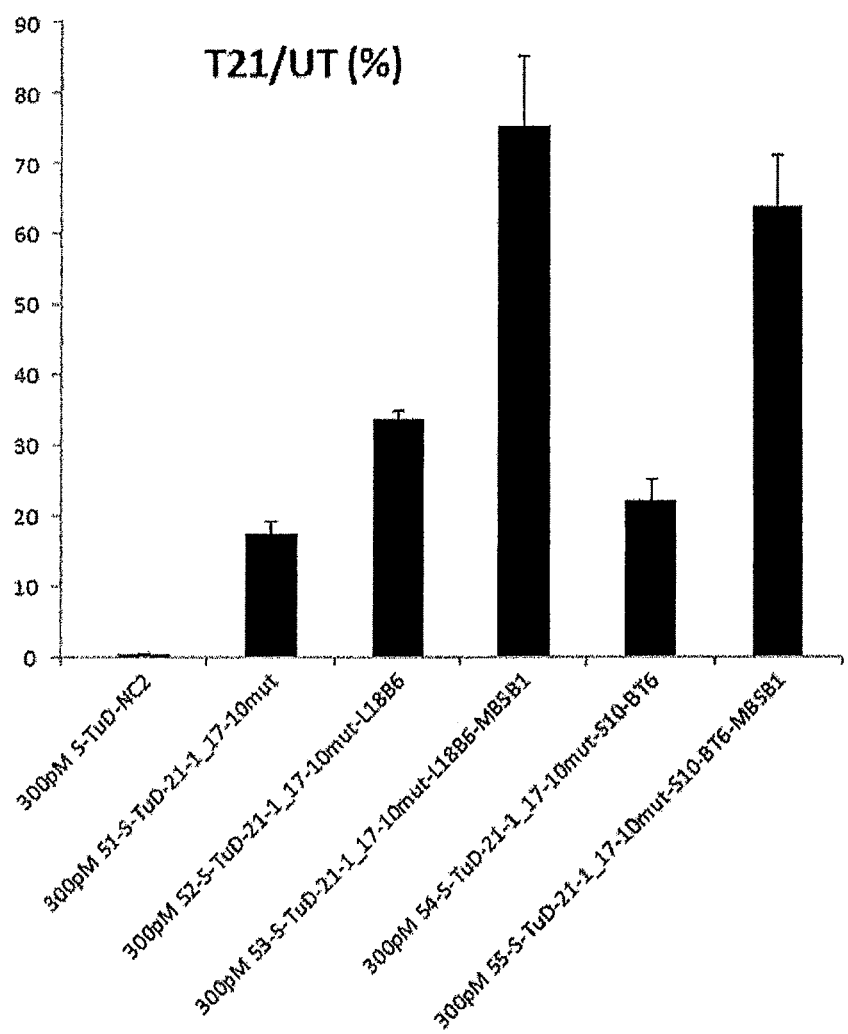

FIGS. 25-1 and 25-2 show results of a similar reporter assay for miR-21. FIG. 25-1 shows results at 100 pM. The bars indicate the ratio of control reporter activity to miR-199a-3p reporter inhibitory activity. The bar is higher for a higher inhibitory effect of S-TuD.

FIGS. 25-1 and 25-2 show results of a similar reporter assay for miR-21. FIG. 25-2 shows results at 300 pM. The bars indicate the ratio of control reporter activity and miR-199a-3p reporter inhibitory activity. The bar is higher for a higher inhibitory effect of S-TuD.

Figure 26:
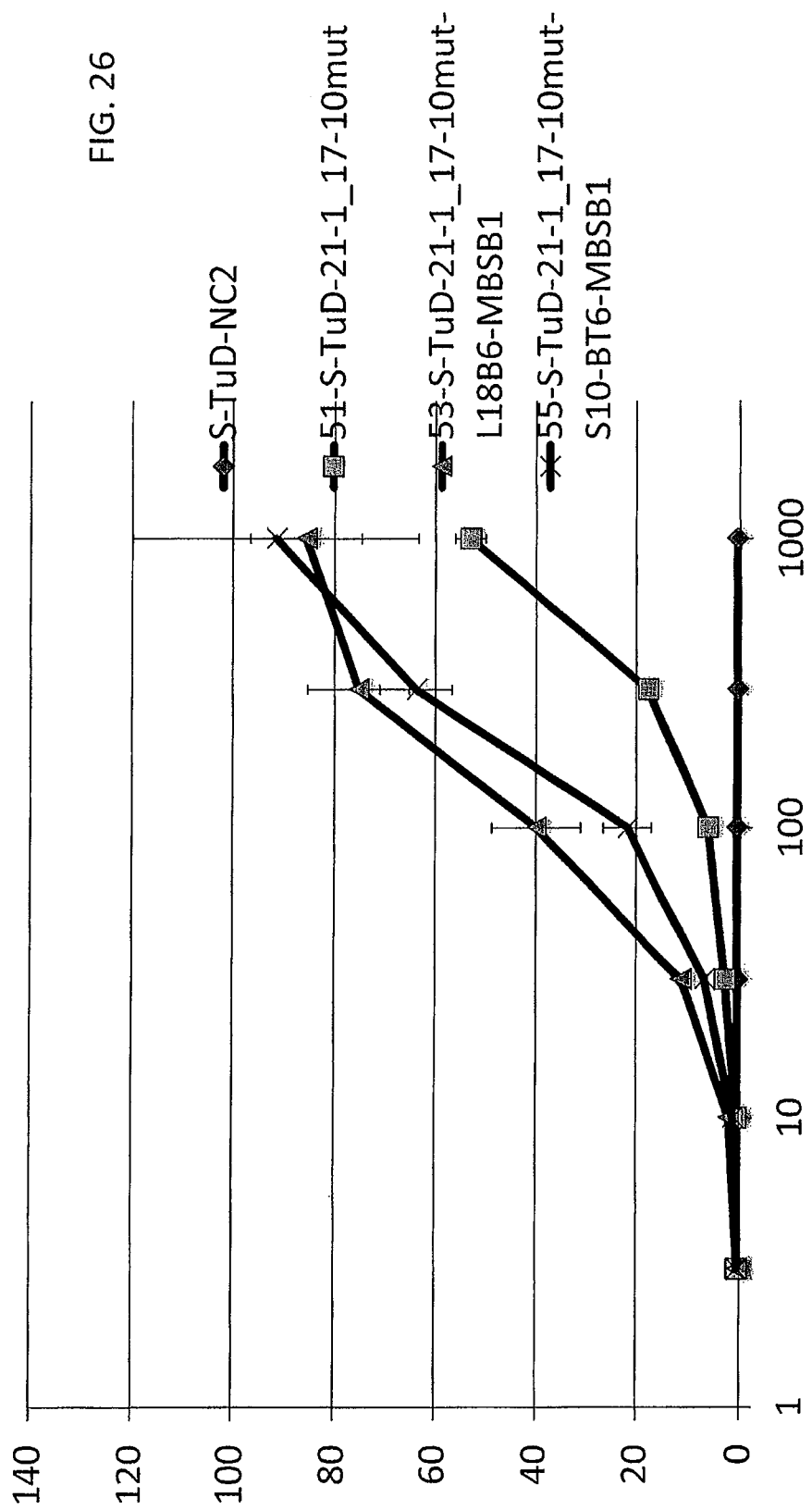

FIG. 26 is a result showing the concentration dependency of a similar reporter assay with miR-21. Compared to the original No. 51 (squares), the effect of No. 53 (triangles), which has the stem and MBS portions modified by $BNA^{NC}$ (NMe), increased nearly 10-fold. For the short types, the effect of No. 55 (x), which has the MBS portion modified, increased 3-fold or more compared to No. 51, but was about ⅔-fold compared to long type No. 53. Rhombuses indicate control.

FIG. 27 shows the structures of S-TuDs which were used in an in vivo experiment. The figure shows, from the top, (51) S-TuD-21-1_17-10mut, (53) S-TuD-21-1_17-10mut-L18B6-MBSB1, and (55) S-TuD-21-1_17-10mut-S10-BT6-MBSB1.

FIG. 28 shows results of measuring the amount of miR-21 in the kidney by RT-PCR. Each S-TuD was administered to the orbital vein of mice at 1 mg/kg (n=3). After 24 hours, kidneys were collected to quantify the amount of miR-21 (free miR-21 which is not considered to be bound to S-TuD) by RT-PCR. From the left, the results using PBS and a modified S-TuD of 51, 53, and 55, are shown.

Figure 29:
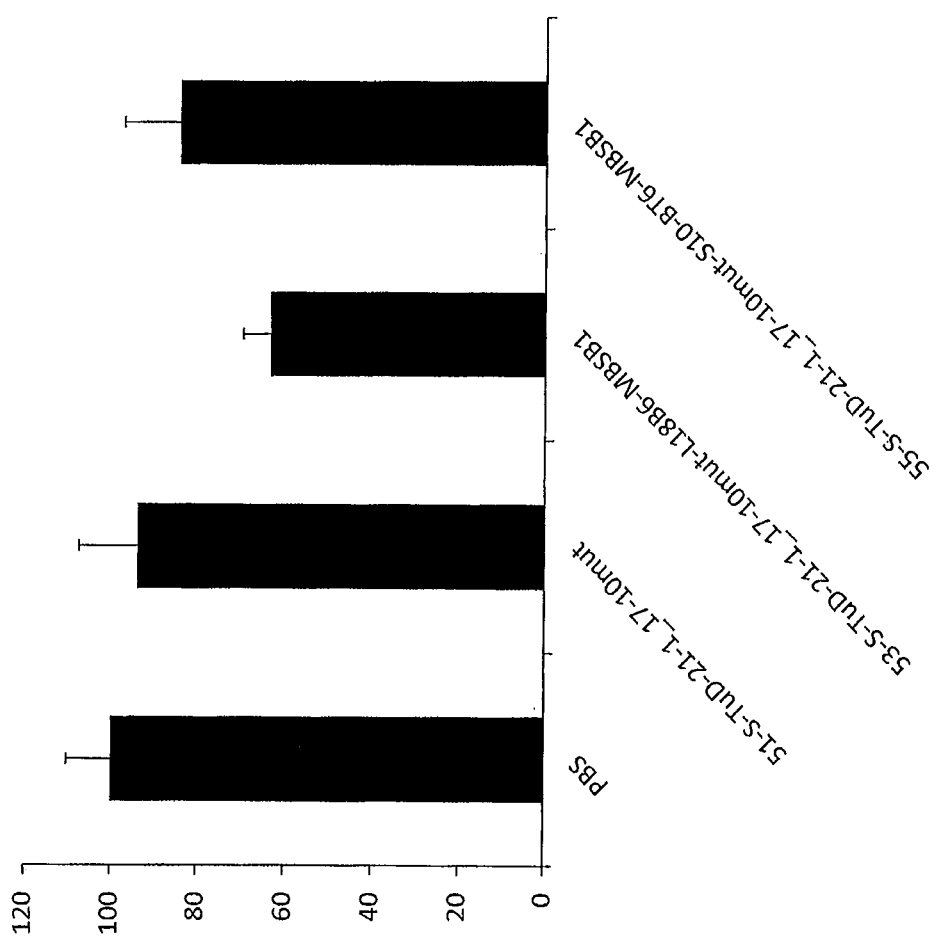

FIG. 29 shows the mean values of miR-21 in the kidneys of three mice. 53 has the least amount of miR-21, followed by 55. A decrease in miR-21 was hardly observed for the original S-TuD, but a decrease is detected in 53 and, to a lesser extent, 55.

Figure 30:
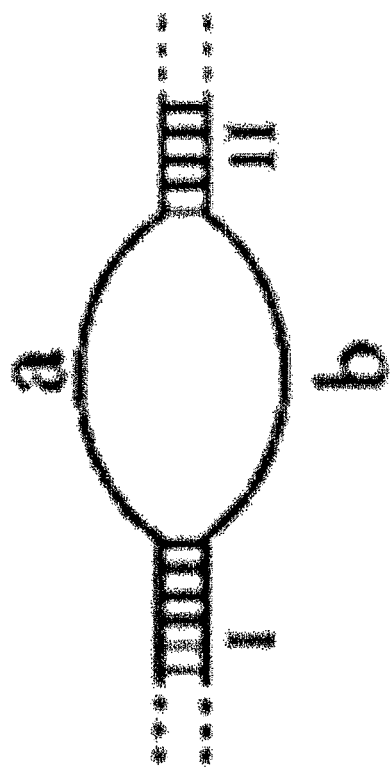

FIG. 30 shows a typical structure of the miRNA inhibiting complex of the present invention. This figure shows a form in which two RNA strands comprising an MBS are each bound to one of two double-stranded structures, so that the strands are sandwiched by the two double-stranded structures.

Figure 31:
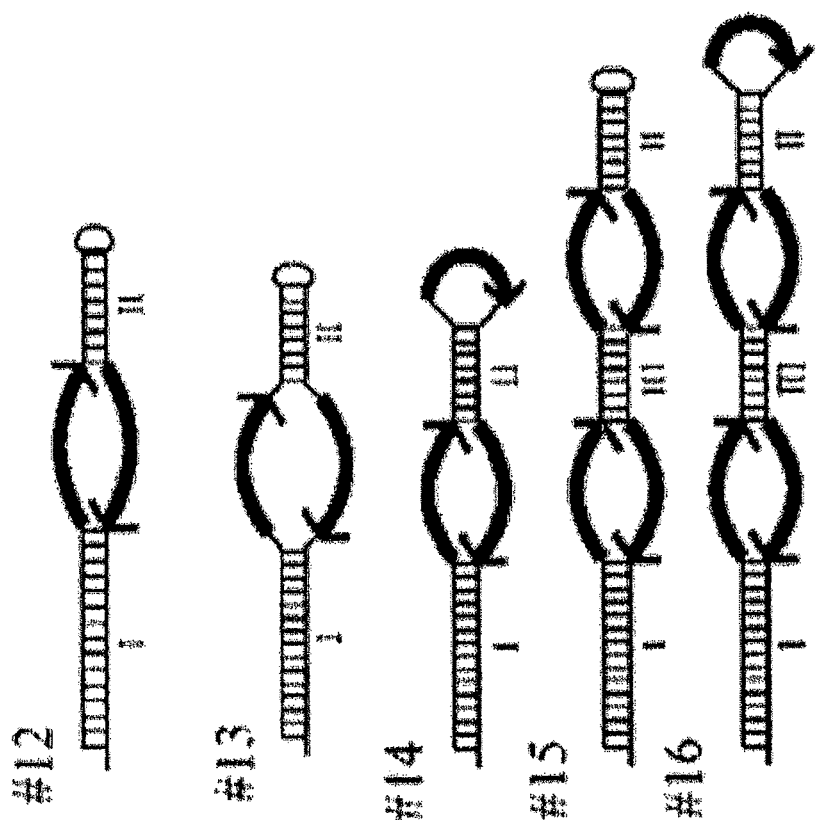

FIG. 31 also shows typical structures of the miRNA inhibiting complexes of the present invention. The figure shows #12 to #16 as typical examples. In this figure, two RNA strands comprising an MBS are bound to the paired respective strands of a double-stranded structure. Thus, the directions of RNA strands are opposite to each other.

FIG. 32 shows examples of sequences that were used in Example 7. The indicated sequences used, from the top row, the original, (5) S-Tud199a-3p-1_18-pf-U4BNA SI-8; (1)' S-TuD199a-3p-1_18-pf-S10; (2)' S-TuD199a-3p-1_18-pf-S10-BT8; (6)' S-TuD199a-3p-1_18-pf-S10-BT6; (7)' S-TuD199a-3p-1_18-pf-S10-LT6; and (8)' S-TuD199a-3p-1_18-pf-S10-BT12.

Figures 1, 33:
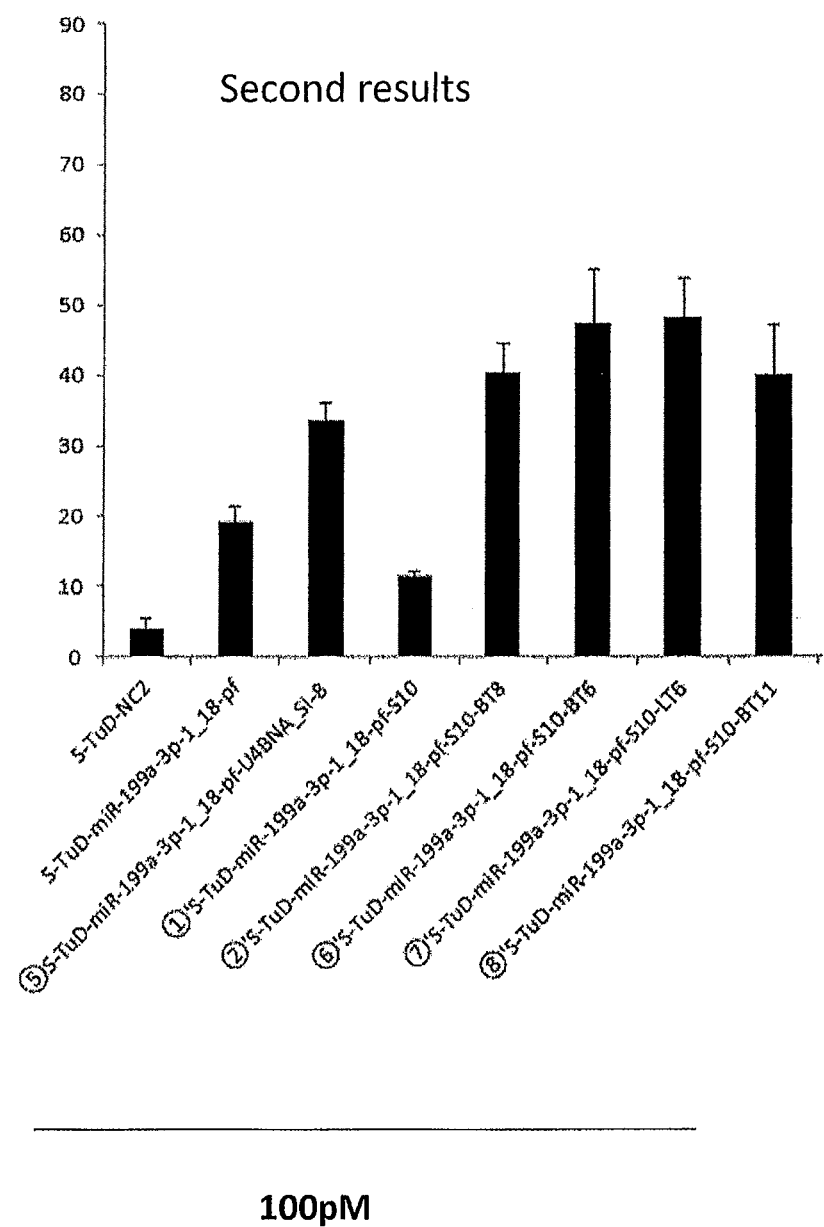
Figures 2, 33:
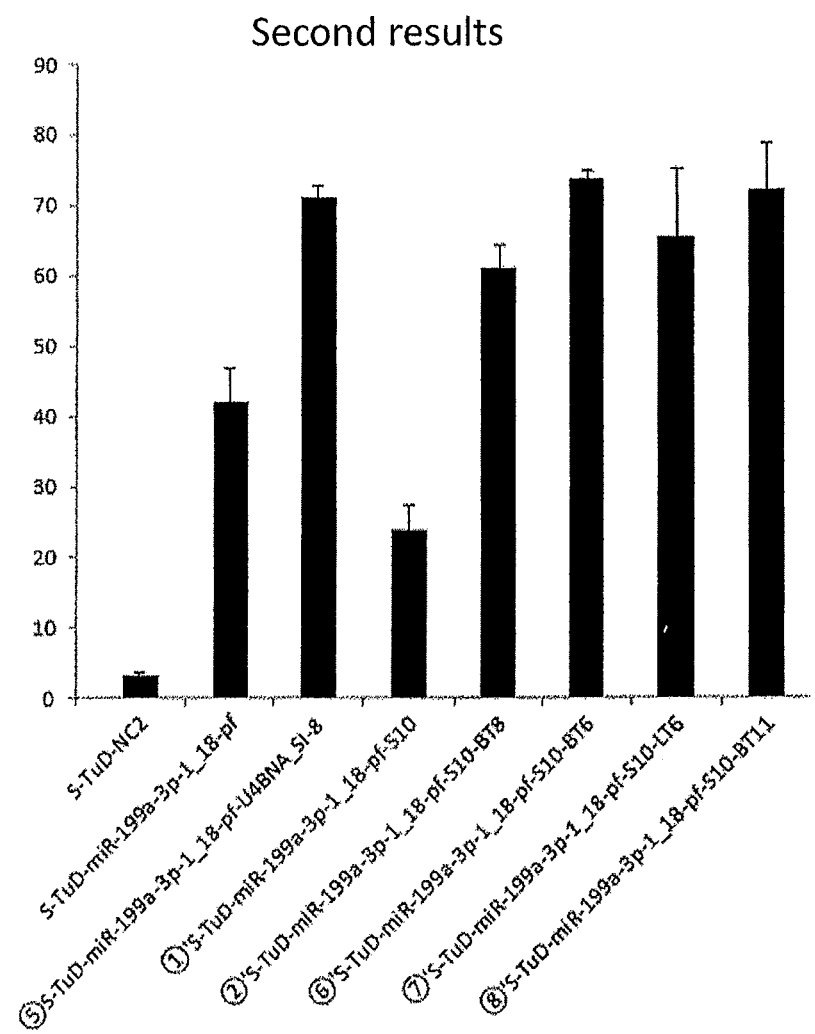

FIGS. 33-1 and 33-2 show the assay results of Example 7. FIG. 33-1 shows the results of the eight samples at 100 pM. The left end of each figure is a control, and the 2nd to 8th bars from the left show results for each sample.

FIGS. 33-1 and 33-2 show the assay results of Example 7. FIG. 33-2 shows the results of the eight samples at 300 pM. The left end of each figure is a control, and the 2nd to 8th bars from the left show results for each sample.

FIG. 34 shows examples of sequences that were used in Example 8. The figure shows, from the top row, the original, (6)' S-TuD199a-3p-1_18-pf-S10-BT6; (1)" S-TuD199a-3p-1_18-pf-S10-BT4; (2)" S-TuD199a-3p-1_18-pf-S8-BT6; (3)" S-TuD199a-3p-1_18-pf-S8-BT4; (4)" S-TuD199a-3p-1_18-pf-S6-BT6; and (5)" S-TuD199a-3p-1_18-pf-S6-BT4.

Figures 1, 35:
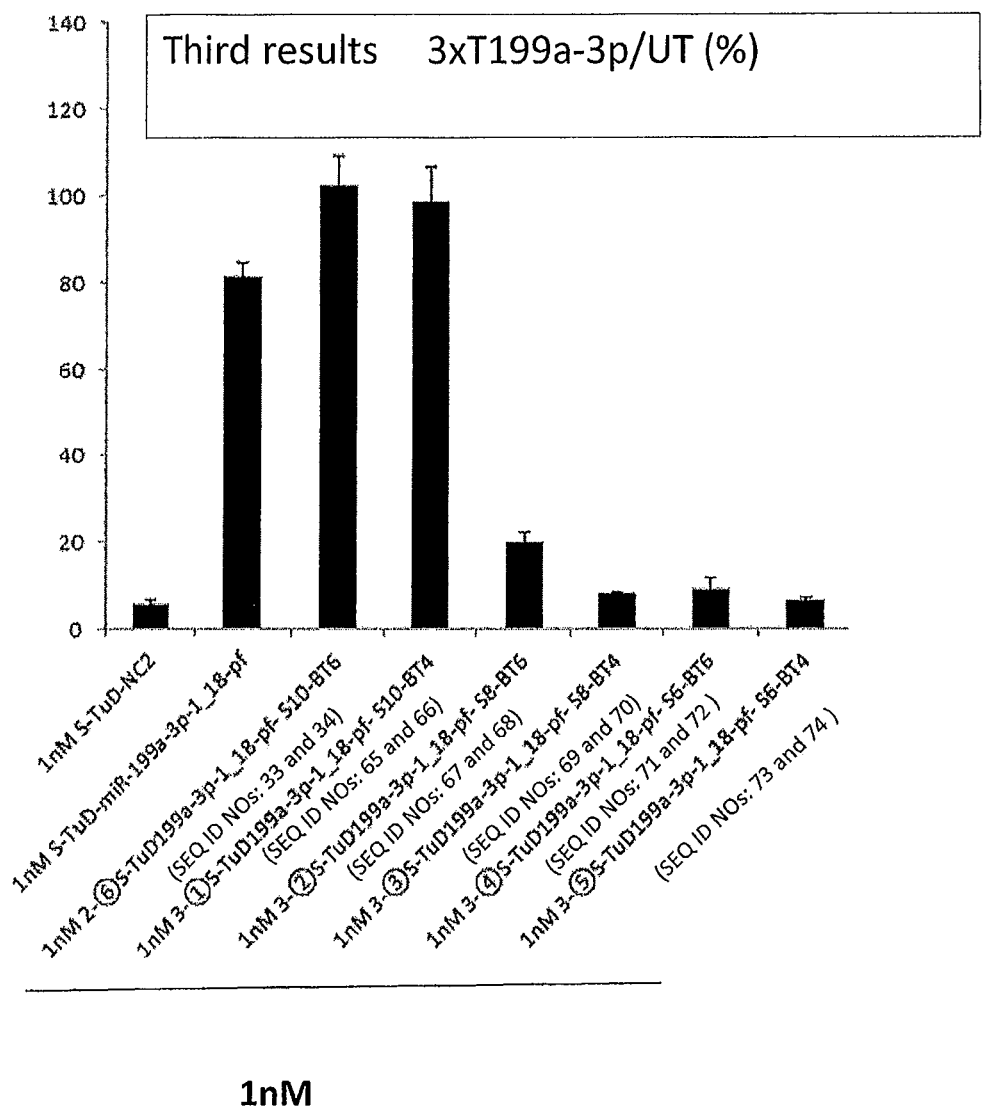
Figures 2, 35:
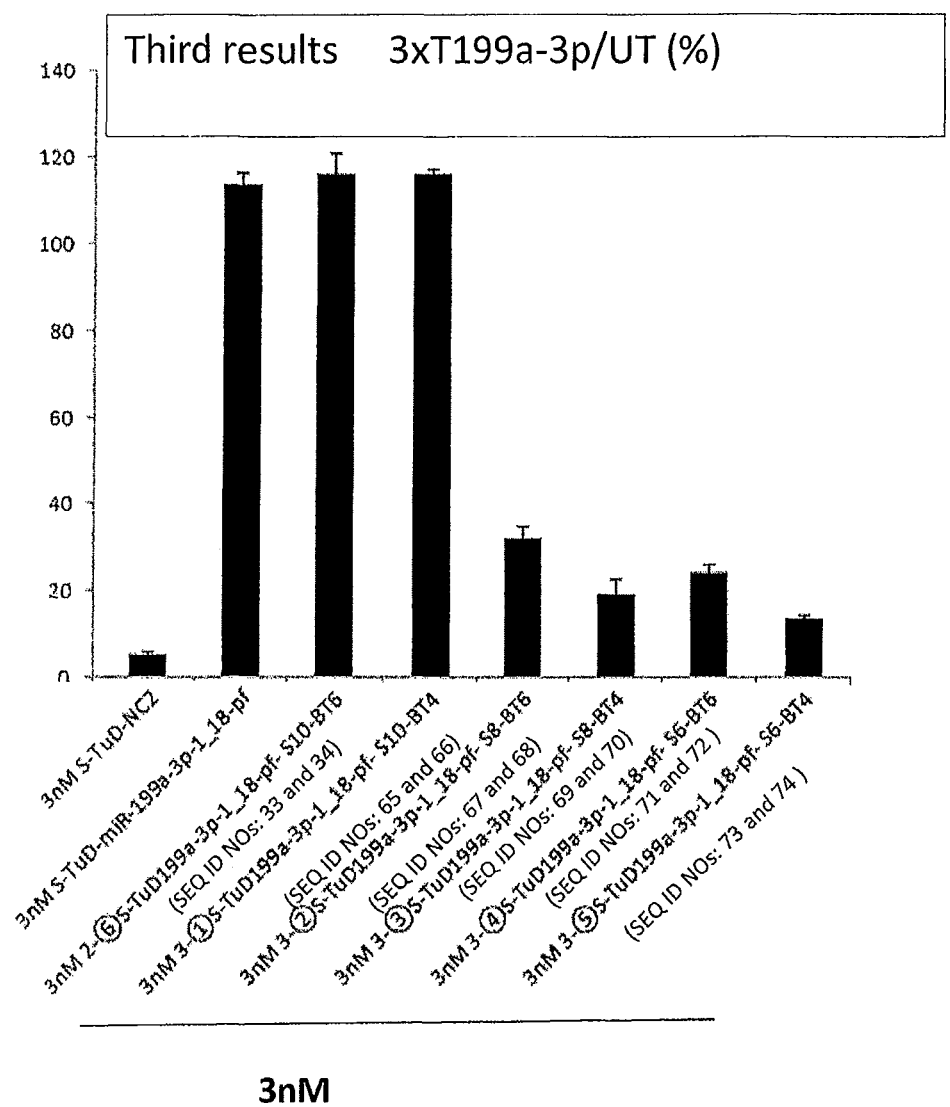

FIGS. 35-1 and 35-2 show the assay results of Example 8. FIG. 35-1 shows the results of the eight samples at 1 nM. The left end of each figure is a control, and the 2nd to 8th bars from the left show results for each sample.

FIGS. 35-1 and 35-2 show the assay results of Example 8. FIG. 35-2 shows the results of the eight samples at 3 nM. The left end of each figure is a control, and the 2nd to 8th bars from the left show results for each sample.

FIG. 36 shows examples of sequences that were used in Example 9. The figure shows, from the top row, the original, (4) S-TUD-miR-199a-1_18-pf U4BNA-ds; (1)' S-TuD199a-3p-1_18-pf-S10; (2)' S-TuD199a-3p-1_18-pf-S10-BT8; (6)' S-TuD199a-3p-1_18-pf-S10-BT6; and (1)" S-TuD199a-3p-1_18-pf-S10-BT4.

Figures 1, 37:
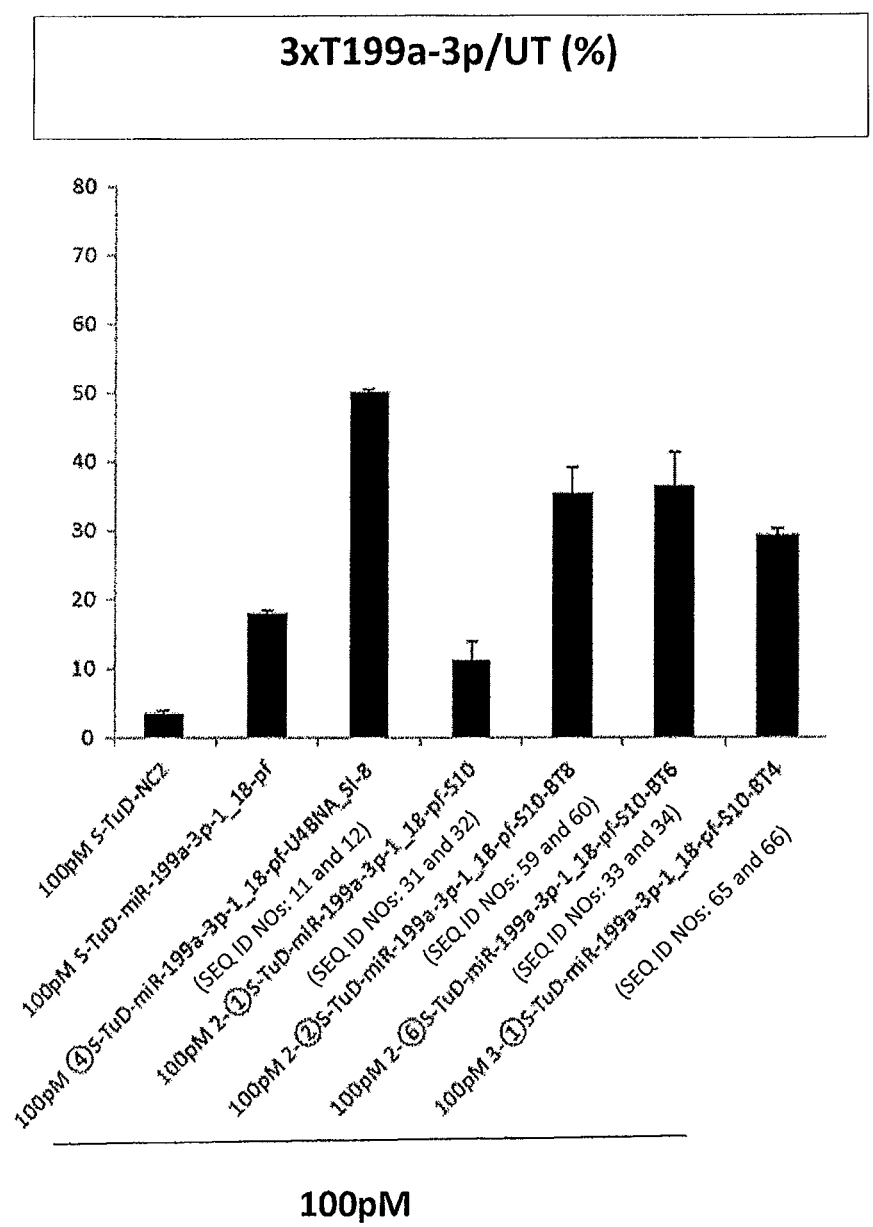
Figures 2, 37:
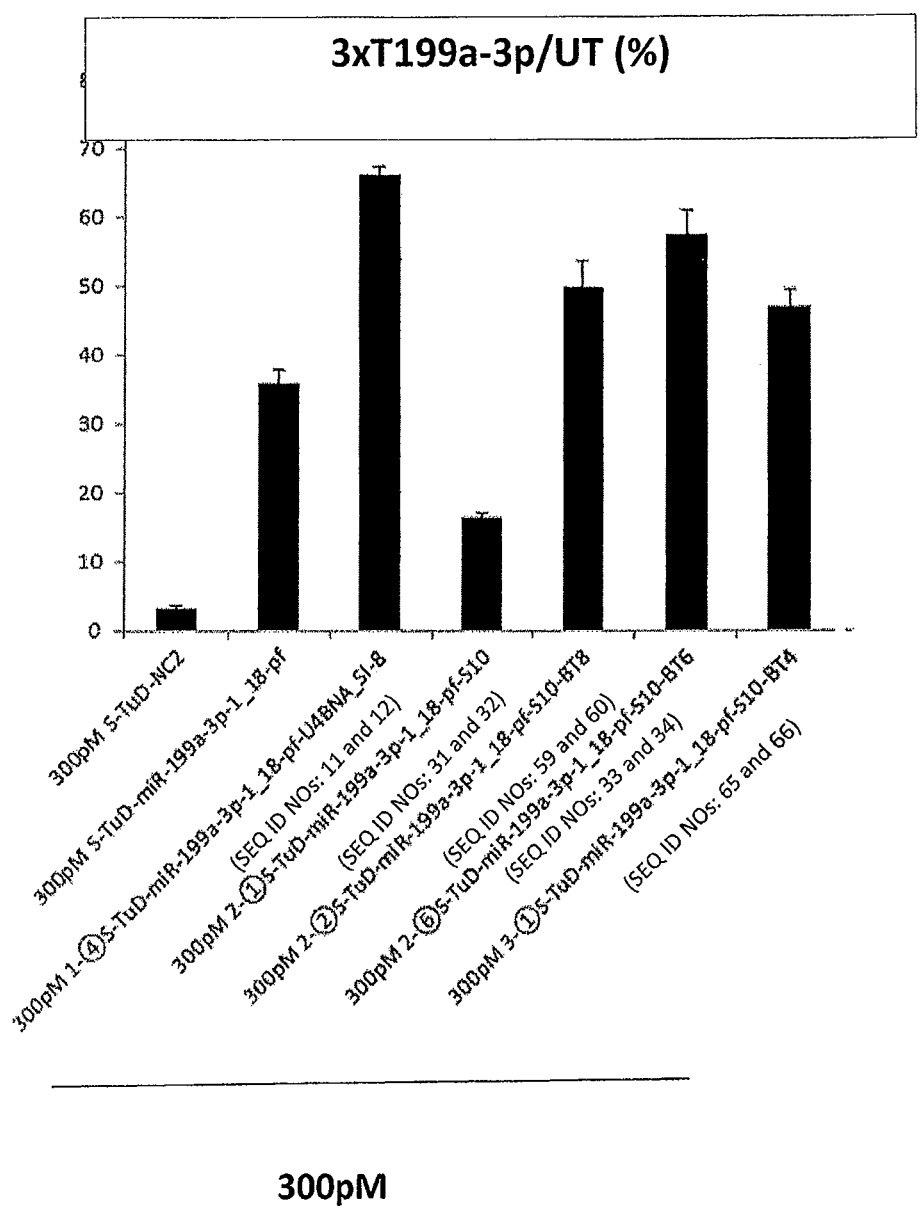

FIGS. 37-1 and 37-2 show the assay results of Example 9. FIG. 37-1 shows the results of the eight samples at 100 pM. The left end of each figure is a control, and the 2nd to 8th bars from the left show results for each sample.

FIGS. 37-1 and 37-2 show the assay results of Example 9. FIG. 37-2 shows the results of the eight samples at 300 pM. The left end of each figure is a control, and the 2nd to 8th bars from the left show results for each sample.

FIG. 38 shows results of evaluation of physical properties (HPLC purity analysis) of S-TuD wherein some of the bases of the STEM region were changed to a type of nucleotide species ($BNA^{NC}$(NMe)) that elevates the double-strand formation capability. The top row is for the original, and the bottom row shows results using (1)' of the present invention.

Figure 39:
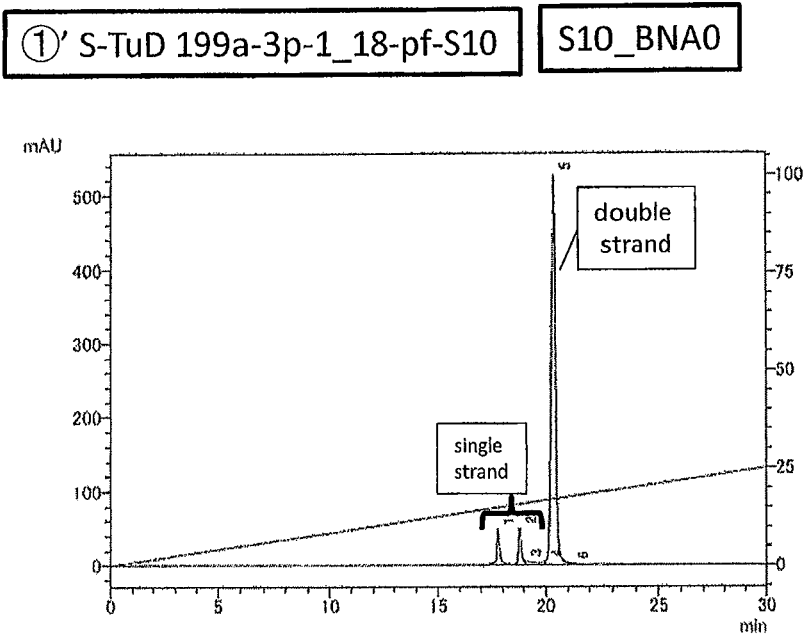
Figure 1:
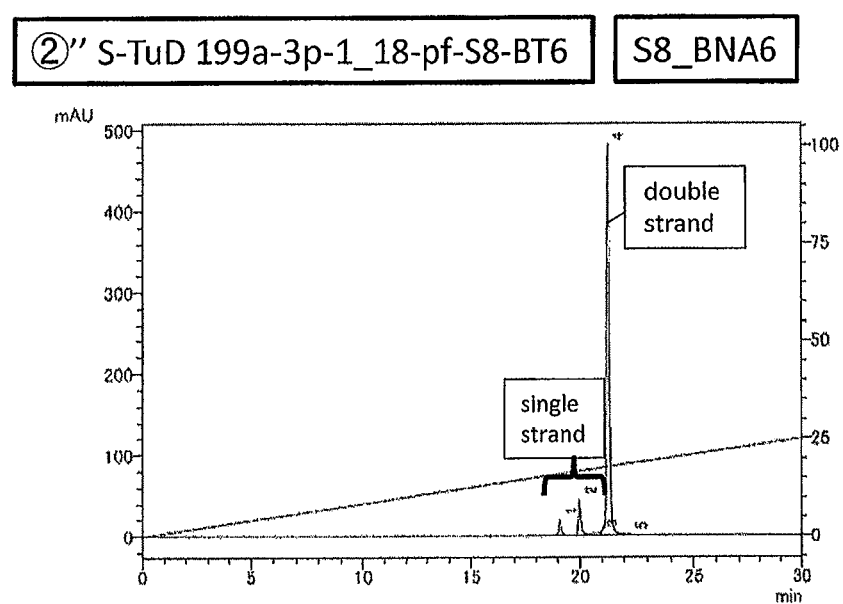
Figure 39:
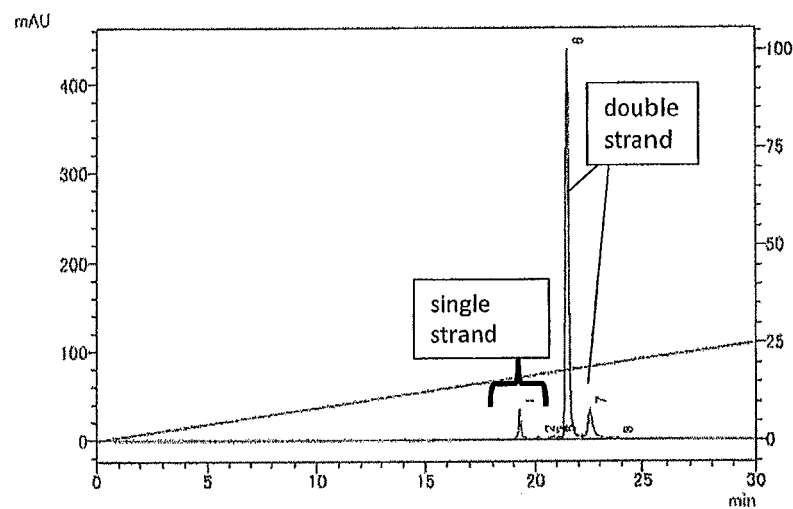
Figure 2:
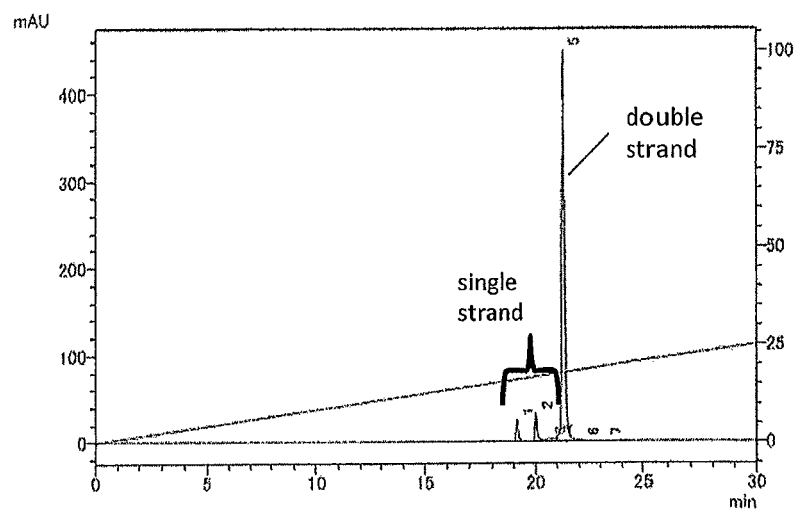

FIGS. 39-1 and 39-2 show that shortening the STEM I region to 10 bp results in a similar double-strand formation capability to the original S-TuD which is 2'-0-methyl only form.

FIGS. 39-1 and 39-2 show that shortening the STEM I region to 10 bp results in a similar double-strand formation capability to the original S-TuD which is 2'-0-methyl only form.

FIG. 40 is a continuation of FIGS. 39-1 and 39-2, which shows, from the top, results for each of (4)" and (5)".

DESCRIPTION OF EMBODIMENTS

The present invention is explained hereinafter. Throughout the entire specification, a singular expression should be understood as encompassing the concept thereof in plural form, unless specifically noted otherwise. Thus, singular articles (e.g., "a", "an", "the", and the like in the case of English) should also be understood as encompassing the concept thereof in plural form, unless specifically noted otherwise. Further, the terms used herein should be understood to be used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

(miRNA Inhibiting Complex)

The present invention relates to an improved form of miRNA inhibiting complexes that are capable of efficiently and specifically inhibiting miRNAs. The miRNA inhibiting complex of the present invention is characterized by comprising at least one double-stranded structure and an miRNA binding sequence (MBS), wherein two strands of the miRNA binding sequence are bound to (generally each to one of) two strands on at least one end of the double-stranded structure, and the miRNA inhibiting complex comprises at least one bridged nucleic acid (BNA). The inhibiting complex of the present invention may also be referred to as "S-TuD". It should be noted that the double-stranded structure may be called a "first" double-stranded structure, so that this can be distinguished from another double-stranded structure, which may be comprised in the complex of the present invention. The complex of the present invention may or may not be single stranded (i.e., one molecule bound by a covalent bond). For example, the complex of the present invention may be comprised of a single strand, double-strand, or more strands. For example, a complex consisting of a double-stranded RNA in which RNA strands comprising an MBS are each bound to one of two strands on one end of a double-stranded structure is encompassed by the present invention, as long as the complex comprises at least one bridged nucleic acid (BNA such as $BNA^{NC}$(NMe)). Further, a single RNA strand comprising at least one MBS may be bound to two strands on one end of a double-stranded structure. In this case, two strands on one end of a double-stranded structure would be linked. An RNA linking two strands of a double-stranded structure comprises at least one MBS, but may comprise, for example, two, three or more MBSes. A double-stranded structure comprises a stem loop or a hairpin. In other words, a double-stranded structure may be a double-stranded structure comprised in a stem loop or a hairpin.

In the present invention, a "seed region" refers to a region, which is about 2 to 8 bases from the 5' end and is required for activity of an miRNA, in an miRNA sequence. A "stem region" refers to a region of a double-stranded structure. "Original" refers to conventional "all 2'-OMe RNA types", i.e., types comprised of all 2'-OMe RNAs. Examples thereof include those described in Patent Literature 1 and the like.

The miRNA inhibiting complex in the present invention may be a structure with a double-stranded structure, comprising at least one RNA or an analog thereof. The complex preferably comprises one or two molecules comprising an RNA or an analog thereof.

In the present invention, an "miRNA binding sequence (MBS)" refers to a sequence binding to an miRNA. MSBes comprise at least a moiety that is complementary to an miRNA so that the MBS can bind to the miRNA. As shown in Patent Literature 1, an MBS may or may not be a fully complementary sequence to an miRNA. For example, an MBS may be a sequence of a naturally-occurring RNA targeted by an miRNA. For example, an MBS comprises at least 10, such as 11 bases or more, 12 bases or more, 13 bases or more, 14 bases or more, 15 bases or more, 16 bases or more, 17 bases or more, 18 bases or more, 19 bases or more, 20 bases or more, 21 bases or more, 22 bases or more, 23 bases or more, or 24 bases or more contiguous or non-contiguous complementary bases to an miRNA. Preferably, the complementary bases are contiguous, or have a gap at three positions or less, two positions or less, and preferably one position. The gaps may be unpaired (bulges) on the MBS side and/or the miRNA side. Gaps at one position may have a bulge nucleotide on only one of the strands, or unpaired nucleotides on both strands. Preferably, they are at least designed to include unpaired nucleotides on the MBS side. The number of bases in a single bulge or mismatch is, for example, six nucleotides or less, preferably five nucleotides or less, four nucleotides or less, three nucleotides or less, two nucleotides or less, or one nucleotide on a single strand for each bulge of mismatch at one position. In the present invention, an MBS that can form a bulge exhibited a higher miRNA inhibiting effect than an MBS consisting of a fully complementary sequence (Patent Literature 1). Thus, an MBS is preferably designed to form a bulge to attain higher miRNA inhibiting effects. For example, the following MBSes are not readily degraded so they can be expected to have a high level of activity: MBSes in which 10th and/or 11th base from the 3' end of the MBS are not complementary to an miRNA, or comprising extra bases between 10th and 11th bases (or MBSes in which 10th and/or 11th base from the 5' end of a target sequence in an miRNA (a sequence that hybridizes with an MBS) are not complementary to the MBS, or MBSes comprising unpaired bases between the 10th and 11th nucleotides). In such a case, an MBS may be designed so that, for example, bases including the 10th and 11th bases from the 5' end of an miRNA are unpaired. For example, an MBS may be designed so that 9th to 11th, 10th to 12th, or 9th to 12th bases are unpaired. Alternatively, an MBS may be designed so that there is no unpaired base on the miRNA side, but the MBS has unpaired base between 10th and 11th bases from the 3' end on the MBS side (or between sites corresponding to 10th and 11th bases from the 5' end of a target sequence (sequence that hybridizes with the MBS) in an miRNA. Unpaired bases may be present on the miRNA side and/or the MBS side, but are preferably at least on the MBS side. The number of unpaired nucleotides in each strand can be appropriately adjusted. For example, it is one to six nucleotides, preferably one to five nucleotides, or more preferably three to five nucleotides, such as three, four, or five nucleotides.

It is known that a match in 2nd to 7th or 3rd to 8th bases from the 5' end (called the "seed region") of an miRNA is important for target recognition by the miRNA (Jackson A L et al., RNA 12(7): 1179-1187, 2006; Lewis B P et al., Cell 120: 15-20, 2005; Brennecke et al. PLoS BIOLOGY 3, 0404-0418, 2005; Lewis et al. Cell 115, 787-798, 2003; Kiriakidou et al. Genes & Development 18, 1165-1178, 2004). In fact, it was demonstrated that the miRNA-inhibiting RNAs of the present invention having an MBS that matches only in the seed region and thus has low complementarity with other regions can effectively inhibit miRNAs (Patent Literature 1). In the present invention, an MBS is preferably fully complementary to an miRNA seed region (2nd to 7th and/or 3rd to 8th bases from the 5' end of an miRNA). In this case, a G:U pair (U:G pair) may be considered as complementary, but it is preferable to consider only G:C (C:G) and A:U (U:A) pairs as complementary. In the present invention, an MBS is preferably fully complementary to an miRNA seed region (2nd to 7th and/or 3rd to 8th bases from the 5' end of an miRNA), and comprises at least eight, more preferably nine, and more preferably ten contiguous bases that are complementary to the miRNA. Furthermore, an MBS of the present invention preferably comprises a total of 11 or more bases, more preferably 12 or more bases, and more preferably 13 or more bases that are complementary to an miRNA.

Preferably, an MBS is a sequence that hybridizes with an miRNA sequence under physiological conditions. Physiological conditions are, for example, 150 mM NaCl and 15 mM sodium citrate at pH 7.0 and 37° C. More preferably, an MBS is a sequence that hybridizes with an miRNA sequence under stringent conditions. Stringent conditions are, for example, conditions under 1×SSC ("1×SSC" means 150 mM NaCl and 15 mM sodium citrate at pH 7.0) or 0.5×SSC at 42° C., more preferably conditions under 1×SSC or 0.5×SSC at 45° C., and more preferably conditions under 1×SSC or 0.5×SSC at 50° C. In hybridization, for example, one of an miRNA sequence-comprising RNA and an MBS-comprising RNA is labeled, and the other is immobilized to a membrane to hybridize the two. Hybridization may be carried out under conditions such as in a solution containing 5×SSC, 7% (W/V) SDS, 100 µg/mL denatured salmon sperm DNA, and 5×Denhardt's solution (1×Denhardt's solution contains 0.2% polyvinyl pyrrolidone, 0.2% bovine serum albumin, and 0.2% Ficoll), at for example 37° C., 45° C., or 50° C. After incubation for a sufficient time (e.g., three, four, five, or six hours or more) and then washing under the above conditions, it is possible to detect whether the labeled nucleic acid is hybridized to determine whether a nucleic acid hybridizes under said conditions.

Alternatively, an MBS preferably exhibits high homology to the complementary sequence of an miRNA sequence. Examples of "high homology" include a nucleotide sequence with 70% or greater, 75% or greater, 76% or greater, 77% or greater, 78% or greater, 79% or greater, 80% or greater, 81% or greater, 82% or greater, 83% or greater, 84% or greater, 85% or greater, 86% or greater, 87% or greater, 88% or greater, 89% or greater, 90% or greater, 93% or greater, 95% or greater, 96% or greater, 97% or greater, 98% or greater, or 99% or greater identity. The base sequence identity can be determined using, for example, the BLAST program (Altschul, S. F. et al., J. Mol. Biol. 215: 403-410, 1990). This can be searched using default parameters, for example, on the BLAST web page of the NCBI (National Center for Biotechnology Information) (Altschul S. F. et al., Nature Genet. 3:266-272, 1993; Madden, T. L. et al., Meth. Enzymol. 266:131-141, 1996; Altschul S. F. et al., Nucleic Acids Res. 25:3389-3402, 1997; Zhang J. & Madden T. L., Genome Res. 7:649-656, 1997). For example, the sequence identity can be determined by creating an alignment of two sequences with the blast 2 sequences program (Tatiana A et al., FEMS Microbiol. Lett. 174:247-250, 1999) which compares two sequences. Gaps outside of an miRNA base sequence are ignored, and inner gaps are treated, for example, in the same manner as mismatches to calculate the value of identity to the entire miRNA base sequence (total base length determined by adding the gaps inside the sequence) in alignment. However, as shown in Patent Literature 1, a mismatch between an MBS and an miRNA can elevate the miRNA inhibiting activity. Thus, it is preferable, for example, to calculate the identity by ignoring gaps inserted into an miRNA sequence inside alignment.

Alternatively, an MBS preferably consists of a sequence with one or several base insertions, substitutions, and/or deletions with respect to a sequence complementary to an miRNA sequence. Preferably, an MBS consists of a sequence that has eight or less, seven or less, six or less, five or less, four or less, three or less, two or less, or one base insertion, substitution, and/or deletion with respect to a sequence complementary to an miRNA sequence. More preferably, an MBS consists of a sequence that has eight or less, seven or less, six or less, five or less, four or less, three or less, two or less, or one base insertion with respect to a sequence complementary to an miRNA sequence. The present invention demonstrates that an MBS with a mismatch has higher miRNA inhibiting activity than an MBS with a sequence that is fully complementary to an miRNA sequence. It is understood that this is because an MBS that is fully complementary to an miRNA may be cleaved by an RISC comprising an miRNA, thus decreasing the expression level of the miRNA inhibiting RNA. In particular, high activity can be expected from an MBS designed to have the 10th and/or 11th base from the 3' end of the MBS unpaired (or 10th and/or 11th base from the 5' end of a target sequence in an miRNA that hybridizes with an MBS is unpaired when hybridized with the MBS), or to comprise unpaired bases between the 10th and 11th bases, when the MBS is hybridized with the miRNA. Such unpairing may be, for example, a bulge on the MBS side. The number of bases forming a bulge is one to six bases, preferably one to five bases, and more preferably three to five bases (e.g., three, four, or five nucleotides). An MBS may consist of an RNA, comprise a nucleic acid analog, or consist of a nucleic acid analog. In particular, the miRNA inhibiting effect is expected to be elevated by converting a site cleaved in an MBS (10th and/or 11th base from the 3' end of the MBS, etc.) into a nucleic acid analog in order to prevent cleavage. It is also favorable to use nucleic acids that have a sugar or a backbone such as phosphorothioate or 2"-O-methyl (Krutzfeldt, J. et al., Nucleic Acids Res. 35: 2885-2892; Davis, S. et al., 2006, Nucleic Acids Res. 34: 2294-2304).

There are no particular limitations on miRNAs targeted by the miRNA inhibiting complexes of the present invention. miRNAs derived from any species such as plants, nematodes, and vertebrates may be targeted, as long as they have an miRNA structure. A very large number of miRNA sequences are known in various organisms, including humans, mice, chickens, zebrafish, and *Arabidopsis thaliana* (see the webpage of miR Base::Sequences: microrna.sanger-.ac.uk/sequences/). For example, miRNAs of mammals including mice, rats, goats, and the like, primates including monkeys, and humans can be targeted. Examples thereof include, but are not limited to, miR21 (Lagos-Quintana M et al., Science. 294:853-858, 2001; Mourelatos Z et al., Genes Dev. 16:720-728, 2002; Michael M Z et al., Mol Cancer Res. 1:882-891, 2003; Dostie J et al. RNA. 9:180-186, 2003), miR140 (Lagos-Quintana M et al., Curr Biol. 12:735-739, 2002; Cai X et al., Proc Natl Acad Sci USA. 102:5570-5575, 2005), miR1995 (Lagos-Quintana M et al., RNA. 9:175-179, 2003; Landgraf P et al., Cell. 129:1401-1414, 2007), miR16 (Lagos-Quintana M et al., Science. 294:853-858, 2001; Mourelatos Z et al., Genes Dev. 16:720-728, 2002; Lim L P et al., Science. 299:1540, 2003; Calin G A et al., Proc Natl Acad Sci USA. 99:15524-15529, 2002; Michael M Z et al., Mol Cancer Res. 1:882-891, 2003), miR497 (Bentwich I et al., Nat Genet. 37: 766-770, 2005; Landgraf P et al., Cell. 129:1401-1414, 2007), and the like.

In one embodiment, the miRNA inhibiting complex of the present invention relates to an miRNA inhibiting complex further comprising a second double stranded structure in addition to a first double-stranded structure, and a structure in which RNA strands comprising an MBS are each bound to one of two strands on one end of the first double-stranded structure, wherein the other ends of the RNA strands are each bound to one of two strands on one end of the second double-stranded structure so that the strands are sandwiched between the first double-stranded structure and the second double-stranded structure. The double-stranded structure may be a double-strand or a quadruple strand such as a G-quadruplex. For example, the present invention relates to an miRNA inhibiting complex further comprising a second double-stranded structure in addition to a first double-stranded structure, and a structure in which two strands on an end to which an MBS is bound in the first double-stranded structure are each bound to one of RNA strands comprising an MBS, wherein the other ends of the RNA strands are each bound to one of two strands of the second double-stranded structure so that the strands are sandwiched between the first double-stranded structure and the second double-stranded structure. For example, said RNA complex has a structure having at least two double-stranded structures, wherein four RNA strands constituting the two double-stranded structures are each bound to an RNA comprising an MBS without mediation of any of the remaining three strands. More simply stated, such an miRNA inhibiting complex is an miRNA-inhibiting complex in which two RNA strands comprising an MBS are each bound to one of strands of two double-stranded structures so that the strands are sandwiched between the two double-stranded structures (FIG. 30). In other words, the present invention encompasses an RNA, which is an RNA complex having the structure of FIG. 30, wherein the RNA strands a and b are sandwiched between double-stranded structures I and II, and one or more MBSs are comprised in each of said a and b. The two RNA strands comprising an MBS are bound to the respective paired strands in the double-stranded structures. Thus, the directions of the RNA strands are opposite to each other (FIG. 31, #12 to #16). By adding an MBS to each of the two strands in this manner, higher miRNA-inhibiting activity can be exerted.

Each of the two RNA strands comprising an MBS, which are sandwiched between two double-stranded structures, comprise one or more MBSes. Such MBSes may have the same or different sequences. Further, they may target the same miRNA, or they may be sequences that bind to different target miRNAs. For example, a single strand may comprise two or more, e.g., two, three, four, or five MBSes (FIG. 31, #12 to #16). For example, one or two MBSes may be comprised in each strand sandwiched between two double-stranded structures. For example, the miRNA inhibiting complex of the present invention may comprise two MBSes in total, and the two MBSes may have the same sequence or sequences that bind to the same miRNA.

Each of the paired strands in a double strand comprised in the miRNA inhibiting complex of the present invention is generally a separate RNA molecule as disclosed above, but one or both ends of the double strand may be bound to be straight or cyclic. "Straight" is a term that is used relative to "cyclic", meaning only that ends are present. Of course, this does not mean that a secondary structure is not formed. An miRNA inhibiting complex comprised of a straight single-stranded RNA can be produced, for example, by a single RNA synthesis. For example, when comprising two double-stranded structures, two strands on one end (the side to which an MBS is not bound) of a second double-stranded structure can be bound by a loop to form a single strand as a whole. A sequence linking a double strand may comprise one or more MBSes (e.g., FIG. 31; #13, #14, and #16). To make the sequence as compact as possible, the double strands can be linked by a short loop. For example, a double strand can be bound by a sequence of, for example, one to ten bases, preferably one to eight bases, two to six bases, three to five bases, such as four bases. Examples of the sequences include, but are not particularly limited to, 5'-GUCA-3'. For example, the present invention encompasses an RNA having the structure of FIG. 31 #13, in which RNA strands a and b are sandwiched between double-stranded structures I and II, wherein the double-stranded structure II forms a hairpin (or a stem loop), and each of said a and b comprises one or more MBSes.

The sequence of a double-stranded structure comprised in the miRNA inhibiting complex of the present invention is not particularly limited, thus can have any length of bases.

A preferred embodiment is disclosed in more detail below. The sequences of base pairs forming a double-stranded structure can be designed appropriately so that a double strand can be formed specifically and stably in an miRNA inhibiting complex. For example, it is preferable to avoid a homopolymeric sequence with a long repetition of the same base (e.g., eight or more bases, preferably seven or more bases, more preferably five or more bases, more preferably four or more bases, and more preferably three or more bases). It is also preferable to avoid sequences in which sequences of several bases are repeated in tandem, such as two-base repeat sequences or three to four base repeat sequences. The GC content of the double-stranded moiety can be adjusted appropriately, which is for example 12% to 85%, preferably 15% to 80%, 20% to 75%, 25% to 73%, 32% to 72%, 35% to 70%, 37% to 68%, or 40% to 65%. The sequences of stem I and stem II shown in Patent Literature 1 can be presented as examples, but the content is not limited thereto. An example of a quadruple strand includes a G-quadruplex, which can have the specific sequence of GGG-loop-GGG-loop-GGG-loop-GGG. In this regard, the sequence of loop can be selected appropriately. For example, all of the three loops may be a single base (e.g., M (A or C)), or three bases.

MBSes and double-stranded structures may be linked directly or via another sequence. For example, an MBS can be bound to an end of a double-stranded structure via a suitable linker or a spacer sequence. While significant inhibitory activity can be obtained by directly linking an MBS to a double-stranded moiety, an addition of a linker (also referred to as a spacer) further elevates the inhibitory effect on miRNAs (see Patent Literature 1). A linker or spacer sequence between an MBS sequence and a double-stranded structure may increase the accessibility of an MBS to an miRNA, which is present in RISC. The length of a linker or spacer may be adjusted appropriately. Examples thereof include one to ten bases, preferably one to nine bases, one to eight bases, one to seven bases, one to six bases, one to five bases, one to four bases, and one to three bases. For example, two or more MBSes are also preferably linked via a linker or spacer. There is no particular limitation on the sequence of a linker or spacer. For example, it can be a sequence consisting of A and/or C, or a sequence comprising more A and/or C than other bases. Further, it is preferable to not make the linker or spacer sequences to form stable base pairs between opposing linker or spacer sequences or MBSes. Examples thereof include AAC, CAA, ACC, CCA, and sequences comprising any one of them. A pair of linker or spacer sequences that are added to both sides of an MBS may be inverted sequences (mirror-image sequences). For example, AAC can be added to the 5' side of an MBS and CAA can be added to the 3' side.

Nucleic acids constituting the miRNA inhibiting complexes of the present invention are characteristically modified by a specific modified nucleic acid of the present invention, but may comprise a modified nucleic acid other than the specific modified nucleic acid. For example, nucleotides constituting a nucleic acid may comprise, in addition to the specific modified nucleic acids of the present invention, a naturally-occurring nucleotide, modified nucleotide, artificial nucleotide, or combination thereof. As long as the specific modified nucleic acid of the present invention is comprised, nucleic acids comprised in the miRNA inhibiting complexes of the present invention may also consist of RNAs in addition to the specific modified nucleic acid, or may be RNA/DNA chimeras, or may comprise other nucleic acid analogs or any combination thereof. As long as the specific modified nucleic acid of the present invention is comprised, nucleic acids include not only those bound by a phosphodiester bond, but also those having an amide bond or another backbone (peptide nucleic acids (PNAs) and the like). Nucleic acid analogs include, for example, naturally-occurring and artificial nucleic acids. They may also be nucleic acid derivatives, nucleic acid analogs, or the like. Such nucleic acid analogs are well known in the art. Examples thereof include, but are not limited to, phosphorothioate, phosphoramidate, methylphosphonate, chiral methylphosphonate, 2"-O-methylribonucleotide, and peptide nucleic acid (PNA). The PNA backbones may include a backbone consisting of aminoethylglycine, polyamide, polyethyl, polythioamide, polysulfinamide, polysulfonamide, or a combination thereof (Krutzfeldt, J. et al., Nucleic Acids Res. 35: 2885-2892; Davis, S. et al., 2006, Nucleic Acids Res. 34: 2294-2304; Boutla, A. et al., 2003), Nucleic Acids Res. 31: 4973-4980; Hutvagner, G. et al., 2004, PLoS Biol. 2: E98; Chan, J. A. et al., 2005, Cancer Res. 65: 6029-6033; Esau, C. et al., 2004, J. Biol. Chem. 279: 52361-52365; Esau, C. et al., 2006, Cell Metab. 3: 87-98).

(Bridged Nucleic Acid (BNA) Used in the Present Invention)

One of the features of the present invention is to comprise a specific modified nucleic acid, a stabilizing nucleic acid, i.e., a modified nucleic acid promoting double-strand formation, such as, in the broadest sense, a bridged nucleic acid (BNA).

As used herein, "bridged nucleic acid (BNA)" (BNA refers to both Bicyclic Nucleic Acid and Bridged Nucleic Acid; also referred to as "bridged/bicyclic nucleic acid") refers to any modified nucleic acid, which is linked (bridged) between positions 2' and 4' of a nucleic acid to have two cyclic (bicyclic) structures.

In one exemplary embodiment, a bridged nucleic acid can be used as a stabilizing nucleic acid used in the present invention (i.e., modified nucleic acid promoting double-strand formation). Examples of bridged nucleic acids that can be used include those described in Japanese Patent No. 4731324, Pradeep S. Pallan et al., Chem Commun (Camb). 2012 Aug. 25; 48(66): 8195-8197. doi:10.1039/c2cc32286b, including Locked Nucleic Acid (LNA), ethylene nucleic acids such as 2"-0,4"-C-ethylene bridged nucleic acid (ENA), other bridged nucleic acids (BNA), hexitol nucleic acid (HNA), morpholino nucleic acids, tricyclo-DNA (tcDNA), polyether nucleic acids (U.S. Pat. No. 5,908,845) cyclohexene nucleic acids (CeNA), and combinations thereof.

As used herein, "substitution" refers to substitution of a specific hydrogen atom of an organic compound such as a bridged nucleic acid (BNA) with another atom or group of atoms.

As used herein, a "substituent" refers to an atom or a functional group substituting another atom or functional group in a chemical structure of a bridged nucleic acid (BNA) or the like.

Examples of substituents in the present invention include, but are not limited to, alkyl, cycloalkyl, alkenyl, cycloalkenyl, alkynyl, cycloalkynyl, alkoxy, carbocyclic group, heterocyclic group, halogen, hydroxy, thiol, cyano, nitro, amino, carboxy, carbamoyl, acyl, acylamino, thiocarboxy, amido, substituted carbonyl, substituted thiocarbonyl, substituted sulfonyl, and substituted sulfinyl. As for substituents, any substituents apart from hydrogen can be used.

As used herein, substitution refers to substitution of one or more hydrogen atoms in a certain organic compound or a substituent with another atom or group of atoms, or formation of a double or triple bond, unless specifically noted otherwise. It is also possible to remove one hydrogen atom and substitute it with a monovalent substituent or form a double bond with a single bond. In addition, it is possible to remove two hydrogen atoms and substitute them with a divalent substituent or form a triple bond with a single bond.

As used herein, "alkyl" refers to a monovalent group generated by losing one hydrogen atom from an aliphatic hydrocarbon (alkane) such as methane, ethane, or propane. Alkyl is generally represented by $C_nH_{2n+1}$— (wherein n is a positive integer). Alkyl can be a strain or a branched strand. Specific examples thereof can be C1-C2 alkyl, C1-C3 alkyl, C1-C4 alkyl, C1-05 alkyl, C1-C6 alkyl, C1-C7 alkyl, C1-C8 alkyl, C1-C9 alkyl, C1-C10 alkyl, C1-C11 alkyl, or C1-C20 alkyl, or C1-C2 substituted alkyl, C1-C3 substituted alkyl, C1-C4 substituted alkyl, C1-05 substituted alkyl, C1-C6 substituted alkyl, C1-C7 substituted alkyl, C1-C8 substituted alkyl, C1-C9 substituted alkyl, C1-C10 substituted alkyl, C1-C11 substituted alkyl, or C1-C20 substituted alkyl. In this regard, C1-C10 alkyl, for example, refers to a straight or branched alkyl with 1 to 10 carbon atoms. As used herein, "substituted alkyl" refers to alkyl having H of alkyl substituted with a substituent defined herein. Specific examples thereof include, but are not limited to, $CH_3OCH_2$—, $CH_3OCH_2CH_2$—, $CH_3OCH_2CH_2CH_2$—, $HOCH_2$—, $HOCH_2CH_2$—, $HOCH_2CH_2CH_2$—, $NCCH_2$—, $NCCH_2CH_2$—, $NCCH_2CH_2CH_2$—, $FCH_2$—, $FCH_2CH_2$—, $FCH_2CH_2CH_2$—, $H_2NCH_2$—, $H_2NCH_2CH_2$—, $H_2NCH_2CH_2CH_2$—, $HOOCCH_2$—, $HOOCCH_2CH_2$—, and $HOOCCH_2CH_2CH_2$—.

As used herein, "alkylene" refers to a divalent group generated by losing two hydrogen atoms from an aliphatic hydrocarbon (alkane) such as methane, ethane, or propane. Alkyl is generally represented by —$C_nH_{2n}$— (wherein n is a positive integer). Alkylene can be a strain or branched strand. As used herein, "substituted alkylene" refers to alkylene with H of alkylene substituted with an aforementioned substituent. Specific examples thereof can be C1 alkylene, C1-C2 alkylene, C1-C3 alkylene, C1-C4 alkylene, C1-05 alkylene, C1-C6 alkylene, C1-C7 alkylene, C1-C8 alkylene, C1-C9 alkylene, C1-C10 alkylene, C1-C11 alkylene or, C1-C20 alkylene, or C1-C2 substituted alkylene, C1-C3 substituted alkylene, C1-C4 substituted alkylene, C1-C5 substituted alkylene, C1-C6 substituted alkylene, C1-C7 substituted alkylene, C1-C8 substituted alkylene, C1-C9 substituted alkylene, C1-C10 substituted alkylene, C1-C11 substituted alkylene or C1-C20 substituted alkylene. In this regard, C1-C10 alkylene, for example, refers to a straight or branched alkylene with 1 to 10 carbon atoms. For example, C1-C10 substituted alkylene refers to C1-C10 alkylene having one or more hydrogen atoms substituted with a substituent. As used herein, "alkylene" may comprise one or more atoms selected from an oxygen atom and a sulfur atom.

As used herein, "cycloalkyl" refers to alkyl having a cyclic structure. "Substituted cycloalkyl" refers to cycloalkyl having H of cycloalkyl substituted with an aforementioned substituent. Specific examples thereof can be C3-C4 cycloalkyl, C3-C5 cycloalkyl, C3-C6 cycloalkyl, C3-C7 cycloalkyl, C3-C8 cycloalkyl, C3-C9 cycloalkyl, C3-C10 cycloalkyl, C3-C11 cycloalkyl, C3-C20 cycloalkyl, C3-C4 substituted cycloalkyl, C3-05 substituted cycloalkyl, C3-C6 substituted cycloalkyl, C3-C7 substituted cycloalkyl, C3-C8 substituted cycloalkyl, C3-C9 substituted cycloalkyl, C3-C10 substituted cycloalkyl, C3-C11 substituted cycloalkyl, or C3-C20 substituted cycloalkyl.

As used herein, "alkenyl" refers to a monovalent group generated by losing one hydrogen atom from an aliphatic hydrocarbon having a double bond in the molecule. Alkenyl is generally represented by $C_nH_{2n-1}$— (wherein n is a positive integer that is 2 or greater). "Substituted alkenyl" refers to alkenyl with H of alkenyl substituted with an aforementioned substituent. Specific examples thereof can be C2-C3 alkenyl, C2-C4 alkenyl, C2-C5 alkenyl, C2-C6 alkenyl, C2-C7 alkenyl, C2-C8 alkenyl, C2-C9 alkenyl, C2-C10 alkenyl, C2-C11 alkenyl, C2-C20 alkenyl, or C2-C3 substituted alkenyl, C2-C4 substituted alkenyl, C2-O5 substituted alkenyl, C2-C6 substituted alkenyl, C2-C7 substituted alkenyl, C2-C8 substituted alkenyl, C2-C9 substituted alkenyl, C2-C10 substituted alkenyl, C2-C11 substituted alkenyl, or C2-C20 substituted alkenyl. In this regard, C2-C10 alkyl, for example, refers to straight or branched alkenyl comprising 2 to 10 carbon atoms. For example, C2-C10 substituted alkenyl refers to C2-C10 alkenyl with one or more hydrogen atoms substituted with a substituent.

As used herein, "aryl" refers to a group generated by one hydrogen atom binding to an aromatic hydrocarbon ring leaving. As used herein, aryl is encompassed by carbocyclic group. A phenyl group ($C_6H_5$—) is induced form benzene, tolyl group ($CH_3C_6H_4$—) is induced from toluene, xylyl group (($CH_3)_2C_6H_3$—) is induced form xylene, and naphthyl group ($C_{10}H_8$—) is induced form naphthalene.

As used herein, "aralkyl" refers to an alkyl group with one hydrogen atom of an alkyl group substituted with an aryl group. Specific examples of an aralkyl group can be benzyl groups, phenethyl group, 1-naphthyl ethyl group or the like.

As used herein, "acyl" refers to a monovalent group, which is produced by removing OH from carboxylic acid. Representative examples of acyl groups include acetyl ($CH_3CO$—), benzoyl ($C_6H_5CO$—) and the like. "Substituted acyl" refers to acyl with H substituted with an aforementioned substituent.

As used herein, "sulfonyl" collectively refers to those comprising the characteristic group —$SO_2$—. "Substituted sulfonyl" refers to sulfonyl having a substitution with an aforementioned substituent.

As used herein, "silyl" is generally a group represented by $SiR_1R_2R_3$— (wherein $R_1$, $R_2$, and $R_3$ are each independently selected from the group consisting of hydrogen, alkyl, cycloalkyl, alkenyl, cycloalkenyl, alkynyl, cycloalkynyl, alkoxy, carbocyclic group, and heterocyclic group. Specific examples thereof can be trimethylsilyl group, triethylsilyl group, tri-n-propyl silyl group, tert-butyldimethylsilyl group, triisopropylsilyl group, or tert-butyldiphenylsilyl group.

As used herein, "functional molecule unit substituent" refers to groups including labeling molecules (e.g., molecule species including fluorescent molecules, chemiluminescent molecules, radioactive isotope atoms, and the like), DNA or RNA cleavage activity molecules, intracellular or nuclear translocation signal peptides and the like.

In one embodiment, the BNA can be a BNA that is bridged via at least one atom selected from the group consisting of oxygen and carbon on the position 2' side and via at least one atom selected from the group consisting of carbon and nitrogen and carbon on the position 4' side.

In a representative embodiment, the BNA used in the present invention is a 2',4' substituted bridged nucleic acid represented by

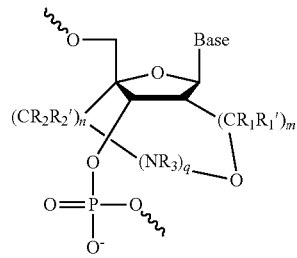

BNA-1 wherein $R_1$, $R_1'$, $R_2$, $R_2'$, and $R_3$ each independently represent a group selected from the group consisting of a hydrogen atom, a substituted or unsubstituted alkyl group, a substituted or unsubstituted alkenyl group, a substituted or unsubstituted cycloalkyl group, a substituted or unsubstituted aryl group, a substituted or unsubstituted aralkyl group, a substituted or unsubstituted acyl group, a substituted or unsubstituted sulfonyl group, a substituted or unsubstituted silyl group, and a functional molecule unit substituent, such as, but not limited to, a substituted or unsubstituted phenoxyacetyl group, alkyl group with 1 to 5 carbons, alkenyl group with 1 to 5 carbons, aryl group with 6 to 14 carbons, methyl group substituted with 1 to 3 aryl groups, lower aliphatic or aromatic sulphonyl group such as methane sulphonyl group and p-toluene sulphonyl group, aliphatic acyl group with 1 to 5 carbons such as acetyl group, or aromatic acyl group such as benzoyl group, n is an integer from 1 to 3, and q is an integer that is 0 or 1.

Base is a purine-9-yl group, a 2-oxo-pyrimidine-1-yl group, or a derivative thereof. Base is exemplified in Japanese Patent No. 4731324, and typical examples thereof in the present invention include, but are not limited to, 6-aminopurine-9-yl (i.e., adeninyl), 2-amino-6-chloropurine-9-yl, 2-amino-6-fluoropurine-9-yl, 2-amino-6-bromopurine-9-yl, 2-amino-6-hydroxypurine-9-yl (i.e., guaninyl), 6-amino-2-chloropurine-9-yl, 6-amino-2-fluoropurine-9-yl, 2,6-dimethoxypurine-9-yl, 2,6-dichloropurine-9-yl, 6-mercaptopurine-9-yl, 2-oxo-4-amino-1, 2-dihydropyrimidine-1-yl (i.e., cytosinyl), 2-oxo-4-amino-5-fluoro-1,2-dihydropyrimidine-1-yl, 4-amino-2-oxo-5-chloro-1,2-dihydropyrimidine-1-yl, 2-oxo-4-methoxy-1,2-dihydropyrimidine-1-yl, 2-oxo-4-mercapto-1,2-dihydropyrimidine-1-yl, 2-oxo-4-hydroxy-1, 2-dihydropyrimidine-1-yl (i.e., uracilyl), 2-oxo-4-hydroxy-5-methyl-1,2-dihydropyrimidine-1-yl (i.e., thyminyl), 4-amino-5-methyl-2-oxo-1,2-dihydropyrimidine-1-yl (e.g., 5-methylcytosinyl), 9-β-D-ribofuranosyl hypoxanthinyl (i.e., inosinyl) and derivatives thereof, preferably adeninyl, thyminyl, guaninyl, uracilyl, inosinyl, cytosinyl, 5-methylcytosinyl, and derivatives thereof.

In another representative embodiment, the BNA used in the present invention includes a 2',4' substituted bridged nucleic acid represented by

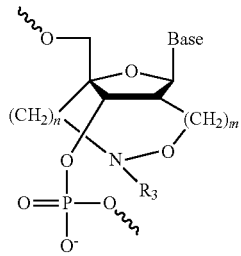

BNA-2 wherein R₃ represents a group selected from the group consisting of a hydrogen atom, a substituted or unsubstituted alkyl group, a substituted or unsubstituted alkenyl group, a substituted or unsubstituted cycloalkyl group, a substituted or unsubstituted aryl group, a substituted or unsubstituted aralkyl group, a substituted or unsubstituted acyl group, a substituted or unsubstituted sulfonyl group, a substituted or unsubstituted silyl group, and a functional molecule unit substituent, such as, but not limited to, a phenoxyacetyl group, alkyl group with 1 to 5 carbons, alkenyl group with 1 to 5 carbons, aryl group with 6 to 14 carbons, methyl group substituted with 1 to 3 aryl groups, lower aliphatic or aromatic sulphonyl group such as methane sulphonyl group and p-toluene sulphonyl group, aliphatic acyl group with 1 to 5 carbons such as acetyl group, or aromatic acyl group such as benzoyl group, m is an integer from 0 to 2, and n is an integer from 1 to 3. Base is the same as the explanation for BNA-1, which can be preferably adeninyl, guaninyl, thyminyl, uracilyl, inosinyl, cytosinyl, 5-methylcytosinyl, and derivatives thereof.

In another representative embodiment, the BNA used in the present invention is

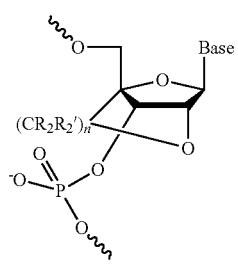

BNA-3 wherein R₂ and R₂' each independently represent a group selected from the group consisting of a hydrogen atom, a substituted or unsubstituted alkyl group, a substituted or unsubstituted alkenyl group, a substituted or unsubstituted cycloalkyl group, a substituted or unsubstituted aryl group, a substituted or unsubstituted aralkyl group, a substituted or unsubstituted acyl group, a substituted or unsubstituted sulfonyl group, a substituted or unsubstituted silyl group, and a functional molecule unit substituent, such as, but not limited to, a methyl group or O-methoxyethyl group, and Base is the same as the explanation for BNA-1, which can be preferably adeninyl, guaninyl, thyminyl, uracilyl, inosinyl, cytosinyl, 5-methylcytosinyl, and derivatives thereof, wherein n is an integer from 1 to 3, but one of R₂ and R₂' is not hydrogen.

Examples of BNAs with a branch in a bridged strand are, but not limited thereto, BNA(cEt)

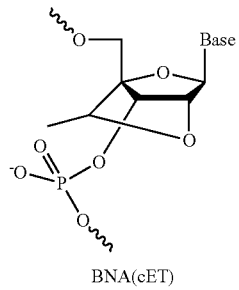

BNA(cET)

(cEt: 2',4'-constrained ethyl). Although BNA(cEt) has thermostability and mismatch identification similar to conventional LNAs, it is known to have improved stability against nuclease.

In a representative embodiment, the BNA used in the present invention may be

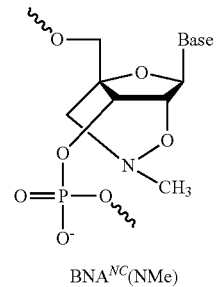

BNA$^{NC}$(NMe)

(which is denoted herein as "BNA$^{NC}$(NMe)" unless specifically noted otherwise), but may also be described as "2',4'-BNANC"), wherein Base has the same aforementioned definition, which is preferably selected from the group consisting of adeninyl, thyminyl, guaninyl, uracilyl, inosinyl, cytosinyl, and 5-methylcytosinyl.

As used herein, a "protecting group" refers to a group used for protecting a functional group from a specific chemical reaction. As used herein, a protecting group may be denoted as "PG".

Preferably, BNA$^{NC}$(NMe) or LNA, more preferably BNA$^{NC}$(NMe), is used as a BNA.

In a preferred embodiment, m is 0 and n is 1.

Thus, when used in miRNAs, this can be an oligonucleotide or a pharmacologically acceptable salt thereof as a DNA oligonucleotide or an RNA oligonucleotide comprising one or more of one or more types of unit structures of nucleosides represented by the general formula (BNA-1), (BNA-2), (BNA-3), BNA(cEt), or BNA$^{NC}$(NMe). In this regard, the form of bond between each nucleoside in an oligonucleotide may comprise one or more phosphothioate bonds [—OP(O)(S—)O—] besides a phosphodiester bond [—OP(O₂—) O—] which is the same as a naturally-occurring nucleic acid. When comprising two or more of one or more types of the aforementioned structures, Base can be the same or different between the structures.

A DNA or RNA oligonucleotide analog comprising an artificial nucleic acid BNA$^{NC}$(NMe), which is one type of the present invention, has the following excellent characteristic. This is because the capability to form a double strand with respect to a complementary RNA strand is extremely high.

(1) The Tm value increases 3 to 6° C. for each BNA$^{NC}$(NMe) introduced into a DNA oligonucleotide (per one modification). Moreover, there is hardly any increase (improvement) in the capability to form a double strand with respect to a complementary DNA strand. This characteristic entails a dramatic increase in the Tm value (significant improvement in the capability to form a double strand) as in BNA modified DNA oligonucleotides in binding affinity to complementary RNA strands, but improvement in the capability to form a double strand with respect to a complementary DNA strand is observed in BNA modified DNA oligonucleotides compared to unmodified DNA oligonucleotides (increase of 2 to 4° C. in the Tm value per modification). In contrast, improvement in binding affinity is hardly observed in BNA$^{NC}$ (NMe) modified DNA oligonucleotides. Thus, BNA$^{NC}$ (NMe) modified DNA oligonucleotides have excellent selective binding affinity to an RNA strand.

(2) BNA$^{NC}$(NMe) modified DNA oligonucleotides also have superior capability to form a triple strand with respect to a double-stranded DNA strand.

The Tm value increases 7 to 12° C. in forming a triple strand with respect to a double-stranded DNA strand when a BNA$^{NC}$(NMe) unit is introduced into a DNA oligonucleotide. Further, a triple strand formation requires sequence selectivity for strictly identifying a base sequence and binding only to a target sequence. The difference in the Tm value for a matching sequence and a mismatching sequence of a BNA$^{NC}$(NMe) modified DNA oligonucleotide is 25° C. or greater, thus having better sequence selectivity than a naturally-occurring DNA oligonucleotide. The nuclease resistance is superb for BNA$^{NC}$(NMe).

BNA$^{NC}$(NMe) modified oligonucleotides have higher nuclease resistance than naturally-occurring DNA oligonucleotides, but much lower than S-oligo (phosphorothioate oligonucleotide). The BNA$^{NC}$(NMe) modified oligonucleotide of the present invention has better nuclease resistance than S-oligo, which is highly valued for its excellent nuclease resistance, not to mention BNA modified oligonucleotides. The BNA$^{NC}$ (NMe) modified oligonucleotide of the present invention is also characterized by strongly resisting degradation in vivo.

(3) The N—O bond comprised in the artificial nucleic acid, BNA$^{NC}$ (NMe) of the present invention, can be selectively cleaved under moderate conditions with a reducing reagent to free an NH group and an OH group. By using the NH group and the OH group to bind a molecule with another function, various complexes (conjugates) can be readily obtained, before or after the preparation of an oligonucleotide analog. Labeling molecules such as molecular species including fluorescent molecules, chemiluminescent molecules, and radioactive isotope atoms, or the like, various DNA (RNA) cleavage activity molecules, intracellular or nuclear translocation signal peptides or the like can be used as molecules with another function.

(4) DNA or RNA oligonucleotide analogs with a BNA$^{NC}$ (NMe) modification in various forms are highly useful not only as highly functional materials for development of genetic medicaments using antisense method, antigene method, decoy method, gene homologous recombination, RNA interference process, or the like, but also as a substrate for gene diagnosis methods such as a molecular beacon or DNA chip, or as material for developing reagents used for research such as gene function analysis/elucidation.

Examples of suitable compounds among the compounds (BNA-1) of the present invention and salts thereof include (5) compounds in which R$_3$ is a hydrogen atom, alkyl group with 1 to 5 carbons, alkenyl group with 1 to 5 carbons, aryl group with 6 to 14 carbons, methyl group substituted with 1 to 3 aryl groups, lower aliphatic or aromatic sulphonyl group such as methane sulphonyl group or p-toluene sulphonyl group, aliphatic acyl group with 1 to 5 carbons such as acetyl group, aromatic acyl group such as benzoyl group or phenoxyacetyl group, or a salt thereof, and compounds in which a functional molecule unit substituent of R$_3$ is a fluorescent or chemiluminescent labeling molecule, nucleic acid cleavage activity molecule, or intracellular or nuclear translocation signal peptides, and (6) Base is as disclosed above, preferably an adeninyl group, a thyminyl group, a uracilyl group, an inosinyl group, a cytosinyl group, a guaninyl group, a methylcytosinyl group, or a derivative thereof.

The nucleoside analog and oligonucleotide analog of the present invention can be synthesized based on the methods described in the Examples and conventional techniques in the art.

<1> Synthesis of Nucleoside Analog ((BNA-1) and (BNA-2))

Compounds represented by the general formulas (BNA-1) and (BNA-2) can be synthesized based on the methods described in the Examples and conventional techniques in the art. The methods described in the Examples can be referred to for the specific reaction conditions, protecting group introducing reagent, and reaction reagent, but they are not limited thereto. Reaction conditions and reagents that can be used based on the common general knowledge of the art can be appropriately used. For example, the methods described in Japanese Laid-Open Publication No. 2000-297097 or Japanese Laid-Open Publication No. 10-304889 can be referred to. The raw materials for the compounds of the present invention can be synthesized by referring to the method described in Japanese Laid-Open Publication No. 10-304889 when Base in general formulas (BNA-1) and (BNA-2) has various naturally-occurring or non-naturally-occurring nucleic acid base and other aromatic heterocycle or aromatic hydrocarbon ring.

(General Synthesis Example for Nucleoside Analogs)

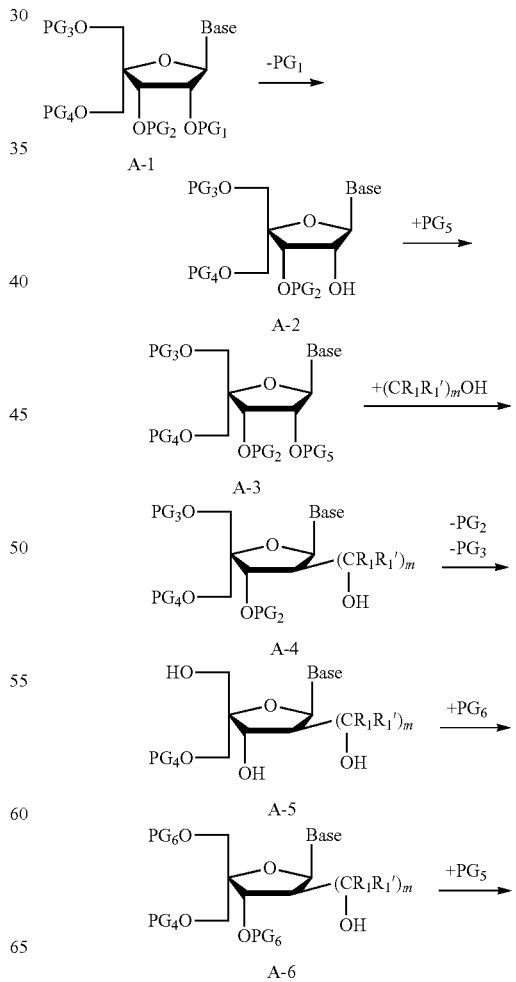

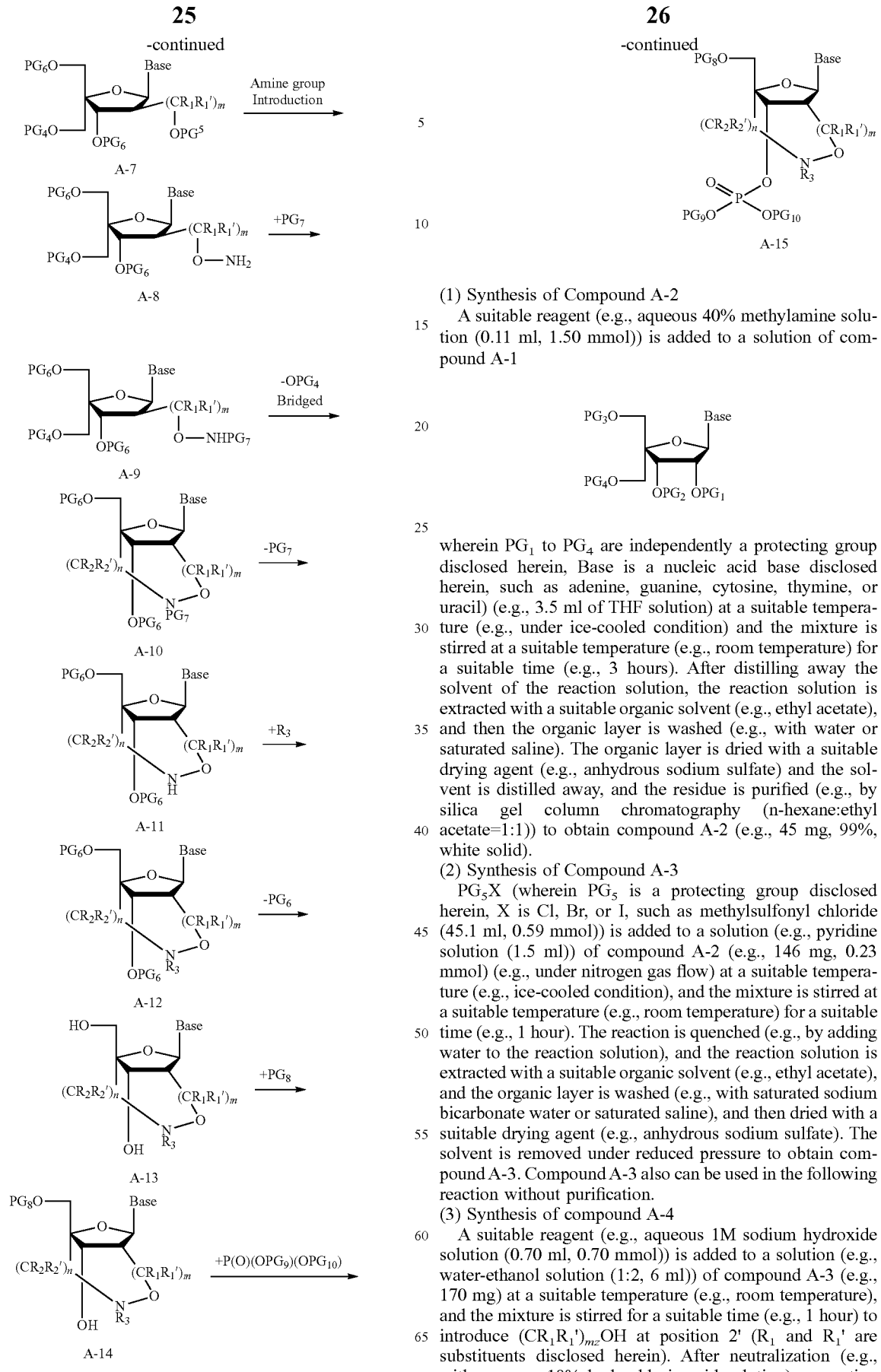

(1) Synthesis of Compound A-2

A suitable reagent (e.g., aqueous 40% methylamine solution (0.11 ml, 1.50 mmol)) is added to a solution of compound A-1 wherein $PG_1$ to $PG_4$ are independently a protecting group disclosed herein, Base is a nucleic acid base disclosed herein, such as adenine, guanine, cytosine, thymine, or uracil) (e.g., 3.5 ml of THF solution) at a suitable temperature (e.g., under ice-cooled condition) and the mixture is stirred at a suitable temperature (e.g., room temperature) for a suitable time (e.g., 3 hours). After distilling away the solvent of the reaction solution, the reaction solution is extracted with a suitable organic solvent (e.g., ethyl acetate), and then the organic layer is washed (e.g., with water or saturated saline). The organic layer is dried with a suitable drying agent (e.g., anhydrous sodium sulfate) and the solvent is distilled away, and the residue is purified (e.g., by silica gel column chromatography (n-hexane:ethyl acetate=1:1)) to obtain compound A-2 (e.g., 45 mg, 99%, white solid).

(2) Synthesis of Compound A-3

$PG_5X$ (wherein $PG_5$ is a protecting group disclosed herein, X is Cl, Br, or I, such as methylsulfonyl chloride (45.1 ml, 0.59 mmol)) is added to a solution (e.g., pyridine solution (1.5 ml)) of compound A-2 (e.g., 146 mg, 0.23 mmol) (e.g., under nitrogen gas flow) at a suitable temperature (e.g., ice-cooled condition), and the mixture is stirred at a suitable temperature (e.g., room temperature) for a suitable time (e.g., 1 hour). The reaction is quenched (e.g., by adding water to the reaction solution), and the reaction solution is extracted with a suitable organic solvent (e.g., ethyl acetate), and the organic layer is washed (e.g., with saturated sodium bicarbonate water or saturated saline), and then dried with a suitable drying agent (e.g., anhydrous sodium sulfate). The solvent is removed under reduced pressure to obtain compound A-3. Compound A-3 also can be used in the following reaction without purification.

(3) Synthesis of compound A-4

A suitable reagent (e.g., aqueous 1M sodium hydroxide solution (0.70 ml, 0.70 mmol)) is added to a solution (e.g., water-ethanol solution (1:2, 6 ml)) of compound A-3 (e.g., 170 mg) at a suitable temperature (e.g., room temperature), and the mixture is stirred for a suitable time (e.g., 1 hour) to introduce $(CR_1R_1')_m$OH at position 2' ($R_1$ and $R_1'$ are substituents disclosed herein). After neutralization (e.g., with aqueous 10% hydrochloric acid solution), a reaction solution is extracted with a suitable organic solvent (e.g., ethyl acetate). After washing an organic layer (e.g., with water or saturated saline), this is dried with a suitable drying agent (e.g., anhydrous sodium sulfate). The solvent is distilled away under reduced pressure. The resulting crude product is purified (e.g., by silica gel column chromatography (chloroform:methanol=15:1) to obtain compound A-4 (e.g., 139 mg, 95% (2 stages), white solid).

(4) Synthesis of Compound A-5

A suitable reagent (e.g., 20% palladium hydroxide-carbon powder (0.60 g), cyclohexene (5.2 ml, 51 mmol)) is added to a solution (e.g., ethanol solution (10 ml)) of compound A-4 (e.g., 0.80 g, 1.28 mmol) (e.g., under nitrogen gas flow) and the mixture is stirred for a suitable time (e.g., 5 hours) under a suitable temperature condition (e.g., heating under reflux) to remove $PG_2$ and $PG_3$. The step of removing $PG_2$ and the step of removing $PG_3$ may be the same or different steps. After filtering the reaction solution, the solvent is distilled away under reduced pressure. The resulting crude product A-5 can be used in the following reaction without purification.

(5) Synthesis of Compound A-6

$PG_6X$ (wherein $PG_6$ is a protecting group disclosed herein and X is Cl, Br, or I, such as 1,3-dichloro-1,1,3,3-tetraisopropyldisiloxane (0.45 ml, 1.41 mmol)) and base (e.g., imidazole (0.38 g, 5.63 mmol)) are added to a solution (e.g., N,N-dimethylformamide solution (10 ml)) of compound A-5 (e.g., 0.46 g) (e.g., under nitrogen gas flow), and the mixture is stirred at a suitable temperature (e.g., room temperature) for a suitable time (e.g., 5 hours) to introduce $PG_6$. A reaction solution is extracted with a suitable organic solvent (e.g., ether). The organic layer is washed (e.g., with water or saturated saline), and then dried with a suitable drying agent (e.g., magnesium sulfate). The solvent is distilled away under reduced pressure, and the resulting crude product is purified (e.g., by silica gel column chromatography (n-hexane:ethyl acetate=2:1→1:1)) to obtain compound A-6 (e.g., 0.60 g, 68% (2 stages), white solid).

(6) Synthesis of Compound A-7

$PG_5X$ (wherein $PG_5$ is a protecting group disclosed herein and X is Cl, Br, or I, such as anhydrous trifluoromethanesulfonic acid (0.15 ml, 0.88 mmol)) and base (e.g., 4-(dimethylamino)pyridine (7 mg, 0.06 mmol)) are added to a solution (e.g., pyridine solution (3 ml)) of compound A-6 (e.g., 200 mg, 0.29 mmol) (e.g., under nitrogen gas flow) at a suitable temperature (e.g., under ice cooled condition). The mixture is stirred at a suitable temperature (e.g., room temperature) for a suitable time (e.g., 7.5 hours). The reaction is quenched (e.g., by adding water to the reaction solution) to extract the reaction solution with a suitable organic solvent (e.g., dichloromethane). The organic layer is washed (e.g., with saturated sodium bicarbonate water or saturated saline) and then dried with a suitable drying agent (e.g., anhydrous sodium sulfate). The solvent is distilled away under reduced pressure to obtain compound A-7. The resulting A-7 can be used in the following reaction without purification.

(7) Synthesis of Compound A-8

Compound A-8 introduced with an amino group in a hydroxy group at position 2' of compound A-7 is synthesized. The synthesis method thereof is not limited. The method includes, for example, the following. A suitable reagent (e.g., N-hydroxyphthalimide (67 mg, 0.41 mmol) or 1,8-diazabicyclo[5.4.0]-7-undecene (61 (1, 0.41 mmol)) is added to a solution (e.g., acetonitrile solution (3 ml)) of compound A-7 (e.g., 0.29 g) (under nitrogen gas flow) at a suitable temperature (e.g., room temperature), and the mixture is stirred at a suitable temperature (e.g., room temperature) for a suitable time (e.g., 12 hours). The reaction solution is extracted with a suitable organic solvent (e.g., dichloromethane). The organic layer is washed (e.g., with water or saturated saline) and then dried with a suitable drying agent (e.g., anhydrous sodium sulfate). The solvent is distilled away under reduce pressure and the resulting crude product is purified (e.g., by silica gel column chromatography (chloroform)) to obtain compound A-7'. A suitable reagent (e.g., hydrazine monohydrate (0.12 ml, 2.38 mmol)) is added to a solution (e.g., ethanol solution (35 ml)) of the resulting compound A-7' (1.16 g, 1.40 mmol), and the mixture is stirred at a suitable temperature (e.g., room temperature) for a suitable time (e.g., 10 minutes). After distilling away the solvent of the reaction solution, the solution is filtered, and a filtrate is extracted with a suitable organic solvent (e.g., ethyl acetate). The organic layer is washed (e.g., with water or saturated saline), then dried with a suitable drying agent (anhydrous sodium sulfate). The solvent is distilled away under reduced pressure. The obtained A-8 can be used in the following reaction without purification.

(8) Synthesis of Compound A-9

A suitable reagent (e.g., saturated sodium bicarbonate water (4.0 ml, 4.2 mmol)) and $PG_7X$ (wherein $PG_7$ is a protecting group disclosed herein and X is Cl, Br, or I, such as benzyl chloroformate (0.30 ml, 2.1 mmol)) are added to a solution (e.g., methylene chloride solution (15 ml)) of compound A-8 (0.93 g) (e.g., under nitrogen gas flow) at a suitable temperature (e.g., under ice-cooling condition), and the mixture is stirred for a suitable time (e.g., 1 hour). The reaction is quenched (e.g., by adding saturated sodium bicarbonate water), and the reaction solution is extracted with a suitable organic solvent (e.g., ethyl acetate). The organic layer is washed (e.g., with water or saturated saline), and dried with a suitable drying agent (e.g., magnesium sulfate). The solvent is distilled away under reduced pressure and the resulting crude product is purified (e.g., by silica gel column chromatography (n-hexane-ethyl acetate=4:1)) to obtain compound A-9 (e.g., 0.92 g, 94% (2 stages), white solid).

(9) Synthesis of Compound A-10

A solution (e.g., tetrahydrofuran solution (15 ml)) of compound A-9 (e.g., 3.81 g, 4.57 mmol) is dripped into a base (e.g., tetrahydrofuran suspension (25 ml) of sodium hydroxide (60% in oil, 0.55 g, 13.7 mmol) (e.g., under nitrogen gas flow) at a suitable temperature (e.g., under ice-cooled condition), and the mixture is stirred for a suitable time (e.g., 1 hour). After stirring at a suitable temperature (e.g., room temperature) for a suitable time (e.g., 5 hours), $OPG_4$ and bridges positions 2' and 4' are removed. The step of removing $OPG_4$ and the step of bridging positions 2' and 4' may be the same or different steps. After neutralization (e.g., with saturated aqueous oxalic acid solution), a reaction solution is extracted with a suitable organic solvent (e.g., ethyl acetate). The organic layer is washed (e.g., with water or saturated saline), then dried with a suitable drying agent (e.g., anhydrous sodium sulfate). The solvent is distilled away under reduced pressure, and the resulting crude product is purified (e.g., by silica gel column chromatography (chloroform→chloroform:methanol=100: 1)) to obtain compound A-10 (e.g., 2.87 g, 95%, white solid).

(10) Synthesis of Compound A-11

A suitable reagent (e.g., 1M boron trichloride hexane solution (5.29 ml, 5.29 mmol)) is added to a solution (e.g., methylene chloride solution (10 ml)) of compound A-10

(e.g., 0.35 mg, 0.53 mmol) (e.g., under nitrogen gas flow) at a suitable temperature (e.g., under ice-cooled condition), and the mixture is stirred for a suitable time (e.g., 1 hour). The reaction is quenched (e.g., by adding saturated sodium bicarbonate water to the reaction solution). The reaction solution is extracted with a suitable organic solvent (e.g., ethyl acetate). The organic layer is washed (e.g., with water or saturated saline), and then dried with a suitable drying agent (e.g., anhydrous sodium sulfate). The solvent is distilled away under reduced pressure, and the resulting crude product is purified (e.g., by silica gel column chromatography (chloroform: methanol=50:1)) to obtain compound A-11 (e.g., 0.27 g, 96%, white solid).

(11) Synthesis of Compound A-12

A suitable reagent (e.g., aqueous 20% formaldehyde solution (0.06 ml, 0.40 mmol)) is added to a solution (e.g., 1 M pyridinium p-toluenesulfonate-methanol solution (3.6 ml)) of compound A-11 (0.19 g, 0.36 mmol) at a suitable temperature (e.g., room temperature), and the mixture is stirred for a suitable time (e.g., 10 minutes). Furthermore, a suitable reagent (e.g., sodium cyanoborohydride (45 mg, 0.72 mmol)) is added at a suitable temperature (e.g., under ice-cooled condition) to substitute an amino group with substituent $R_3$ ($R_3$ is a substituent disclosed herein). The mixture is stirred for a suitable time (e.g., 1 hour). The reaction solution is extracted with a suitable organic solvent (e.g., ethyl acetate) and washed (e.g., with water, saturated sodium bicarbonate water, or saturated saline). The organic layer is dried with a suitable drying agent (e.g., with anhydrous sodium sulfate). The solvent is distilled away under reduced pressure, and the resulting crude product is purified (e.g., by silica gel column chromatography (n-hexane:ethyl acetate=2:1)) to obtain compound A-12 (e.g., 0.19 g, 100%, white solid).

(12) Synthesis of Compound A-13

A suitable reagent (e.g., fluorinated tetra-n-butylammonium (0.17 ml, 0.17 mmol in 1M tetrahydrofuran)) is added to a solution (e.g., tetrahydrofuran solution (2 ml)) of compound A-12 (46 mg, 0.085 mmol), and the mixture is stirred at a suitable temperature (e.g., room temperature) for a suitable time (e.g., 5 minutes). The solvent is distilled away under reduced pressure, and the resulting crude product is purified (e.g., by silica gel column chromatography (ethyl acetate:methanol=15:1)) to obtain compound A-13 (e.g., 25 mg, 100%, white solid).

(13) Synthesis of Compound A-14

A suitable reagent (e.g., 4,4'-dimethoxytrityl chloride (e.g., 0.22 g, 0.64 mmol)) is added to a solution (e.g., pyridine solution (10 ml)) of compound A-13 (e.g., 0.16 g, 0.54 mmol), and the mixture is stirred at a suitable temperature (e.g., room temperature) for a suitable time (e.g., 12 hours). For example, saturated sodium bicarbonate water is added to a reaction solution, and the reaction solution is extracted with a suitable organic solvent (e.g., ethyl acetate). The organic layer is washed (e.g., with water or saturated saline), and then dried with a suitable drying agent (e.g., anhydrous sodium sulfate). The solvent is distilled away under reduced pressure, and the resulting crude product is purified (e.g., by silica gel column chromatography (1% trimethylamine containing n-hexane:ethyl acetate=1: 2→ethyl acetate:methanol=30:1)) to obtain compound A-14 (e.g., 0.30 g, 93%, white solid).

(14) Synthesis of Compound A-15

A suitable reagent (e.g., 2-cyanoethyl-N,N,N',N'-tetraisopropylphosphoroamidite (0.13 ml, 0.42 mmol)) is added to a solution (e.g., acetonitrile solution (6 ml)) of compound A-14 (e.g., 0.17 g, 0.28 mmol) and a suitable reagent (e.g., 4,5-dicyanoimidazole (40 mg, 0.34 mmol)), and the mixture is stirred at a suitable temperature (e.g., room temperature) for a suitable time (e.g., 4 hours) to modify a hydroxy group at position 3' with P(O) (OPG$_9$) (OPG$_{10}$) (PG$_9$ and PG$_{10}$ are each independently a protecting group disclosed herein). The reaction is quenched (e.g., by adding saturated sodium bicarbonate water to a reaction solution), and the reaction solution is extracted with a suitable organic solvent (e.g., ethyl acetate). The organic layer is washed (e.g., with saturated sodium bicarbonate water, water, or saturated saline), and then dried with a suitable drying agent (e.g., anhydrous sodium sulfate). The solvent is distilled away under reduced pressure. The resulting crude product is purified (e.g., by silica gel column chromatography (1% triethylamine containing n-hexane:ethyl acetate=1:1) and then re-precipitated (ethyl acetate-hexane) to obtain compound A-15 (e.g., 0.20 g, 88%, white solid).

(BNA-3)

A compound represented by general formula BNA-3 can be synthesized based on the method disclosed in the Examples and conventional techniques in the art. The methods described in the Examples can be referred to for the specific reaction conditions, protecting group introducing reagent, and reaction reagent, but they are not limited thereto. Reaction conditions and reagents that can be used based on the common general knowledge of the art can be appropriately used. For example, the methods described in J. Org. Chem. 2010, 75, 1569-1581 can be referred to. The raw materials for the compounds of the present invention can be synthesized by referring to the method described in J. Org. Chem. 2010, 75, 1569-1581 when Base in general formula (BNA-3) has various naturally-occurring or non-naturally-occurring nucleic acid bases and other aromatic heterocycles or aromatic hydrocarbon rings.

General Synthesis Example of BNA-3

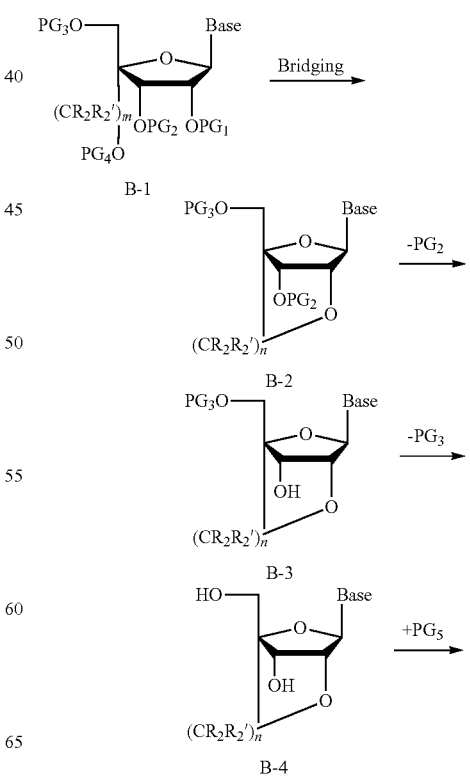

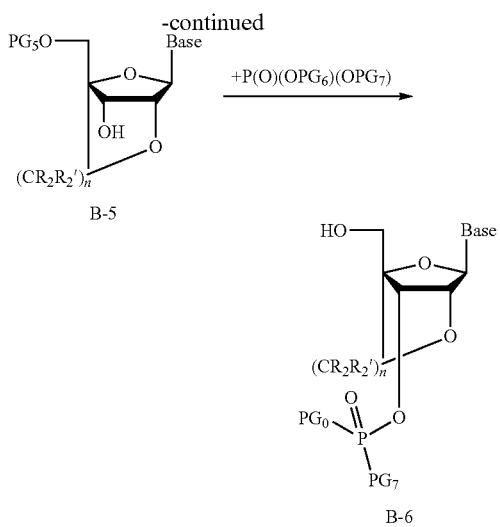

B-5

B-6

(1) Synthesis of Compound B-2

A suitable reagent (e.g., potassium carbonate) is added to a solution of compound B-1

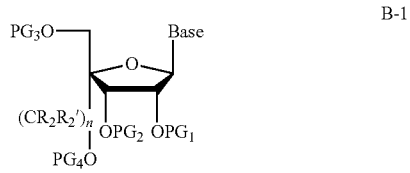

B-1 wherein $PG_1$ to $PG_4$ are independently a protecting group disclosed herein, $R_2$ and $R_2'$ are substituents disclosed herein, and Base is a nucleic acid base disclosed herein, such as an adeninyl group, a thyminyl group, a guaninyl group, or a methylcytosinyl group) at a suitable temperature (e.g., under nitrogen gas flow), and the mixture is stirred at a suitable temperature for a suitable time. The reaction is quenched (e.g., by adding water to the reaction solution), and the reaction solution is extracted with a suitable organic solvent (e.g., ethyl acetate). The organic layer is washed (e.g., with saturated saline). The organic layer is dried with a suitable drying agent (e.g., sodium sulfate). After distilling away the solvent, the residue is purified (e.g., with silica gel column chromatography) to obtain compound B-2.

(2) Synthesis of Compound B-3

A suitable reagent (e.g., 2,3-dichloro-5,6-dicyano-p-benzoquinone (DDQ) is added to a solution of compound B-2 (e.g., under nitrogen gas flow) at a suitable temperature (e.g., room temperature), and the mixture is stirred at a suitable temperature (e.g., room temperature) for a suitable time (e.g., 12 hours). The reaction is quenched (e.g., by adding water to the reaction solution), and the reaction solution is extracted with a suitable organic solvent (e.g., ethyl acetate). The organic layer is washed (e.g., with saturated saline), and then dried with a suitable drying agent (e.g., anhydrous sodium sulfate). The solvent is distilled away under reduced pressure to obtain compound B-3.

(3) Synthesis of Compound B-4

A suitable reagent (e.g., triethylamine trihydrofluoride) is added to a solution of compound B-3 (e.g., under nitrogen gas flow) at a suitable temperature (e.g., under ice-cooled condition), and the mixture is stirred at a suitable temperature (e.g., room temperature) for a suitable time (e.g., 12 hours). The reaction is quenched (e.g., by adding water to the reaction solution), and the reaction solution is extracted with a suitable organic solvent (e.g., ethyl acetate). The organic layer is washed (e.g., with saturated saline), and then dried with a suitable drying agent (e.g., anhydrous sodium sulfate). The solvent is distilled away under reduced pressure to obtain compound B-4.

(4) Synthesis of Compound B-5

$PG_5X$ (wherein $PG_5$ is a protecting group disclosed herein and X is Cl, Br, or I, such as dimethoxytrityl chloride) is added to a solution of compound B-4 (e.g., under nitrogen gas flow) at a suitable temperature (e.g., room temperature), and the mixture is stirred at a suitable temperature (e.g., room temperature) for a suitable time (e.g., 12 hours). The reaction is quenched (e.g., by adding water to the reaction solution), and the reaction solution is extracted with a suitable organic solvent (e.g., ethyl acetate). The organic layer is washed (e.g., with saturated saline), and then dried with a suitable drying agent (e.g., anhydrous sodium sulfate). The solvent is distilled away under reduced pressure to obtain compound B-5.

(5) Synthesis of Compound B-6

A suitable reagent (e.g., 2-cyanoethyl-N,N,N',N'-tetraisopropylphosphoamidite) is added to a solution of compound B-5 (e.g., under nitrogen gas flow) at a suitable temperature (e.g., room temperature), and the mixture is stirred at a suitable temperature (e.g., room temperature) for a suitable time (e.g., 4 hours) to modify a hydroxy group at position 3' with P(O) (OPG$_6$) (OPG$_7$) (PG$_6$ and PG$_7$ are each independently a protecting group disclosed herein). The reaction is quenched (e.g., by adding water to the reaction solution), and the reaction solution is extracted with a suitable organic solvent (e.g., ethyl acetate). The organic layer is washed (e.g., with saturated saline) and then dried with a suitable drying agent (e.g., with anhydrous sodium sulfate). The solvent is distilled away under reduced pressure to obtain compound B-6.

<2> Synthesis of Oligonucleotide Analog

Various oligonucleotide analogs including the nucleoside analog of the present invention can be synthesized using a known DNA synthesizer. The production of purified oligonucleotide analog can be then confirmed by purifying the resulting oligonucleotide analog using a reverse phase column and analyzing the purity of the product with reverse phase HPLC or MALDI-TOF-MS. One or more of the nucleoside analog of the present invention can be placed in an oligonucleotide analog. The nucleoside analog may also be present while being separated at two or more sites in the oligonucleotide analog with one or more naturally occurring nucleotides interposed therebetween. The present invention can synthesize an oligonucleotide analog having the nucleoside analog of the present invention introduced at a required position at a required number (length). The length of an entire oligonucleotide analog is 2 to 50, preferably 8 to 30 nucleotide units.

The oligonucleotide analog of the present invention is resistant to nuclease degradation, so that the analog can be in the body for a long period after administration thereto. In addition, the oligonucleotide analog of the present invention forms a double strand with a sense RNA to inhibit transcription of an in vivo component (protein), which is a pathological factor, into an mRNA. Such an analog is understood to inhibit the proliferation of infected viruses.

In view of the above, the oligonucleotide analog of the present invention is expected to be useful as a medicament for treating a disease by inhibiting the function of a gene, including antitumor agents and antiviral agents. In other words, the present invention provides an oligonucleotide analog and a manufacturing intermediate thereof, i.e., nucleoside analog, having stable and excellent antisense or antigene activity or excellent activity as a primer for starting amplification or a detection agent for a specific gene.

DNA or RNA oligonucleotide analogs (oligonucleotide analogs) prepared by modifying, in various forms, a 2',4'-BNA$^{NC}$ monomer that is one of the nucleoside analogs of the present invention are useful as materials for various physiological/bioactive substances or medicaments, functional materials of double-stranded oligonucleotides for RNA interference or decoy processes, functional materials for DNA chips or molecular beacons targeting a single-stranded nucleic acids such as cDNA, functional materials for various applications in antisense methods (including ribozymes and DNAzymes), antigene methods, and gene homologous recombination methods, materials for high sensitivity analysis of in vivo trace elements in combination with a fluorescent or light emitting substance, or materials for developing reagents used for research such as gene function analysis/elucidation.

The nucleoside analog or oligonucleotide analog of the present invention can be used, for example, as a topically administered formulation in combination with a conventionally used additive such as a buffer and/or a stabilizer. As a topical formulation, a conventionally used pharmaceutical carrier can be combined to prepare an ointment, cream, liquid agent, plaster, or the like.

(General Synthesis Example for Oligonucleotides Constituting S-TuD)

Oligonucleotides constituting the S-TuD used in the present invention are synthesized with a synthesizer (e.g., nS-8II synthesizer or AKTA oligopilot synthesizer). A controlled pore glass solid phase carrier (e.g., 2'-O-methyl-RNA CPG, Link Technologies), 2'-O-methyl-RNA phosphoramidite having a standard protecting group (examples thereof include, but are not limited to, 5'-O-dimethoxytrityl-N6-benzoyladenosine-2'-O-methyl-3'-O—N,N'-diisopropyl-phosphoramidite, 5'-O-dimethoxytrityl-N4-acetylcytidine-2'-O-methyl-3'-O—N,N'-diisopropylphosphoramidite, 5'-O-dimethoxytrityl-N2-isobutylguanosine-2'-O-methyl-3'-O—N,N'-diisopropylphosphoramidite, and 5'-O-dimethoxytrityluridine-2'-O-methyl-3'-O—N,N'-diisopropylphosphoramidite (which are manufactured by Sigma-Aldrich), and 2',4'-BNA$^{NC}$ (2'-O,4'-C-aminomethylene bridged nucleic acid) thymidine phosphoramidite, i.e., 2'-O,4'-C-aminomethylene-5'-O-dimethoxytrityl-thymidine-N,N'-diisopropylphosphoramidite, 2',4'-BNA$^{NC}$ adenosine phosphoramidite, i.e., 2'-O,4'-C-aminomethylene-5'-O-dimethoxytrityl-N6-benzoyladenosine-N,N'-diisopropylphosphoramidite (which are manufactured by BNA), and LNA (Locked nucleic acid) (2'-O,4'-C-methyleneribonucleic acid) thymidine phosphoramidite, i.e., 2'-O,4'-C-methylene-5'-O-dimethoxytritylthymidine-N,N'-diisopropylphosphoramidite (manufactured by Exiqon)) are used in oligonucleotide synthesis. All phosphoramidites are used in a suitable solvent (e.g., acetonitrile (CH$_3$CN)) at a suitable concentration (e.g., 0.1 M). For 2'-O-methylRNA, BNA and LNA, a suitable linking/reuse time (e.g., 15 minutes) is used. Examples of activating agents include, but are not limited to, 5-benzylmercapto-tetrazole (0.25 M, Wako Pure Chemical Industries). For example, PO-oxidation uses, but is not limited to, iodine/water/pyridine. For example, PS-thioation uses, but is not limited to, commercially available sulfuration reagents for automated oligonucleotide synthesizers (i.e., EIDTH, DDTT, PADS, Beucage reagents, and the like) with a suitable reagent (e.g., pyridine).

(General Example of Deprotection (General Example of Nucleobase Deprotection))

After the completion of synthesis, the synthesized carrier is transferred to a suitable container (e.g., glass bottle). Oligonucleotides are cleaved from the carrier by deprotecting a base and a phosphoric acid group at a suitable temperature (e.g., 45° C.) for a suitable time (e.g., hours) using 15 mL of a mixture of equal parts of aqueous 40% methylamine solution and 33% methylamine ethanol solution for 1 g of carrier. The step of deprotecting a base and the step of deprotecting a phosphoric acid group may be the same or different steps. An ethanol ammonium mixture is then filtered and placed in a suitable container (e.g., new 250 mL bottle). The carrier is washed (e.g., with 2×40 mL of ethanol/water (1:1 v/v)). The solvent is distilled away for exsiccation (e.g., using a rotary evaporator (roto-vap)).

(General Example for HPLC Purification)

Oligonucleotides are purified by HPLC (e.g., reverse phase ion pair HPLC with a Source 15 RPC gel column). Examples of buffer include, but are not limited to, 5% CH$_3$CN, 0.1 M triethylamine acetic acid buffer (pH 7.0) (buffer A) and 90% CH$_3$CN, 0.1 M triethylamine acetic acid buffer (pH 7.0) (buffer B). Fractions comprising a full-length oligonucleotide are pooled while retaining a protecting group (e.g., dimethoxytrityl group) at the 5' end and are subjected to the next purification. The oligonucleotide pool is then purified by HPLC (e.g., Source 30Q anion pair HPLC). Examples of solution and buffer are, but are not limited to, 0.6% trifluoroacetate (solution A), 20 mM sodium phosphate buffer (pH 7.5) (buffer C), and 2M sodium chloride (buffer D) in 20 mM sodium phosphate buffer. After having a protecting group at the 5' end leave, fractions comprising a full-length oligonucleotide are pooled, desalinated, and then lyophilized. The compound is ultimately analyzed, for example, with MALDI-TOF/MS and denaturing polyacrylamide gel.

(General Example of Double-Strand Formation)

After a purified single-stranded oligonucleotide is dissolved into a suitable solvent (e.g., distilled water), the oligonucleotide concentration is determined (e.g., by measuring absorbance using a UV spectrophotometer). Each complementary strand is mixed to be at an equimolar concentration by using the determined concentration and is heated at a suitable temperature (e.g., 95° C.) for a suitable time (e.g., 10 minutes) then gradually cooled to allow the formation of a double strand. Double-strand formation is confirmed by, for example, non-denaturing gel electrophoresis.

A nucleic acid may also comprise a conjugant. Examples of a conjugant include lipophilic substances, terpene, protein binding substances, vitamins, carbohydrates, retinoids, peptides, and the like.

(Other Special Forms of Single Strand of RNA)

The miRNA inhibiting complex of the present invention can be designed to comprise a straight single-stranded nucleic acid (FIG. 31). The present invention relates especially to a complex in which all MBSes are aggregated to one side (right side in FIG. 31) of a double-stranded structure (stem I in FIG. 31), while each strand of the double-stranded structure is structured to be closed on that side (i.e., linked by a sequence comprising an MBS), and both ends of a single-stranded RNA are on the opposite side of the double-stranded structure (FIG. 31). A sequence comprising an MBS may comprise an additional double-stranded structure (stem II, III, or the like in FIG. 31). The length of a single-stranded RNA may be appropriately determined. Examples thereof include 500 bases or less, preferably 450 bases or less, 420 bases or less, 400 bases or less, 380 bases or less, 360 bases or less, 340 bases or less, 320 bases or less, 300 bases or less, 280 bases or less, 260 bases or less, 240 bases or less, 220 bases or less, 200 bases or less, 180 bases or less, 160 bases or less, 140 bases or less, 120 bases or less, 100 bases or less, or 80 bases or less. Examples of the length of a single-stranded RNA forming a complex with two MBSes and two double-stranded structures include 60 to 300 bases, preferably 70 to 250 bases, 80 to 200 bases, 90 to 180 bases, or 100 to 150 bases. A first double-stranded structure (double-stranded structure close to both ends of a single-stranded RNA) can be, for example, 15 to 30 bp, preferably 16 to 28 bp, preferably 17 to 25 bp, preferably 17 to 24 bp, such as 17 bp, 18 bp, 19 bp, 20 bp, 21 bp, 22 bp, 23 bp, or 24 bp. A second double-stranded structure (additional double-stranded structure comprised in a sequence comprising an MBS) may be shorter than the first double-stranded structure in order to maintain the compact size of the whole complex. Examples of the length thereof include 4 bp to 20 bp, such as 5 bp to 15 bp, 5 bp to 12 bp, 5 bp to 10 bp, 6 bp to 9 bp, and 7 bp to 8 bp.

The present invention also relates to an RNA constituting the miRNA inhibiting complex of the present invention (wherein the RNA includes naturally-occurring RNAs and nucleic acid analogs), comprising a BNA. The complex of the present invention can be constructed by intramolecular annealing of RNA when an miRNA inhibiting RNA complex is comprised of one molecule of RNA, or by annealing RNAs when it is comprised of two or more RNA molecules. These RNAs can be appropriately synthesized. For example, a desired RNA can be manufactured by chemical synthesis of RNA.

A nucleic acid encoding at least one MBS may comprise two or more MBSes. A pair or a set of more complementary sequences that can form a double-stranded structure may be comprised in a contiguous sequence. Examples of such nucleic acids include nucleic acids comprising at least one MBS on each of both ends of a pair of complementary sequences and the pair of complementary sequences forming at least one double-stranded structure. Such a nucleic acid is specifically a nucleic acid comprising a pair of complementary sequences that can form a stem between two MBSes. The stem corresponds to the aforementioned second double-stranded structure. Alternatively, a sequence forming a G-quadruplex instead of a second double-stranded structure may be comprised.

Said nucleic acid may comprise two or more structural units comprising a pair of complementary sequences that can form a double-stranded structure between two MBSes. Multiple such structural units can be comprised in a nested form. Between a pair of complementary sequences that can form a double-stranded structure between a pair of MBSes, there can be a sequence comprising an additional pair of MBSes and a pair of complementary sequences that can form a double-stranded structure therebetween (#15 or #16 in FIG. 31 or the like). The sequences of MBSes may be the same or different.

Insertion of such a nucleic acid between the aforementioned pair of complementary sequences results in a nucleic acid with a structure, to which a sequence with a structure of MBS-sequence forming a second double-stranded structure-MBS is inserted between a pair of complementary sequences that form a first double-stranded structure. A specific example thereof is a nucleic acid with a structure to which a sequence with a structure of MBS-pair of complementary sequences forming a second double-stranded structure-MBS is inserted. A nucleic acid consisting of two double-stranded structures and a pair of opposing single strands (each comprising an MBS) therebetween is compact and exhibits sufficient miRNA inhibiting activity.

A pair of complementary sequences that can form a double-stranded structure and MBSes can be linked via an appropriate linker or a spacer. The length of a linker or a spacer is disclosed herein. Further, a complementary sequence may be linked via a linker or a spacer. When a double strand is formed, the linker or spacer forms a loop, thus forming a stem loop with the double strand. The length of a loop may be appropriately adjusted. The details thereof are disclosed herein. Alternatively, a sequence forming a G-quadruplex can be appropriately used instead of a double strand.

PREFERRED EMBODIMENTS

The preferred embodiments of the present invention are explained hereinafter. It is understood that the embodiments provided hereinafter are provided to better facilitate the understanding of the present invention, so that the scope of the present invention should not be limited by the following description. Thus, it is apparent that those skilled in the art can refer to the descriptions herein to appropriately make modifications within the scope of the present invention. It is also understood that the following embodiments of the present invention can be used individually or as a combination.

In one aspect, the present invention provides an miRNA inhibiting complex comprising an RNA or an analog thereof, the miRNA inhibiting complex comprising at least one double-stranded structure and an miRNA binding sequence, wherein two strands of the miRNA binding sequence are each bound to one of the two strands on at least one end of the double-stranded structure, and wherein the miRNA inhibiting complex comprises at least one bridged nucleic acid (BNA). Such a complex is also called S-TuD. The present invention is a further improvement thereof, such that the present invention is also called an improved S-TuD or modified S-TuD. Such an improved S-TuD (miRNA inhibiting complex) comprises at least one bridged nucleic acid (BNA). It is understood that the miRNA inhibiting complex of the present invention improved stability, suppressed the generation of impurities in the purification process, and surprisingly had elevated biological activity by including such a BNA, so that the complex is used as an ideal raw material for nucleic acid medicament or as a medicament itself.

In one preferred embodiment, the BNA comprises a BNA that is bridged via at least one atom selected from the group consisting of oxygen and carbon on the position 2' side and via at least one atom selected from the group consisting of carbon and nitrogen and carbon on the position 4' side. Although not wishing to be bound by any theory, an oligonucleotide can be readily synthesized and RNA doublestrand formation is promoted, so that this is used as a preferred BNA.

In a preferred embodiment, the BNA used in the present invention comprises a 2',4' substituted bridged nucleic acid represented by

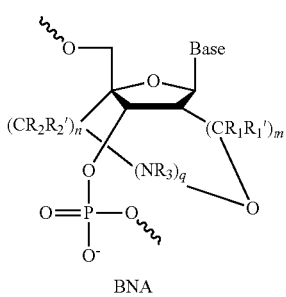

BNA wherein $R_1$, $R_1'$, $R_2$, $R_2'$, and $R_3$ each independently represent a group selected from the group consisting of a hydrogen atom, an alkyl group, an alkenyl group, a cycloalkyl group, an aryl group, an aralkyl group, an acyl group, a sulfonyl group, a silyl group, and a functional molecule unit substituent, m is an integer from 0 to 2, Base represents an adeninyl group, a thyminyl group, a uracilyl group, an inosinyl group, a cytosinyl group, a guaninyl group, a methylcytosinyl group, or a derivative thereof, n is an integer from 1 to 3, and q is an integer that is 0 or 1.

In a preferred embodiment, the BNA used in the present invention comprises a 2',4' substituted bridged nucleic acid represented by

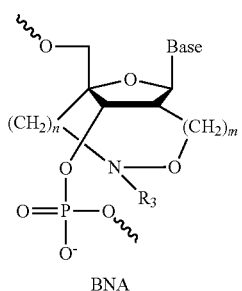

BNA wherein $R_3$ represents a group selected from the group consisting of a hydrogen atom, an alkyl group, an alkenyl group, a cycloalkyl group, an aryl group, an aralkyl group, an acyl group, a sulfonyl group, a silyl group, and a functional molecule unit substituent, Base represents an adeninyl group, a thyminyl group, a uracilyl group, an inosinyl group, a cytosinyl group, a guaninyl group, a methylcytosinyl group, or a derivative thereof, m is an integer from 0 to 2, and n is an integer from 1 to 3.

More preferably, the BNA used in the present invention comprises

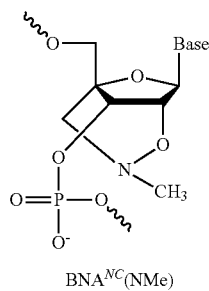

$BNA^{NC}(NMe)$ or a 2',4'-methano bridged nucleic acid (LNA).

$BNA^{NC}(NMe)$ is especially preferable. Although not wishing to be bound by any theory, this is because the use of this specific nucleic acid increased stability and promoted double-strand formation, and the improvement in biological activity was observed.

In another embodiment, cEt can be used.

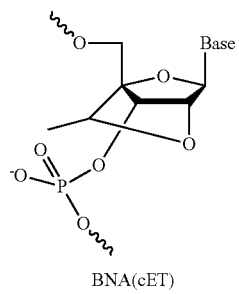

BNA(cET)

Although not wishing to be bound by any theory, this is because BNA(cEt) has thermal stability and mismatch identification that are similar to conventional LNAs, but has improved stability against nuclease.

In one embodiment, the BNA used in the present invention is comprised in at least one of the strands of the double-stranded structure moiety and at least one strand of complementary strands of the miRNA binding sequence.

In another embodiment, the BNA used in the present invention is comprised in at least one of the strands of the double-stranded structure moiety. In another embodiment, the BNA used in the present invention is comprised in both strands of the double-stranded structural moiety.

In one embodiment, the complex of the present invention can comprise one or more "double-stranded structures", and may have the same S-TuD structure as Patent Literature 1 or the Examples. For example, three or four double-stranded structures can be contiguously comprised in series. It is understood that such an embodiment is also encompassed by the present invention.

In one embodiment, the complex of the present invention comprises two or more of the double-stranded structures, wherein strands comprising the miRNA binding sequence are each bound to one of the two strands on one end of a first double-stranded structure of the double-stranded structures, and the other ends of the strands are each bound to one of two strands of a second double-stranded structure of the two or more of the double-stranded structures, so that the strands are sandwiched between the two or more of the double-stranded structures. Preferably, the complex of the present invention comprises a second multi-stranded structure selected from double and quadruple stranded structures, wherein ends of two strands comprising the miRNA binding sequence are each bound to one of two strands on one end of the double-stranded structure via a 1 to 5 base linker, and the other ends of the two strands comprising the miRNA binding sequence are each bound to one of two strands on one end of the second multi-stranded structure via a 1 to 5 base linker, so that the strands are sandwiched by the double-stranded structure and the second multi-stranded structure, but the complex is not limited thereto. Alternatively, it can be advantageous for each of the two strands comprising the miRNA binding sequence comprised in the complex of the present invention to comprise an miRNA binding sequence, while there are two strands comprising an miRNA binding sequence, but the present invention is not limited thereto.

In another embodiment, an end of two strands comprising the miRNA binding sequence is bound via a linker in the present invention. In a preferred embodiment, a length of the linker is 1 to 10 bases long, more preferably 1 to 9 bases long, still more preferably 1 to 8 bases long, still more preferably 1 to 7 bases long, still more preferably 1 to 5 bases long, and may be 4 bases long, 3 bases long, 2 bases long, or 1 base long.

The length of a double-stranded structure in the miRNA inhibiting complex of the present invention may be of any length as disclosed above, but is preferably 4 base pairs or greater. In particular, at least one of the double-stranded structures comprised in the RNA complex of the present invention (i.e., first double-stranded structure) has an important function for nuclear export of RNA complexes. The length of the double strand may be, for example, 10 to 50 or 15 to 50 base pairs, preferably 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 bases, or any of them or greater, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, or 18 bases, or any one of them or less. In a preferred embodiment, the length of a base pair of a double-stranded structure is for example 10 to 30, 15 to 30, preferably 16 to 28, preferably 17 to 25, preferably 17 to 24, such as 17, 18, 19, 20, 21, 22, 23, or 24. High activity is exhibited at over 20 bp, but dsRNA greater than 20 bp can be a potential target of cleavage by Dicer in the cytoplasm. In order to avoid this, the double-stranded structure comprised in the complex of the present invention can be structured to be 20 bp or less, such as 19 bp or less or 18 bp or less. A double-stranded structure comprised in an miRNA inhibiting complex is further disclosed in the following preferred embodiments. For example, said double-stranded structure may be 5 bp to 15 bp, 5 bp to 12 bp, 5 bp to 10 bp, 6 bp to 9 bp, 7 bp to 8 bp, or 10 bp to 12 bp.

The lower limit length of a double-stranded structure in the complex of the present invention is not particularly limited as long as the activity is retained, but the length may be at least 4 bases long, at least 5 bases long, at least 6 bases long, at least 7 bases long, at least 8 bases long, preferably at least 9 bases long, and still more preferably at least 10 bases long. When there are two or more double strands, the base length thereof may be the same or different. While sufficient double-strand formation is confirmed and sufficient effect is demonstrated at 10 bases long, the length may optionally be, for example, at least 11 bases long, at least 12 bases long, at least 13 bases long, at least 14 bases long, at least 15 bases long, at least 16 bases long, at least 17 bases long, or at least 18 bases long.

The upper limit length of a double-stranded structure in the complex of the present invention is not particularly limited as long as the activity is retained, but the length can be, for example, 100 bases long or less, 90 bases long or less, 80 bases long or less, 70 bases long or less, 60 bases long or less, 50 bases long or less, or the like.

When the miRNA inhibiting complex of the present invention comprises a second or greater double-stranded structure, the sequence and length of the double-stranded structures are not particularly limited. For example, the double-stranded structures may be shorter than the length of a first double-stranded structure in order to maintain the compactness of the entire miRNA inhibiting complex. The length of each double strand may be appropriately adjusted, but may be, for example, 4 bp to 20 bp, such as 5 bp to 15 bp, 5 bp to 12 bp, 5 bp to 10 bp, 6 bp to 9 bp, or 7 bp to 8 bp.

The present invention is expected to exert its effect if there is one BNA, but preferably comprises 2 or more, 3 or more, 4 or more, 5 or more, 6 or more, 7 or more, 8 or more, 9 or more, or 10 or more BNAs. However, a sufficient effect is achieved with about 6 BNAs so that the effect is not increased by including more BNAs in some cases. Thus, inclusion of around 6 BNAs (e.g., 4 to 8, 4 to 6, or the like) can be sufficient.

Further, it was found that the complex of the present invention has stronger activity (action at low concentration) than conventional complexes. Examples of the effect that can be achieved by the complex of the present invention include, but are not limited to, about 2-fold or greater, about 3-fold or greater, about 4-fold or greater, about 5-fold or greater, about 6-fold or greater, about 7-fold or greater, about 8-fold or greater, about 9-fold or greater, about 10-fold or greater, about 15-fold or greater, about 20-fold or greater, about 25-fold or greater, about 30-fold or greater, about 40-fold or greater, about 50-fold or greater, about 75-fold or greater, and about 100-fold or greater relative to the effect of conventional complexes. Thus, the complex of the present invention achieves a significant effect of acting at 10 nM or less, 5 nM or less, 3 nM or less, 1 nM or less, 500 pM or less, 300 pM or less, 100 pM or less, 50 pM or less, 30 pM or less, 10 pM or less, 5 pM or less, 3 pM or less, or 1 pM or less.

In another embodiment, the complex of the present invention comprises 2 to 5 and preferably 2 miRNA binding sequences.

The complex of the present invention comprises the structure represented by

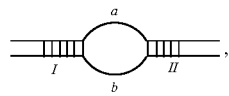

(C)

wherein I and II of the structure are double-stranded structures, and each of a and b of the structure can have a structure comprising an miRNA binding sequence.

In another embodiment, the present invention provides each RNA constituting the complex of the present invention or an analog thereof (e.g., each single strand). Each of these RNAs or an analog thereof is within the scope of the present invention. A preferred embodiment for a single strand is substantially the same as in a double-stranded structure, so that the same preferred embodiments can be employed.

In another aspect, the present invention provides a method of manufacturing the complex of the present invention, comprising:
A) synthesizing a protected entity of a single strand of an RNA of interest or an analog thereof and a protected entity of a complement thereof by chemical synthesis using a ribonucleic acid and a BNA; B) deprotecting each of the protected entity of the single strand and the complement thereof, which have been generated; C) placing each of the single strands that has been deprotected under a double-strand forming condition to form a double strand.

In still another embodiment, the present invention provides a method of manufacturing the RNA of the present invention or an analog thereof, comprising: A) synthesizing a protected entity of a single strand of an RNA of interest or an analog thereof and a protected entity of a complement thereof by chemical synthesis using a ribonucleic acid and a BNA; and B) deprotecting each of the protected entity of the single strand and the complement thereof, which have been generated.

Such a method has been disclosed herein in detail in other sections. Examples also describe a demonstrative example. It is understood that those skilled in the art can manufacture various complexes, RNAs or analogs thereof by referring to such descriptions.

(Medicament and Therapeutic/Prophylactic Method)

In another aspect, the present invention provides a medicament comprising the complex of the present invention.

In one embodiment, the miRNA inhibiting complex of the present invention or RNA constituting complex (where RNA includes naturally-occurring RNAs and analogs) can be prepared into a composition for inhibiting an miRNA. The composition of the present invention can specifically and effectively inhibit a target miRNA, so that the composition is useful in controlling the function of a gene via inhibition of an miRNA. The composition of the present invention can be combined with a desirable pharmacologically acceptable carrier or medium as needed. Examples thereof include desired solutions that are generally used in suspension of a nucleic acid, such as distilled water, phosphate-buffered saline (PBS), sodium chloride solution, Ringer's solution, and culture solution. Vegetable oil, suspension, surfactant, stabilizer, biocide or the like may also be comprised. A preservative or another additive may also be added. The composition of the present invention can also combine an organic matter such as a biopolymer, inorganic matter such as hydroxyapatite, specifically, a collagen matrix, polylactic acid polymer or copolymer, polyethylene glycol polymer or copolymer, a chemical derivative thereof or the like as a carrier. The composition of the present invention can be used as a desired reagent or a pharmaceutical composition. The present invention also provides use of the composition of the present invention, miRNA inhibiting complex of the present invention, or RNA constituting the complex or an analog thereof for inhibiting an miRNA. The present invention also provides an miRNA inhibitor comprising any one of the above.

In still another aspect, the present invention provides a method of treating or preventing a disease or a disorder, comprising administering an effective amount of the complex of the present invention or a medicament comprising the same to a subject in need thereof. The present invention can be applied in, for example, but not limited to, use as a therapeutic agent for HCV or renal fibrosis, whose clinical development is already in progress.

The medicament of the present invention may be administered by itself or as a suitable pharmaceutical composition. A pharmaceutical composition used in administration may comprise the medicament of the present invention and a pharmaceutically acceptable carrier, diluent, or excipient. Such a pharmaceutical composition is provided as a dosage form that is suitable for oral or parenteral administration.

A composition for parenteral administration may be used as, for example, an injection, suppository, or the like, and injections may encompass dosage forms such as intravenous injection, subcutaneous injection, intracutaneous injection, muscular injection, and intravenous drip injection. Such injections can be prepared in accordance with known methods. Examples of preparation methods of an injection include preparation by dissolving, suspending, or emulsifying the aforementioned nucleic acid of the present invention in an aseptic aqueous solution or oily solution that is generally used in injections. Examples of aqueous solutions for injection that are used include saline, isotonic solution comprising glucose or other adjuvants and the like, which may be concomitantly used with a suitable solubilizer, such as alcohol (e.g., ethanol), polyalcohol (e.g., propylene glycol or polyethylene glycol), anionic surfactant [e.g., polysorbate 80, HCO-50 (polyoxyethylene (50 mol) adduct of hydrogenated castor oil)] or the like. For example, sesame oil, soybean oil or the like is used as an oily solution, which may be used concomitantly with benzyl benzoate, benzyl alcohol, or the like as a solubilizing agent. A prepared injection is preferably filled in a suitable ampule. Suppositories used in rectal administration may be prepared by mixing the aforementioned nucleic acid with a common base agent for suppositories.

Examples of compositions for oral administration include solid or liquid dosage forms, specifically tablets (including sugar-coated tablets and film-coated tablets), pills, granules, powder, capsules (including soft capsules), syrup, emulsion, suspension and the like. Such a composition is manufactured by a known method and may contain a carrier, diluent, or excipient that is commonly used in the drug development field. Examples of carriers and excipients for tablets that are used include lactose, starch, sucrose, and magnesium stearate.

The aforementioned parenteral or oral pharmaceutical composition is suitably prepared in a dosage form in a dosing unit that would match the dosage of an active ingredient. Examples of such a dosage form of a dosing unit include tablets, pills, capsules, injections (ampule) and suppositories.

The medicament of the present invention has low toxicity, which can be orally or parenterally (e.g., intravascular administration, subcutaneous administration or the like) to humans or mammals (e.g., rats, rabbits, sheep, pigs, cows, cats, dogs, monkeys, or the like) directly as a liquid agent or as a pharmaceutical composition in a suitable dosage form.

The medicament can be introduced into cells in vitro, ex vivo, or in vivo. When administered via cells, it is introduced to cells collected from suitable cultured cells or animal subjected to inoculation. Examples of introduction of nucleic acids include calcium phosphate coprecipitation, lipofection, DEAE dextran method, a method of direct injection of DNA solution by an injection needle or the like, introduction by a gene gun, and the like. The dosage varies depending on the disease, patient weight, age, sex, symptom, objective of administration, form of administered composition, administration method, introduced gene or the like. The dosage may be appropriately adjusted in accordance with the animal subjected to administration, administered site, number of administrations, or the like. Those skilled in the art would have appropriately determined the dosage. The route of administration can be appropriately selected. The subject of administration is preferably a mammal (including humans and non-human mammals). Specifically, the subject includes humans, non-human primates such as monkeys, rodents such as mice and rats, rabbits, goats, sheep, pigs, cows, dogs, cats, and other mammals.

As used herein, "or" is used when "at least one or more" of the listed matters in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

The present invention has been described while showing preferred embodiments to facilitate understanding. The present invention is described hereinafter based on Examples.

The aforementioned description and the following Examples are not provided to limit the present invention, but for the sole purpose of exemplification. Thus, the scope of the present invention is not limited to the embodiments and Examples that are specifically described herein and is limited only by the scope of claims. It should be noted that the documents cited herein are all incorporated as a part of the present specification.

EXAMPLES

The nucleoside analogs and oligonucleotide analogs of the present invention were synthesized in accordance with the following synthesis schemes. The synthesis is explained in further detail in the Examples. The characteristics of the synthesized oligonucleotide analogs were measured in Experimental Examples. In the Examples, Long Type refers to those in which the left side of STEM is 18 bp and the right side is 10 bp as in the original S-TuD (SEQ ID NOs: 1 to 2), and Short type refers to those in which the left side of STEM is 10 bp and the right side is 10 bp, unless specifically noted otherwise.

Manufacturing Example (Synthesis of Oligonucleotides)

Oligonucleotides were synthesized using an nS-8II synthesizer or AKTA oligopilot synthesizer. A commercially available controlled pore glass solid phase carrier (e.g., 2'-O-methyl-RNA CPG Link Technologies), 2'-O-methyl-RNA phosphoramidite having a standard protecting group, i.e., 5'-O-dimethoxytrityl-N6-benzoyladenosine-2'-O-methyl-3'-O—N,N'-diisopropylphosphoramidite, 5'-O-dimethoxytrityl-N4-acetylcytidine-2'-O-methyl-3'-O—N,N'-diisopropylphosphoramidite, 5'-O-dimethoxytrityl-N2-isobutylguanosine-2'-O-methyl-3'-O—N,N'-diisopropylphosphoramidite, and 5'-O-dimethoxytrityluridine-2'-O-methyl-3'-O—N,N'-diisopropylphosphoramidite (which are manufactured by Sigma-Aldrich), and 2',4'-BNA$^{NC}$ (2'-O,4'-C-aminomethylene bridged nucleic acid) thymidine phosphoramidite, i.e., 2'-O,4'-C-aminomethylene-5'-O-dimethoxytrityl-thymidine-N,N'-diisopropylphosphoramidite, 2',4'-BNA$^{NC}$ adenosine phosphoramidite, i.e., 2'-O,4'-C-aminomethylene-5'-O-dimethoxytrityl-N6-benzoyladenosine-N,N'-diisopropylphosphoramidite (which are manufactured by BNA), and LNA (Locked nucleic acid) (2'-O,4'-C-methyleneribonucleic acid) thymidine phosphoramidite, i.e., 2'-O,4'-C-methylene-5'-O-dimethoxytritylthymidine-N, N'-diisopropylphosphoramidite (manufactured by Exiqon)) were used in oligonucleotide synthesis. All phosphoramidites were used in acetonitrile ($CH_3CN$) at a concentration of 0.1 M. For 2'-O-methyl RNA, BNA and LNA, linking/reuse time of minutes was used. The activating agent was 5-benzylmercapto-tetrazole (0.25 M, Wako Pure Chemical Industries), and PO-oxidation used iodine/water/pyridine. Ps-thioation used commercially available sulfuration reagents for automated oligonucleotide synthesizers (i.e., EIDTH, DDTT, PADS, Beucage reagents, and the like) with pyridine.

Deprotection I (Nucleobase Deprotection)

After the completion of synthesis, the synthesized carrier was transferred to a glass bottle. Oligonucleotides were cleaved from the carrier by simultaneously deprotecting a base and a phosphoric acid group at 45° C. for 13 hours using 15 mL of a mixture of equal parts aqueous 40% methylamine solution and 33% methylamine ethanol solution for 1 g of carrier. An ethanol ammonium mixture was then filtered and placed in a new 250 mL bottle. The carrier was washed with 2×40 mL of ethanol/water (1:1 v/v). The solvent was then distilled away for exsiccation with a rotary evaporator (roto-vap).

(HPLC Purification)

Oligonucleotides were purified by reverse phase ion pair HPLC with a Source 15 RPC gel column. The buffer was 5% $CH_3CN$, 0.1 M triethylamine acetic acid buffer (pH 7.0) (buffer A) and 90% $CH_3CN$, 0.1 M triethylamine acetic acid buffer (pH 7.0) (buffer B). Fractions comprising a full-length oligonucleotide were pooled while retaining a dimethoxytrityl group at the 5' end, and were subjected to the next purification. The oligonucleotide pool was then purified by Source 30Q anion pair HPLC. The solution and buffer were 0.6% trifluoroacetate (solution A), 20 mM sodium phosphate buffer (pH 7.5) (buffer C), and 2 M sodium chloride (buffer D) in 20 mM sodium phosphate buffer. After having a dimethoxytrityl group leave using solution A, fractions comprising a full-length oligonucleotide were pooled, desalinated, and then lyophilized. The compound was ultimately analyzed with MALDI-TOF/MS and denaturing polyacrylamide gel.

(Double-Strand Formation)

After a purified single-stranded oligonucleotide was dissolved into distilled water, the oligonucleotide concentration, was determined by measuring absorbance using a UV spectrophotometer. Each complementary strand was mixed to be at an equimolar concentration by using the determined concentration and was heated at 95° C. for 10 minutes then gradually cooled to allow the formation of a double strand. Double-strand formation was confirmed by non-denaturing gel electrophoresis.

(Preparation and Culture of HeLaS3-miR199a Cells)

HeLaS3 cells were cultured at 37° C. in DMEM comprising 10% fetal bovine serum (FBS). HeLaS3 cells were seeded on a six well plate at $1 \times 10^5$ cells per well. After 24 hours, a pLSP-miR199a viral vector ($<1 \times 10^4$ TU) was introduced in the presence of 8 μg/ml of Polybrene. After 24 hours from transduction, the cells were selected using Puromycin (1 ug/ml). After 1 week of selection, Puromycin was removed from the medium to obtain HeLaS3-miR199a cells as HeLaS3 cells retaining a miR-199a reporter.

(Luciferase Assay)

Each of HeLaS3-miR199a cells and HCT-116 cells were seeded on a 24 well plate the day before introduction at $1.0 \times 10^5$ cells per well in DMEM comprising 10% fetal bovine serum (FBS). The cells were transfected in triplicate using Lipofectamine 2000 (Life Technologies) and 100 ng reporter plasmid (psiCHECK™-2, psiCHECK2-T199a-3px3, psiCHECK2-T200c-3p, or psiCHECK2-T21-5p) (see FIGS. 16 and 17) and various S-TuDs. All assays were conducted using GLOMAX™ (Promega) with dual luciferase assay (Promega) after 48 hours from transfection.

Example 1: Structure Strengthening Test

Figure 1A:
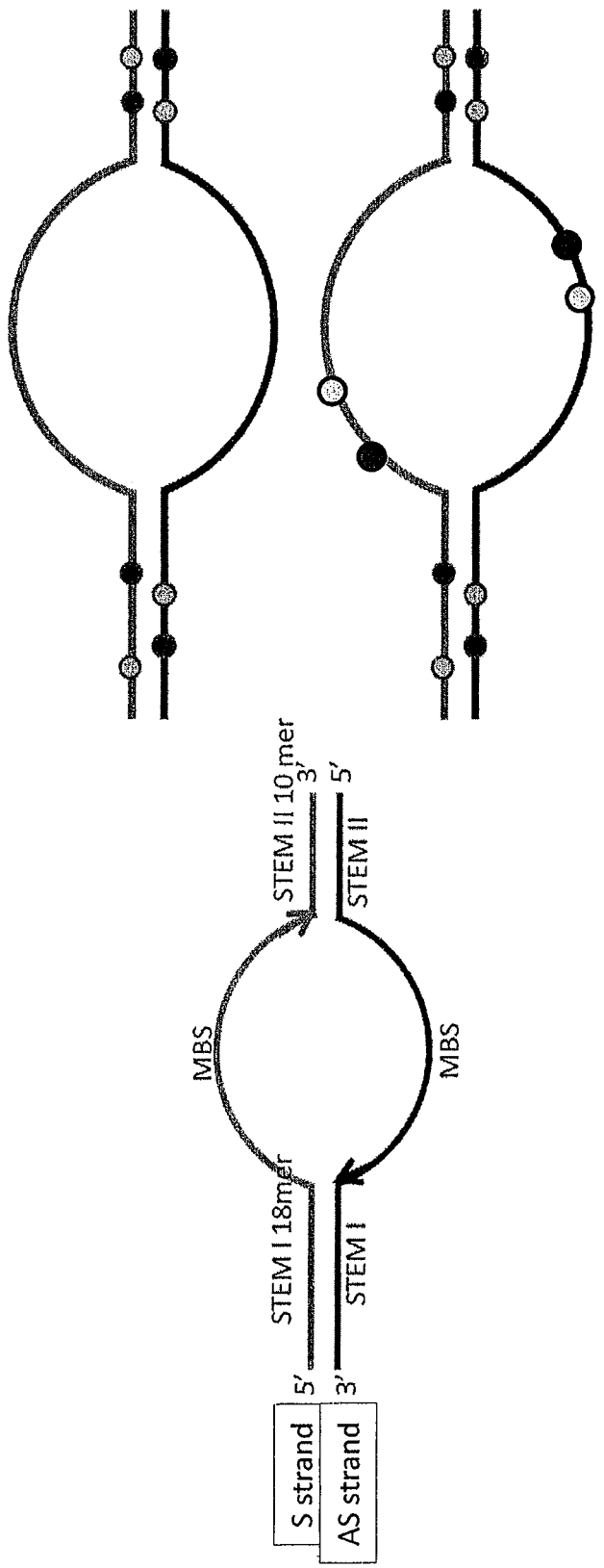
FIG. 1A shows a schematic diagram of a conventional S-TuD and a partially substituted S-TuD of the present invention.

The miRNA inhibitor developed by the inventors (synthetic Tough Decoy, S-TuD) has drawn attention as a nucleic acid that inhibits miRNA activity at a low concentration. Meanwhile, the physical properties after double-strand formation are not stable in view of the structural characteristic thereof. In this regard, the present Example used a partially substituted double strand in which a double-strand region was substituted with a modified nucleic acid that improves the hybridization capacity as a method of strengthening the double-strand and compared the miRNA inhibiting activity with a conventional S-TuD to facilitate the establishment of the methods of stable mass production and physical property tests (FIG. 1A).

Results of reverse phase HPLC analysis with a conventional S-TuD are shown in FIG. 13. FIG. 13 shows a comparison of an S strand, AS strand, and double strand analyzed by reverse phase HPLC (RP-HPLC) analysis (C18 reverse phase ion paring HPLC with XBridge column) of a conventional S-TuD.

The present Example used the following modified nucleic acids.

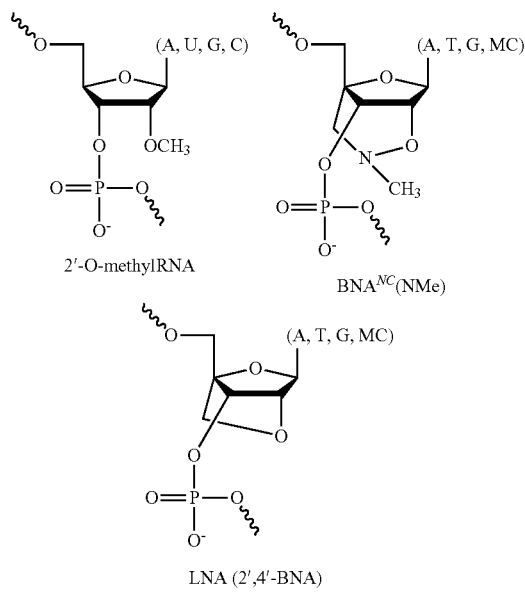

2'-O-methylRNA was used in the base structure of S-TuDs, and $BNA^{NC}(NMe)$ was used as a modified nucleic acid. LNAs can also similarly be used.

(Experiment for Improvement of Physical Properties)

Some of the bases in the STEM region was changed with a type of nucleotide species that elevates the double-strand formation capability ($BNA^{NC}(NMe)$) and physical properties were evaluated. The results are shown in FIG. 38. As a result, peak A in FIG. 1B decreased, and the precision of the reverse phase HPLC purity analysis of a double-strand improved.

The protocol of the reverse phase HPLC purity analysis is as follows. XBridge C18 2.5 μm, 4.6 nn x 75 mm was used as the column for HPLC analysis. For the eluent, 5% acetonitrile/0.1 M triethyl amine-acetic acid buffer (pH 7) was used as A and 90% acetonitrile/0.1 M triethyl amine-acetic acid buffer (pH 7) was used as B. The column temperature during analysis was 20° C., and the flow rate was 1 mL/min. The eluent concentration was gradually changed over 30 minutes from A:B=100:0 to A:B=75:25. Detection was confirmed by absorbance of UV (260 nm).

The structures of oligonucleotides that were used are shown in FIGS. 2A and 2B. Synthesis is the same as the one which synthesized oligonucleotides disclosed above. (1) C,U: 2'-F-C, 2'-F-U, (2) T: BNA-T, (3) T: BNA-T, (4) T: BNA-T A: BNA-T A, and (5) T: BNA-T A: BNA-A (10 bases) were used. The sequences shown in FIG. 2B are the following: (1)' S-TuD199a-3p-1_18-pf-S10; (1)" S-TuD199a-3p-1_18-pf-S10-BT4; (2)" S-TuD199a-3p-1_18-pf-S8-BT6; (3)" S-TuD199a-3p-1_18-pf-S8-BT4; (4)" S-TuD199a-3p-1_18-pf-S6-BT6; and (5)" S-TuD199a-3p-1_18-pf-S6-BT4.

Shortening the STEM I region to 10 bp results in some of the strands remaining as a single strand, as shown in FIGS. 39-1, 39-2 and 40, only for 2'-O-methyl forms that are similar to the original S-TuD, while the double-strand formation capability improved when substituted with BNA.

Double-strand formation was observed as shown in FIGS. 39-1, 39-2 and 40 upon $BNA^{NC}(NMe)$ conversion, even if the STEM I region or both STEM regions were shortened to 8 bp.

The effect of such an improvement in physical properties on activity was confirmed by an in vitro miR-199a inhibition assay.

The protocol of the miR-199a inhibition assay is the following.

The activity of a target miRNA was measured by measuring the ratio of renilla luciferase (RL) and firefly luciferase (FL) in the following Experiments 1 and 2.

Experiment 1

HeLaS3 cells that only slightly express miR199a 3p and 5p endogenously (Landgraf, P. et al. (2007) Cell, 129, 1401-1414) were cultured at 37° C. in DMEM comprising 10% fetal bovine serum (FBS). HeLaS3 cells were seeded in a six well plate at $1 \times 10^5$ cells per well. After 24 hours, a pLSP-miR199a viral vector ($<1 \times 10^4$ TU) was introduced in the presence of 8 μg/ml of Polybrene. After 24 hours from transduction, the cells were selected using Puromycin (1 ug/ml). After 1 week of selection, Puromycin was removed from the medium to obtain HeLaS3-miR199a cells as HeLaS3 cells retaining a miR-199a reporter.

Experiment 2

Figure 3:
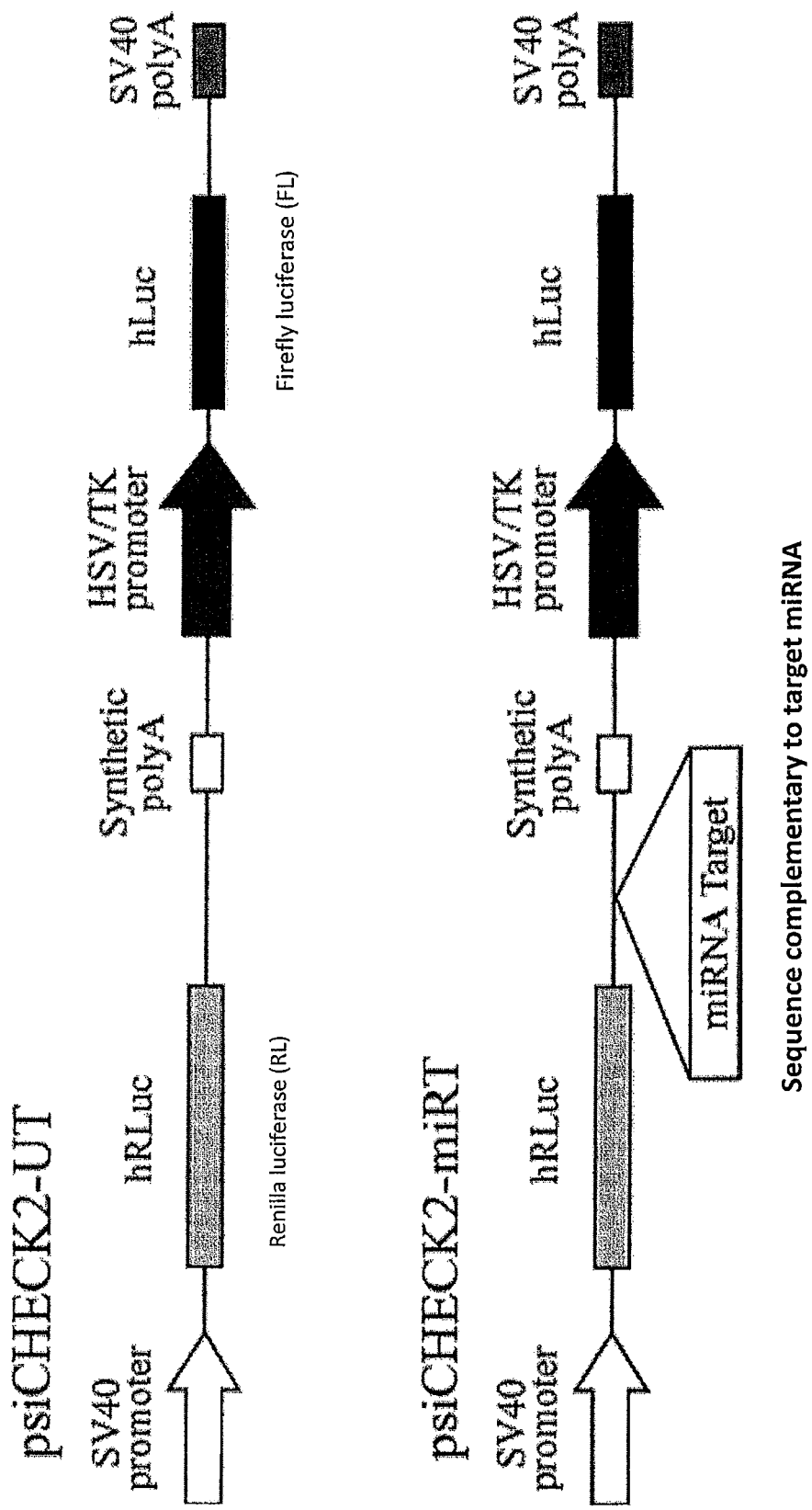
FIG. 3 shows the structures of psiCHECK2-UT (top) and psiCHECK2-miRT (bottom).

Cells (HeLaS3-miR199a) were transfected with psi-CHECK2-miRT (PROMEGA, prepared by inserting, for example, a sequence complementary to a target miRNA such as miR-199a-3p in the XhoI-NotI site; the entire structure is shown in FIG. 3) and a synthetic modified S-TuD as shown in FIG. 2.

Chemiluminescent signals generated by renilla luciferase (RL) and firefly luciferase (FL) expressed by transfected cells reacting with their respective specific substrate were then measured by a luminometer, and the ratio of renilla luciferase (RL) to firefly luciferase (FL) was obtained for the measured signals. The results are shown in FIGS. 4-1, 4-2, and 5. It is understood from the results in FIGS. 4-1 and 4-2 that if T is sufficiently substituted, substitution of BNA for only T is sufficient, in view of the effects of molecules (2)-(4). It appears that insertion of $BNA^{NC}(NMe)$ can shorten the length of Stem I, but the activity slightly decreases. In order to make it shorter, it is conjectured that it is necessary to increase the amount of BNA, such as $BNA^{NC}(NMe)$.

Figure 5:
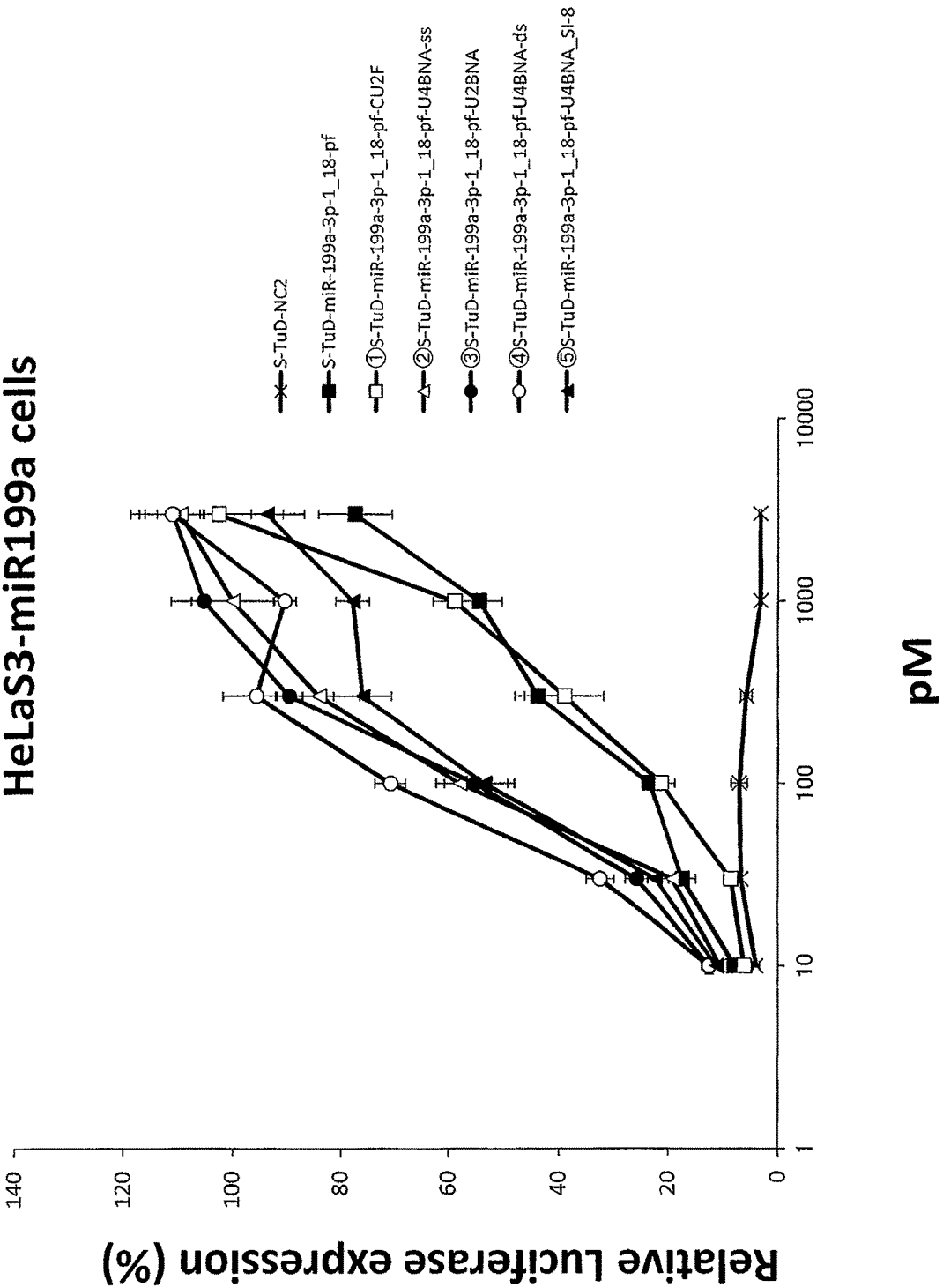
FIG. 5 shows the concentration dependency of various modified S-TuD199a-3p. HeLaS3-miR199a cells were used.

Next, data was prepared by normalizing the miR-199a reporter value in Experiment 2 with a value of the control reporter in Experiment 1. This is shown in FIG. 5. As shown in FIG. 5, the strength of miR-199a inhibiting activity of S-TuDs is directly reflected in high luciferase activity. Further, six S-TuD concentrations at 10, 30, 100, 300, 1000 and 3000 pM were used.

Figure 9:
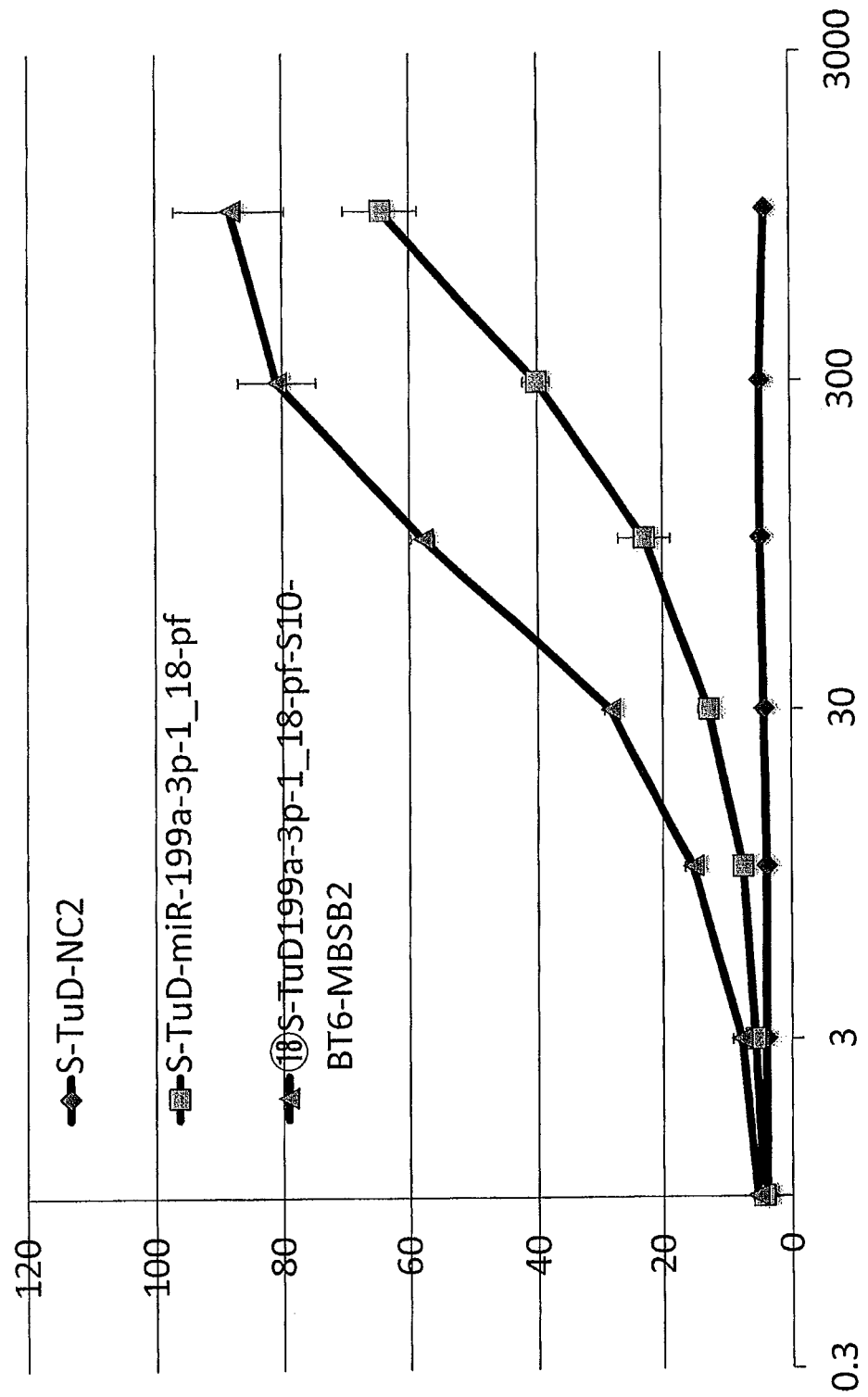
FIG. 9 shows results of a concentration dependency test when short type (stem 1=10, stem 2=10) stems are converted to BNA$^{NC}$(NMe) and the complementary sequence of the non-seed region of the MBS thereof is further modified by BNA$^{NC}$(NMe). The rhombus shapes indicate S-TuD NC2 (SEQ ID NOs: 57 and 58), squares indicate the original, and the triangles indicate (18). When short type (stem 1=10, stem 2=10) stems are converted to BNA$^{NC}$(NMe) and the complementary sequence of the non-seed region of the MBS thereof is further modified by BNA$^{NC}$(NMe), (18), the effect was nearly about 8-fold higher than the original (long type non-modified) without any BNA$^{NC}$(NMe) modification.

As can be seen from FIG. 9, further improvement in miRNA inhibiting activity due to an MBS region modification was observed. The length of a STEM region was the same as the original and a portion thereof was substituted with BNA$^{NC}$(NMe), which resulted in up to about 10-fold improvement in inhibitory activity compared to the original S-TuD. This indicates that improvement in physical properties has a positive effect on the activity itself. Further, up to 3-fold or more improvement in activity was confirmed even in cases where STEM I was shortened to 10 bp.

As discussed above, strengthened double strands enable reduction in cost by achieving a STEM region shortened S-TuD with the same activity.

Example 2: Substitution to MBS Region

The present Example studied the effect of substituting various positions, such as the MBS region with BNA$^{NC}$(NMe). The same reporter assay as in Example 1 was used. The sequences that were used are shown in FIGS. 10, 12, and 13.

(Structures that were Used)

In the present Example, the effect of substitution with BNA$^{NC}$(NMe) was first studied using S-TuDs with various structures to optimize the insertion site. FIGS. 6 and 7 show the structures of S-TuDs that were used: original S-TuD199a-3p, (16) S-TuD-miR-199a-3p-1_18-pf-L18B6-2, (22) S-TuD-miR-199a-3p-1_18-pf-L18B6-2-MBSB1 (complementary sequence to seed region includes BNA$^{NC}$(NMe)), (23) S-TuD-miR-199a-3p-1_18-pf-L18B6-2-MBSB2 (complementary sequence to non-seed region includes BNA$^{NC}$(NMe)), (24) S-TuD-miR-199a-3p-1_18-pf-L18B6-3-MBSB2 (complementary sequence to non-seed region includes BNA$^{NC}$(NMe)), (17) S-TuD199a-3p-1_18-pf-S10-BT6-MBSB1 (complementary sequence to seed region includes BNA$^{NC}$(NMe)), (18) S-TuD199a-3p-1_18-pf-S10-BT6-MBSB2 (complementary sequence to non-seed region includes BNA$^{NC}$(NMe)), (23)-(1) S-TuD-miR-199a-3p-1_18-pf-L18B6-2-PS1 (complementary sequence to non-seed region includes BNA$^{NC}$(NMe) and MBS region is phosphorothioated), (23)-(2) S-TuD-miR-199a-3p-1_18-pf-L18B6-2-PS2 (complementary sequence to non-seed region includes BNA$^{NC}$(NMe) and STEM region is phosphorothioated), and (23)-(3) S-TuD-miR-199a-3p-1_18-pf-L18B6-2-PS3 (complementary sequence to non-seed region includes BNA$^{NC}$(NMe) and all sequences are phosphorothioated).

(Assay Procedure)

The same reporter assay as in Example 1 was used.

(Results)

FIGS. 8-1 and 8-2 show results of substituting a portion of the MBS region with BNA$^{NC}$(NMe) for structures obtained in the present Example. As shown in FIGS. 8-1 and 8-2, it was possible to obtain a structure which had been observed with up to about 10-fold improvement in inhibitory activity compared to the original S-TuD. It was critical to insert BNA into a portion of the non-seed region of MBS region.

When stem regions of a long type (stem 1=18, stem 2=10) was converted to BNA (16), the suppression effect was not enhanced by adding an additional BNA modification to the complementary sequence of a non-seed region of an MBS (23). Further addition of a BNA modification to a complementary sequence of a seed region of an MBS in (16) slightly decreased the suppression effect (22). When stem regions of a short type (Stem 1=10, Stem 2=10) was converted to BNA and a complementary sequence of a non-seed region of an MBS was further modified by BNA (18), the effect was enhanced to nearly the same level as the long type (23). Addition of a PS modification to a stem structure significantly decreased the inhibitory effect (23-2), and addition thereof to an MBS (23-1) further decreased the effect. The inhibitory effect disappeared when added to both (23-3). The phosphorothioation of the backbone had a negative effect on activity, but the effect of BNA was retained.

Next, FIG. 9 shows results of studying the concentration dependency when short type (stem 1=10, stem 2=10) stems were converted to BNA and a complementary sequence of the non-seed region of the MBS thereof was further modified by BNA (18). When stem regions of a short type (stem 1=10, stem 2=10) stems were converted to BNA and the complementary sequence of the non-seed region of the MBS thereof was further modified by BNA (18), the effect was nearly about 10-fold higher than the original (long type non-modified) without any BNA modification as shown in FIG. 9.

In view of the above, the present invention provides an S-TuD comprising a modified nucleic acid promoting double-strand formation (Bridged Nucleic Acid=BNA, Locked Nucleic Acid=LNA, modified nucleic acid with any structure can be used as long as double-strand formation is promoted thereby) in STEM regions, and such S-TuDs were confirmed to have a significant effect of improving structural stability and inhibiting activity. It was also demonstrated that an effect is further enhanced by an S-TuD having a STEM I region, which is partially substituted with a BNA and shorted to, at minimum, 10-mer. In addition, it was demonstrated that an S-TuD with an miRNA non-seed region of an MBS that is partially substituted with BNA also achieves the same effect.

Such a technique is provided, enabling stable evaluation of physical properties and analysis of purity by reverse phase HPLC analysis, which could not be accomplished by conventional forms. Such stabilization has been confirmed for multiple target miRNAs to demonstrate that a universal effect is exhibited. Substitution of a portion of a STEM region with the same structure as a conventional form with BNA$^{NC}$(NMe) or broadly defined BNA such as LNA resulted in up to about 5-fold increase in miRNA inhibiting activity compared to the original S-TuD. The effect was confirmed for multiple target miRNAs to demonstrate that a universal effect is exhibited.

It was also confirmed that a partial BNA conversion of both STEMs in S-TuDs having STEM I shortened to a minimum of 10-mer results in up to about a 3-fold increase in activity compared to the original S-TuD. This effect has been confirmed for multiple target miRNAs to demonstrate that a universal effect is exhibited.

It was also confirmed that serum stability is improved in the present invention compared to conventional S-TuDs. Thus, the S-TuDs of the present invention can be provided as a stable medicament, so that they are expected to be utilized as a therapeutic agent when excessive expression of miRNAs is the cause of disease, such as cancer, and of course can be applied as an miRNA associated research reagent.

Example 3: Study of Effect of STEM Region Shortening + Insertion of BNA into MBS Region Next, the present Example, in view of the results in Examples 1 to 2, studied the effect of STEM region shortening + insertion of BNA into an MBS region.

(Structures that were Used)

FIG. 10 shows the following structures of S-TuDs that were used in the present Example: original sequence of S-TuD199a-3p; (16) S-TuD-miR-199a-3p-1_18-pf-L18B6-

2; (1)'S-TuD199a-3p-1_18-pf-S10; (6)'S-TuD199a-3p-1_18-pf-S10-BT6; (17) S-TuD199a-3p-1_18-pf-S10-BT6-MBSB1 (complementary sequence to seed region includes BNA$^{NC}$(NMe)); and (18) S-TuD199a-3p-1_18-pf-S10-BT6-MBSB2 (complementary sequence to non-seed region includes BNA$^{NC}$(NMe)).

(Experimental Method)

Expression was studied by an experimental method that is the same approach as the method of reporter assay described in Examples 1 to 2.

(Results)

FIGS. 11-1 and 11-2 show results for individual S-TuDs at 100 pM and 300 pM. As shown in FIGS. 11-1 and 11-2, the effect of BNA modifications on short types was studied. The original type and long type Stem-BNA modification (16) were added to the comparison. Compared to short type-BNA modification free (1)', the effect of (6)' with a BNA modification to the stem portion significantly increased. The effect of (17) with a further BNA modification to a seed corresponding site did not increase. However, the effect of (18) with a BNA modification to a non-seed corresponding site further increased, so that the effect was equal or greater than (16). It was found that there is an effect of enhancement for short types depending on the BNA modification site in an MBS.

Example 4: Stability in Serum

Next, the present Example studied the stability in serum using mouse serum.

(Experiment for Studying Serum Stability)

Improvement in serum stability relative to the original S-TuD was studied by a serum stability test. The protocol is shown below. The experiment performed treatment for 0h, 48h, 72h, and 96h at 37° C. under the conditions of 2 μg S-TuD/100% 20 μl mouse serum.

(Structure)

FIGS. 12 to 13 and 19 show the structures of the modified S-TuDs that were used, i.e., the original structure, (16) S-TuD-miR-199a-3p-1_18-pf-L18B6-2, (23) S-TuD-miR-199a-3p-1_18-pf-L18B6-2-MBSB2 (complementary sequence to non-seed region includes BNA$^{NC}$(NMe)), (23)-(1) S-TuD-miR-199a-3p-1_18-pf-L18B6-2-PS1 (complementary sequence to non-seed region includes BNA$^{NC}$(NMe)), (23)-(2) S-TuD-miR-199a-3p-1_18-pf-L18B6-2-PS2 (complementary sequence to non-seed region includes BNA$^{NC}$(NMe)) and (23)-(3) S-TuD-miR-199a-3p-1_18-pf-L18B6-2-PS3 (complementary sequence to non-seed region includes BNA$^{NC}$(NMe)), (1)'S-TuD199a-3p-1_18-pf-S10, (6)'S-TuD199a-3p-1_18-pf-S10-BT6, (17) S-TuD199a-3p-1_18-pf-S10-BT6-MBSB1 (complementary sequence to seed region includes BNA$^{NC}$(NMe)) and (18) S-TuD199a-3p-1_18-pf-S10-BT6-MBSB2 (complementary sequence to non-seed region includes BNA$^{NC}$(NMe)), (41) S-TuD-200c-1_22-pf, (42) S-TuD-200c-1_22-pf-L18B6, (43) S-TuD-200c-1_22-pf-L18B6-MBSB1 (complementary sequence to seed region includes BNA$^{NC}$(NMe)), (44) S-TuD-200c-1_22-pf-L18B6-MBSB2 (complementary sequence to non-seed region includes BNA$^{NC}$(NMe)), and (45) S-TuD-200c-1_22-pf-S10-BT6-MBSB2 (complementary sequence to non-seed region includes BNA$^{NC}$(NMe)).

(Results)

FIGS. 14 to 15 and 20 show the results. As shown in FIGS. 14 to 15 and 20, improvement in serum stability was observed as a result of substituting a portion of an MBS region with BNA$^{NC}$(NMe).

When stability in mouse serum was studied, long type S-TuDs exhibited nuclease resistance without modification, but smears increased over time. It is understood that this is due to slight degradation. Smears disappeared with BNA modification of the stem portion, acquiring full resistance. In this regard, an additional effect was not observed with further addition of MBS-BNA modifications.

When short type S-TuDs were studied, they were significantly degraded without modification, but exhibited slight nuclease resistance. Short type S-TuDs acquired full resistance with BNA modification of the stem portion. In this regard, an additional effect was not observed with further addition of MBS-BNA modifications.

Furthermore, universality was studied. As shown in FIG. 20, it was possible to confirm improvement in stability in serum for BNA$^{NC}$(NMe) substituted S-TuD-200c-1_22-pf similar to that of S-TuD199a.

In view of the above, smears in the top part of the main band disappeared and the stability was enhanced for both S-TuD199a and S-TuD200c by adding a BNA modification. The effect was enhanced more in S-TuDs with BNA modifications in both the Stem portion and the MBS portion than S-TuDs with a BNA modification only in the STEM portion. In particular, the stability enhancement effect in the short type ((1)', (6)' (17), and (18)) of S-TuD199a was significant, such that a BNA modification is considered essential for short types. A main band did not appear in unmodified long type (41), and smears were observed for S-TuD200c. Since a main band was observed for S-TuD199a, it is inferred that the secondary structure is associated therewith. A clear band in the top portion of the main band in all the results is understood to be a non-specific bond with serum proteins.

Example 5: Universality Experiment

The present Example conducted the same types of experiments using two types of miRNAs as targets to study universality.

(Experiment for Studying Universality)

A similar reporter assay experiment was conducted using S-TuDs with miR-199a in Example 1 substituted with miR-200c or miR-21. This is specifically disclosed below.

The assay method is identical to Example 1 and the like, except that the construct used in a reporter assay is substituted with miR-200c or miR-21.

(Structures that were Used)

FIG. 19 shows the structures for miR-200c. FIG. 23 shows the structures for miR-21. (41) S-TuD-200c-1_22-pf, (42) S-TuD-200c-1_22-pf-L18B6, (43) S-TuD-200c-1_22-pf-L18B6-MBSB1 (complementary sequence to seed region includes BNA$^{NC}$(NMe)), (44) S-TuD-200c-1_22-pf-L18B6-MBSB2 (complementary sequence to non-seed region includes BNA$^{NC}$(NMe)), and (45) S-TuD-200c-1_22-pf-S10-BT6-MBSB2 (complementary sequence to non-seed region includes BNA$^{NC}$(NMe)) were used for miR-200c. (51) S-TuD-21-1_17-10mut, (52) S-TuD-21-1_17-10mut-L18B6, (53) S-TuD-21-1_17-10mut-L18B6-MBSB1, (54) S-TuD-21-1_17-10mut-S10-BT6, and (55) S-TuD-21-1_17-10mut-S10-BT6-MBSB1 were used for miR-21.

(Results)

Next, universality was studied. For universality, the same experiment as Example 1 was conducted for miR-200c and miR-21 in addition to miR-199a. FIG. 20 shows the results of electrophoresis indicating serum resistance. FIGS. 21-1 and 21-2 (miR-200c) are graphs of results with miR-200c. As shown in FIGS. 21-1 and 21-2 showing the results of a reporter assay, when a long type (stem 1=18, stem 2=10)

stem was converted to BNA (42), the suppression effect was not enhanced by adding an additional BNA$^{NC\ (NMe)}$ modification to the complementary sequence of the non-seed region of the MBS (44). Further addition of a BNA$^{NC}$(NMe) modification to a complementary sequence of a seed region of an MBS in (42) decreased the suppression effect (43). When a short type (Stem 1=10, Stem 2=10) stem was converted to BNA$^{NC}$(NMe) and a complementary sequence of the non-seed region of the MBS was further modified by BNA$^{NC}$(NMe) (45), the effect was enhanced to nearly the same level as the long type (44). As shown in FIG. 22, when a short type (Stem 1=10, Stem 2=10) stem was converted to BNA$^{NC}$(NMe) and a complementary sequence of the non-seed region of the MBS was further modified by BNA (45), the effect was nearly 2-fold higher than the original (41) without any BNA$^{NC}$(NMe) modification. In view of the possibility that S-TuDs were absorbed non-specifically to a tube with a dosage of 0.1 to 10 pM, analysis was also performed with 30 pM of S-TuD NC2 added as a carrier, but an effect of the addition was not observed.

In view of the above, it was found that the activity of a type of S-TuD in which a short type (Stem 1=10, Stem 2=10) stem was converted to BNA$^{NC}$(NMe) and a complementary sequence to the non-seed region of the MBS was further modified by BNA$^{NC}$(NMe) was not inferior to any of the long types. Further, a type of S-TuD in which a short type (Stem 1=10, Stem 2=10) stem was converted to BNA$^{NC}$(NMe) and a complementary sequence to the non-seed region of the MBS was further modified by BNA$^{NC}$(NMe) had inhibitory activity that was elevated about 10-fold for target miR-199a and about 2-fold for target miR-200c relative to the original without a BNA$^{NC}$(NMe) modification.

In this manner, about the same result was confirmed for miR-200c in addition to miR-199a.

When the same effect was studied for miR-21, the same effect was exhibited. FIGS. 24 to 26 show the results. FIG. 24 shows electropherograms after mouse serum treatment. For S-TuD21, a main band did not appear and smears were observed for the unmodified long type (51). A clear main band was obtained for modified S-TuDs (52 to 55). Thus, improvement in stability in serum was confirmed. A clear band in the top portion of the main band in all the results is understood to be a non-specific bond with serum proteins. FIGS. 25-1 and 25-2 (miR-21) show graphs of results of a reporter assay for miR-21. A slight increase in effect was observed for (52) with a BNA$^{NC}$(NMe) modification of the stem portion compared to S-TuD21 (original; 51). Furthermore, the effect was increased nearly 10-fold in 53 with a modification of a non-seed region portion of an MBS. The effect increased 3-fold or more for (55) with a modification of a non-seed region portion of an MBS compared to the original (51) for short types, but the effect was slightly weaker compared to long type (53). When concentration dependency was studied as shown in FIG. 26, the effect increased nearly 10-fold for (53) with a BNA$^{NC}$(NMe) modification of a non-seed region portion of an MBS and stem portion compared to the original (51). The effect increased 3-fold or more in (55) with a modification in a non-seed region portion of an MBS compared to the original (51) for short types, but the effect was about ⅔-fold compared to long type (53).

(Discussion of Strength of Inhibitory Effect)

Among all of 199a, 200c, and 21, the effect was the highest for those that are long type and have a BNA modification in both the stem portion and non-seed corresponding site of an MBS (abbreviated as A). Short type stem, MBS-BNA modified forms have a lower effect than A, but the inhibitory effect was significantly higher than the original. The extent of enhancement for BNA$^{NC}$(NMe) modified long types was that the activity was nearly 10-fold higher than conventional forms for 199a and 21. The extent of enhancement for BNA$^{NC}$(NMe) modified short types was that the activity was about 3 to 8-fold higher than conventional forms for 199a and 21. It is presumed that the extent of enhancement is low for 200c because a difference does not readily manifest, as there is already an inhibitory effect at pM levels, perhaps due to the low expression level and activity of miR-200c.

In view of the above, regardless of long type or short type, insertion of BNA$^{NC}$(NMe) modifications in both the stem portion and non-seed corresponding site of an MBS is recommended from the viewpoint of both effect and stability. Especially in short types, BNA$^{NC}$(NMe) conversion of the stem portion is considered desirable. The extent of the effect of BNA$^{NC}$(NMe) at a non-seed corresponding site of an MBS significantly varies depending on the miRNA type for long types. As for the stem length, it appears that the effect is slightly higher for long types than short types, in view of the in vitro results.

Example 6: In Vivo Experiment

Next, the present Example studied whether the S-TuD of the present invention can be clinically applied.

(Structures)

FIG. 27 shows the structures that were used, i.e., (51) S-TuD-21-1_17-10mut, (53) S-TuD-21-1_17-10mut-L18B6-MBSB1, and (55) S-TuD-21-1_17-10mut-S10-BT6-MBSB1.

(Protocol)

A single dose of each S-TuD was administered to the orbital vein of mice (C57BL/6, 6 weeks old, male) at 1 mg/kg (n=3). After 24 hours, the mice were sacrificed. The kidneys were collected to quantify the amount of miR-21 (free miR-21 which is not considered to be bound to S-TuD) by RT-PCR.

(Results)

FIGS. 28 to 29 show the results.

When the amount of miR-21 in the kidney was measured by RT-PCR, the inhibitory activity was the highest for 53, followed by 55, as shown in FIG. 28. When the mean value of miR-21 in the kidneys of three mice was measured, decrease in miR-21 was hardly observed for the original S-TuD, but a decrease is detected in 53 and, to a lesser extent, 55, as shown in FIG. 29.

It is known that miR-122 inhibitors (LNA-ASO) have advanced to PII as an HCV therapeutic agent. Regulus has completed Phase I and non-clinical trials, and is currently at Phase II for miR-21 inhibitor (LNA-ASO) included in the present tests as a therapeutic drug for suppressing renal fibrosis. In view of the above, the results in the present Example should be considered in vivo data indicating that the S-TuD of the present invention can be utilized as a medicament.

Example 7: Comparative Trial of Various Bridged Nucleic Acids

Next, the present Example, in view of the results in Examples 1 to 7, substituted the same position as BNA$^{NC}$(NMe) with a locked nucleic acid (LNA; 2'-O,4'-C-methyl ribonucleic acid), and compared the activity in order to confirm that a substitution of a modified base with high double-strand formation capability into the STEM region improves miRNA inhibitory activity.

FIG. 32 shows the sequence structures.

The S-TuD basic structure is 10-MBS-10 type in which STEM I is shortened to 10 bp (shown in (5)).

The assay method used was the same approach as the luciferase reporter assay of miR199a used in Example 1 and the like.

(Results)

FIGS. 33-1 and 33-2 show the results. BNA$^{NC}$(NMe) and LNA have an equivalent effect, confirming structural universality. Activity was equivalent to substitutions at 4 sites even with BNA$^{NC}$(NMe) substitutions at 6 sites in the 10 bp STEM region.

Example 8: STEM Region Shortening Test

Next, the present Example shortened the STEM region to compare activity.

FIG. 34 shows the sequences that were used.

The assay method used was the same approach as the luciferase reporter assay of miR199a used in Example 1 and the like.

The relationship between stem length and the number of BNA$^{NC}$(NMe) in the sequences that were used in the present Examples is shown below.

TABLE 1

|  |  | Number of BNA$^{NC}$(NMe) | |
|---|---|---|---|
|  |  | 6 | 4 |
| Stem length | 10 bp | (6)' | (1)" |
|  | 8 bp | (2)" | (3)" |
|  | 6 bp | (4)" | (5)" |

(Results)

FIGS. 35-1 and 35-2 show the results. The activity decreased to ⅕ or less when the STEM region was 8 bp or less. However, concentration dependent elevation in activity is observed even at 6 bp. Thus, it is desirable that the STEM region is 10 bp or greater. Together with the results in FIG. 32, it was confirmed that BNA substitution is desirable when the stem length is 10 bp or less.

Example 9: Test for Correlation in Activity Between STEM Region Shortening and Bridged Nucleic Acid Substitution In the present Example, the combination of STEM region shortening and bridged nucleic acid substitution was comprehensively evaluated by comparing the original S-TuD (STEM I 18 bp, STEM II 10 bp) with S-TuD prepared by a BNA substitution in each of STEMs I and II of the original S-TuD.

FIG. 36 shows the sequence structures that were used. The assay method used was the same approach as the luciferase reporter assay of miR199a shown in Example 1 and the like.

(Results)

FIGS. 37-1 and 37-2 show the results. Assuming miRNA inhibiting activity is 1 for the original S-TuD, improvement in activity was 3-fold or greater for S-TuDs prepared by a BNA substitution in each of STEMs I and II of the original S-TuD and about 3-fold for S-TuD prepared with STEM I shortened to 10 bp and a BNA$_{NC}$(NMe) substitution. This demonstrates that strengthened double-strand formation of STEM plays a significant role in miRNA inhibiting activity of S-TuDs.

The present invention has been disclosed based on the Examples. These embodiments are exemplifications. It is understood by those skilled in the art that various modified examples are possible and such modified examples are also within the scope of the present invention.

As described above, the present invention is exemplified by the use of its preferred embodiments. However, it is understood that the scope of the present invention should be interpreted solely based on the Claims. It is also understood that any patent, patent application, and reference cited herein should be incorporated herein by reference in the same manner as the contents specifically described. The present application claims priority to Japanese Patent Application No. 2015-185365 filed on Sep. 18, 2015. The entire content thereof is incorporated herein by reference.

INDUSTRIAL APPLICABILITY

The present invention is useful in the drug development industry and reagent industry using nucleic acid medicaments and the like.

SEQUENCE LISTING FREE TEXT

SEQ ID NO: 1: Original sense sequence of FIG. 2A (same for FIG. 4-1)
SEQ ID NO: 2: Original antisense sequence of FIG. 2A
SEQ ID NO: 3: Sense sequence of FIG. 2A (1)
SEQ ID NO: 4: Antisense sequence of FIG. 2A (1)
SEQ ID NO: 5: Sense sequence of FIG. 2A (2)
SEQ ID NO: 6: Antisense sequence of FIG. 2A (2)
SEQ ID NO: 7: Sense sequence of FIG. 2A (3)
SEQ ID NO: 8: Antisense sequence of FIG. 2A (3)
SEQ ID NO: 9: Sense sequence of FIG. 2A (4)
SEQ ID NO: 10: Antisense sequence of FIG. 2A (4)
SEQ ID NO: 11: Sense sequence of FIG. 2A (5)
SEQ ID NO: 12: Antisense sequence of FIG. 2A (5)
SEQ ID NO: 13: Sense sequence of FIG. 6 (16)
SEQ ID NO: 14: Antisense sequence of FIG. 6 (16)
SEQ ID NO: 15: Sense sequence of FIG. 6 (22)
SEQ ID NO: 16: Antisense sequence of FIG. 6 (22)
SEQ ID NO: 17: Sense sequence of FIG. 6 (23)
SEQ ID NO: 18: Antisense sequence of FIG. 6 (23)
SEQ ID NO: 19: Sense sequence of FIG. 6 (24)
SEQ ID NO: 20: Antisense sequence of FIG. 6 (24)
SEQ ID NO: 21: Sense sequence of FIG. 7 (17)
SEQ ID NO: 22: Antisense sequence of FIG. 7 (17)
SEQ ID NO: 23: Sense sequence of FIG. 7 (18)
SEQ ID NO: 24: Antisense sequence of FIG. 7 (18)
SEQ ID NO: 25: Sense sequence of FIG. 7 (23)-(1)
SEQ ID NO: 26: Antisense sequence of FIG. 7 (23)-(1)
SEQ ID NO: 27: Sense sequence of FIG. 7 (23)-(2)
SEQ ID NO: 28: Antisense sequence of FIG. 7 (23)-(2)
SEQ ID NO: 29: Sense sequence of FIG. 7 (23)-(3)
SEQ ID NO: 30: Antisense sequence of FIG. 7 (23)-(3)
SEQ ID NO: 31: Sense sequence of FIG. 10 (1)'
SEQ ID NO: 32: Antisense sequence of FIG. 10 (1)'
SEQ ID NO: 33: Sense sequence of FIG. 10 (6)'
SEQ ID NO: 34: Antisense sequence of FIG. 10 (6)'
SEQ ID NO: 35: Sense sequence of FIG. 12 (23)
SEQ ID NO: 36: Antisense sequence of FIG. 12 (23)
SEQ ID NO: 37: Sense sequence of FIG. 19 (41)
SEQ ID NO: 38: Antisense sequence of FIG. 19 (41)
SEQ ID NO: 39: Sense sequence of FIG. 19 (42)

SEQ ID NO: 40: Antisense sequence of FIG. 19 (42)
SEQ ID NO: 41: Sense sequence of FIG. 19 (43)
SEQ ID NO: 42: Antisense sequence of FIG. 19 (43)
SEQ ID NO: 43: Sense sequence of FIG. 19 (44)
SEQ ID NO: 44: Antisense sequence of FIG. 19 (44)
SEQ ID NO: 45: Sense sequence of FIG. 19 (45)
SEQ ID NO: 46: Antisense sequence of FIG. 19 (45)
SEQ ID NO: 47: Sense sequence of FIG. 23 (51)
SEQ ID NO: 48: Antisense sequence of FIG. 23 (51)
SEQ ID NO: 49: Sense sequence of FIG. 23 (52)
SEQ ID NO: 50: Antisense sequence of FIG. 23 (52)
SEQ ID NO: 51: Sense sequence of FIG. 23 (53)
SEQ ID NO: 52: Antisense sequence of FIG. 23 (53)
SEQ ID NO: 53: Sense sequence of FIG. 23 (54)
SEQ ID NO: 54: Antisense sequence of FIG. 23 (54)
SEQ ID NO: 55: Sense sequence of FIG. 23 (55)
SEQ ID NO: 56: Antisense sequence of FIG. 23 (55)
SEQ ID NO: 57: Sense sequence of S-TuD NC2 (FIG. 18 and FIG. 22)
SEQ ID NO: 58: Antisense sequence of S-TuD NC2 (FIG. 18 and FIG. 22)
SEQ ID NO: 59: Sense sequence of FIG. 32 (2)'
SEQ ID NO: 60: Antisense sequence of FIG. 32 (2)'
SEQ ID NO: 61: Sense sequence of FIG. 32 (7)'
SEQ ID NO: 62: Antisense sequence of FIG. 32 (7)'
SEQ ID NO: 63: Sense sequence of FIG. 32 (8)'
SEQ ID NO: 64: Antisense sequence of FIG. 32 (8)'
SEQ ID NO: 65: Sense sequence of FIG. 34 (1)"
SEQ ID NO: 66: Antisense sequence of FIG. 34 (1)"
SEQ ID NO: 67: Sense sequence of FIG. 34 (2)"
SEQ ID NO: 68: Antisense sequence of FIG. 34 (2)"
SEQ ID NO: 69: Sense sequence of FIG. 34 (3)"
SEQ ID NO: 70: Antisense sequence of FIG. 34 (3)"
SEQ ID NO: 71: Sense sequence of FIG. 34 (4)"
SEQ ID NO: 72: Antisense sequence of FIG. 34 (4)"
SEQ ID NO: 73: Sense sequence of FIG. 34 (5)"
SEQ ID NO: 74: Antisense sequence of FIG. 34 (5)"
SEQ ID NO: 75: psiCHECK2-T200c-3p-s of FIG. 17 (Sense sequence)
SEQ ID NO: 76: psiCHECK2-T200c-3p-a of FIG. 17 (Antisense sequence)
SEQ ID NO: 77: psiCHECK2-T199a-3px3-s of FIG. 17 (Sense sequence)
SEQ ID NO: 78: psiCHECK2-T199a-3px3-a of FIG. 17 (Antisense sequence)
SEQ ID NO: 79: psiCHECK2-T21-5p-s of FIG. 17 (Sense sequence)
SEQ ID NO: 80: psiCHECK2-T21-5p-a of FIG. 17 (Antisense sequence)

The invention claimed is:

1. An miRNA inhibiting complex comprising an RNA or an analog thereof, the miRNA inhibiting complex comprising at least one double-stranded structure and at least one miRNA binding sequence, wherein the miRNA binding sequence is bound to one of two strands on at least one end of the double-stranded structure, and wherein the miRNA inhibiting complex comprises at least one bridged nucleic acid (BNA) in a stem region of the miRNA inhibiting complex.

2. The complex of claim 1, wherein the BNA comprises a BNA that is bridged via at least one atom selected from the group consisting of oxygen and carbon on the position 2' side and via at least one atom selected from the group consisting of carbon and nitrogen and carbon on the position 4' side.

3. The complex of claim 1, wherein the BNA comprises a 2',4' substituted bridged nucleic acid represented by

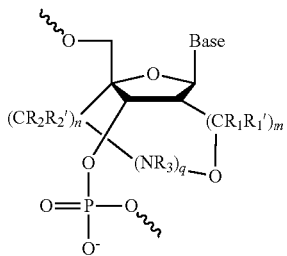

BNA-1 wherein $R_1$, $R_1'$, $R_2$, $R_2'$, and $R_3$ each independently represent a group selected from the group consisting of a hydrogen atom, a substituted or unsubstituted alkyl group, a substituted or unsubstituted alkenyl group, a substituted or unsubstituted cycloalkyl group, a substituted or unsubstituted aryl group, a substituted or unsubstituted aralkyl group, a substituted or unsubstituted acyl group, a substituted or unsubstituted sulfonyl group, a substituted or unsubstituted silyl group, and a functional molecule unit substituent, m is an integer from 0 to 2, Base represents a group selected from the group consisting of an adeninyl group, a thyminyl group, a uracilyl group, an inosinyl group, a cytosinyl group, a guaninyl group, and a methylcytosinyl group, n is an integer from 1 to 3, and q is an integer that is 0 or 1.

4. The complex of claim 1, wherein the BNA comprises a 2',4' substituted bridged nucleic acid represented by

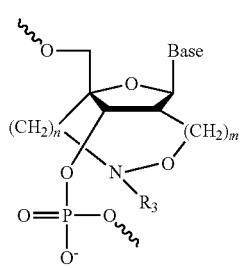

BNA-2 wherein $R_3$ represents a group selected from the group consisting of a hydrogen atom, an alkyl group, an alkenyl group, a cycloalkyl group, an aryl group, an aralkyl group, an acyl group, a sulfonyl group, a silyl group, and a functional molecule unit substituent, Base represents a group selected from the group consisting of an adeninyl group, a thyminyl group, a uracilyl group, an inosinyl group, a cytosinyl group, a guaninyl group, and a methylcytosinyl group, m is an integer from 0 to 2, and n is an integer from 1 to 3.

5. The complex of claim 1, wherein the BNA comprises

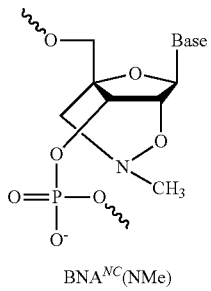

BNA$^{NC}$(NMe)

or a 2',4'-methano bridged nucleic acid (LNA) or the BNA is BNA$^{NC}$(NMe).

6. The complex of claim 1, wherein the BNA is comprised in at least one of the strands of the double-stranded structure moiety and at least one strand of complementary strands of the miRNA binding sequence.

7. The complex of claim 1, wherein the BNA is comprised in at least one of the strands of the double-stranded structure moiety.

8. The complex of claim 7, wherein the BNA is comprised in both strands of the double-stranded structure moiety.

9. The complex of claim 1, wherein two or more of the BNA are comprised, or four or more of the BNA are comprised; or six or more of the BNA are comprised.

10. The complex of claim 1, wherein the complex comprises two or more of the double-stranded structures, wherein strands comprising the miRNA binding sequence are each bound to one of two strands on one end of a first double-stranded structure of the double-stranded structure, and the other ends of the strands are each bound to one of two strands of a second double-stranded structure of the two or more of the double-stranded structures, so that the strands are sandwiched between the two or more of the double-stranded structures.

11. The complex of claim 1, wherein an end of two strands comprising the miRNA binding sequence is bound via a linker.

12. The complex of claim 11, wherein a length of the linker is 1 to 5 bases long.

13. The complex of claim 1, wherein the double-stranded structure is at least 6 bases long; or the double-stranded structure is at least 8 bases long; or the double-stranded structure is at least 10 bases long; or the double-stranded structure is at least 15 bases long; or the double-stranded structure is at least 18 bases long.

14. The complex of claim 13, wherein the double-stranded structure is 50 bases long or less.

15. The complex of claim 1, comprising 2 to 5 miRNA binding sequences.

16. The complex of claim 15, comprising two miRNA binding sequences.

17. The complex of claim 10, comprising the following structure represented by

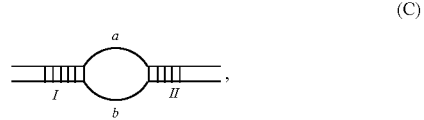

(C)

wherein I and II of the structure are double-stranded structures, and each of a and b of the structure comprises an miRNA binding sequence.

18. An RNA constituting the complex of claim 1, or an analog thereof.

* * * * *

UNITED STATES PATENT AND TRADEMARK OFFICE
CERTIFICATE OF CORRECTION

PATENT NO. : 10,844,376 B2  
APPLICATION NO. : 15/761018  
DATED : November 24, 2020  
INVENTOR(S) : Hideo Iba et al.

Page 1 of 1

It is certified that error appears in the above-identified patent and that said Letters Patent is hereby corrected as shown below:

On the Title Page

Under item (73) Assignees:  
"(73) Assignees:    University of Tokyo, Tokyo (JP)  
                   GeneDesign, Inc., Osaka (JP)"  
Should read:  
--(73) Assignees:    The University of Tokyo, Tokyo (JP)  
                    GeneDesign, Inc., Osaka (JP)--

Signed and Sealed this  
Third Day of August, 2021

Drew Hirshfeld  
*Performing the Functions and Duties of the*  
*Under Secretary of Commerce for Intellectual Property and*  
*Director of the United States Patent and Trademark Office*